(12) United States Patent  
Marinier et al.

(10) Patent No.: US 8,148,400 B2
(45) Date of Patent: Apr. 3, 2012

(54) THIAZOLYL COMPOUNDS USEFUL AS KINASE INHIBITORS

(75) Inventors: Anne Marinier, Kirkland (CA); Claude A. Quesnelle, Skillman, NJ (US); Marco Dodier, Wotton (CA); Stephan Roy, Levis (CA); Patrice Gill, Levittown, PA (US); Mark D. Wittman, Wallingford, CT (US); David R. Langley, Meriden, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 307 days.

(21) Appl. No.: 12/519,597

(22) PCT Filed: Dec. 19, 2007

(86) PCT No.: PCT/US2007/088124
§ 371 (c)(1),
(2), (4) Date: Jun. 17, 2009

(87) PCT Pub. No.: WO2008/079873
PCT Pub. Date: Jul. 3, 2008

(65) Prior Publication Data
US 2010/0048581 A1 Feb. 25, 2010

Related U.S. Application Data

(60) Provisional application No. 60/870,872, filed on Dec. 20, 2006.

(51) Int. Cl.
*C07D 417/14* (2006.01)
*C07D 495/04* (2006.01)
*A61K 31/4436* (2006.01)

(52) U.S. Cl. ........ 514/318; 514/333; 546/193; 546/194; 546/256

(58) Field of Classification Search ........... 546/193, 546/194, 256; 514/318, 333
See application file for complete search history.

(56) References Cited

U.S. PATENT DOCUMENTS

2003/0069238 A1 4/2003 Barrish et al.
2004/0220233 A1 11/2004 Hynes et al.

OTHER PUBLICATIONS

Traxler, Protein Tyrosine Kinase Inhibitors in Cancer Treatment, Exp. Opin. Ther. Patents, 7(6), 571-588 (1997).*
Johnson et al., Relationships between drug activity in NCI preclinical in vitro and in vivo models and early clinical trials, British Journal of Cancer (2001) 64(10): 1424-1431.*
Gura, Systems for Identifying New Drugs Are Often Faulty, Cancer Models, Science, vol. 278, No. 5340, pp. 1041-1042, Nov. 1997.*
Simone, Oncology: Introduction, Cecil Textbook of Medicine, 20th Edition, vol. 1, pp. 1004-1010, 1996.*
LeRoith et al., The Insulin-like Growth Factor system and cancer, Cancer Letters, 195 (2003), pp. 127-137.*

* cited by examiner

*Primary Examiner* — Deepak Rao
(74) *Attorney, Agent, or Firm* — Elliott Korsen

(57) ABSTRACT

The invention provides compounds of formula II:

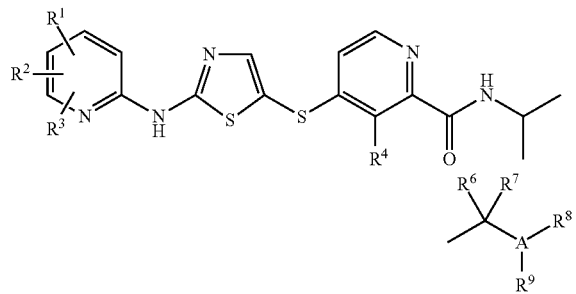

and pharmaceutically acceptable salts thereof. The formula II thiazolyl compounds inhibit tyrosine kinase activity thereby making them useful as anticancer agents and for the treatment of Alzheimer's Disease.

5 Claims, No Drawings

THIAZOLYL COMPOUNDS USEFUL AS KINASE INHIBITORS

FIELD OF THE INVENTION

The invention relates to novel thiazolyl compounds that are useful as anti-cancer agents. This invention also relates to a method of using the compounds in the treatment of proliferative and other types of diseases and to pharmaceutical compositions containing the compounds.

BACKGROUND OF THE INVENTION

The invention relates to thiazolyl compounds which inhibit tyrosine kinase enzymes, compositions which contain tyrosine kinase inhibiting compounds and methods of using inhibitors of tyrosine kinase enzymes to treat diseases which are characterized by an overexpression or upregulation of tyrosine kinase activity such as cancer, diabetes, restenosis, arteriosclerosis, psoriasis, Alzheimer's disease, angiogenic diseases and immunologic disorders (Powis, G.; Workman P. Signaling Targets For The Development of Cancer Drugs. *Anti-Cancer Drug Design* (1994), 9: 263-277; Merenmies, J.; Parada, L. F.; Henkemeyer, M. Receptor Tyrosine Kinase Signaling in Vascular Development. *Cell Growth Differ* (1997) δ: 3-10; Shawver, L. K.; Lipsosn, K. E.; Fong, T. A. T.; McMahon, G.; Plowman, G. D.; Strawn, L. M. Receptor Tyrosine Kinases As Targets For Inhibition of Angiogenesis. *Drug Discovery Today* (1997) 2: 50-63; all herein incorporated by reference).

Tyrosine kinases play a critical role in signal transduction for several cellular functions including cell proliferation, carcinogenesis, apoptosis, and cell differentiation Inhibitors of these enzymes are useful for the treatment or prevention of proliferative diseases which are dependent on these enzymes. Strong epidemiologic evidence suggests that the overexpression or activation of receptor protein tyrosine kinases leading to constitutive mitogenic signaling is an important factor in a growing number of human malignancies. Tyrosine kinases that have been implicated in these processes include Abl, CDK's, EGF, EMT, FGF, FAK, Flk-1/KDR, Flt-3, GSK-3, GSKbeta-3, HER-2, IGF-1R, IR, Jak2, LCK, MET, PDGF, Src, Tie-2, TrkA, TrkB and VEGF. Hence, there is an ongoing need to investigate novel compounds that can be used to regulate or inhibit tyrosine kinase enzymes.

SUMMARY OF THE INVENTION

The invention is directed to thiazolyl compounds of formula I that inhibit tyrosine kinase enzymes for the treatment of cancer.

Furthermore, the invention is directed to methods for treating a condition associated with one or more tyrosine kinase inhibitor comprising administering to a mammal in need of such treatment a therapeutically effective amount of a compound of formula I and optionally one or more other anticancer agent.

The invention also provides methods for treating cancer using the compounds of the invention either alone or together with one or more other anticancer agent or therapies, such as radiation.

DETAILED DESCRIPTION OF THE INVENTION

The invention provides novel thiazolyl compounds useful as anti-cancer agents, pharmaceutical compositions employing said novel compounds and methods of using said compounds.

In accordance with the invention, there are disclosed compounds of formula I

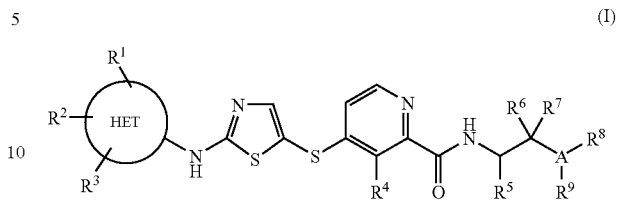

(I)

or a pharmaceutically acceptable salt or a stereoisomer thereof, wherein:

HET is a heteroaryl or heterocyclyl group;

A is an aryl or a heteroaryl group;

$R^1$, $R^2$ and $R^3$ are independently hydrogen, alkyl, substituted alkyl, aryl, substituted aryl, cycloalkyl, substituted cycloalkyl, hydroxy, hydroxyalkyl, alkoxy, substituted alkoxy, halogen, haloalkyl, haloalkoxy, alkanoyl, substituted alkanoyl, amino, substituted amino, aminoalkyl, substituted aminoalkyl, alkylamino, substituted alkylamino, amide, substituted amide, carbamate, ureido, cyano, sulfonamido, substituted sulfonamido, alkylsulfone, nitro, thio, thioalkyl, alkylthio, disubstituted amino, alkylsulfonyl, alkylsulfinyl, carboxy, alkoxycarbonyl, alkylcarbonyloxy, carbamoyl, substituted carbamoyl, alkenyl, substituted alkenyl, alkynyl, substituted alkynyl or alkylcarbonyl; or $R^1$ and $R^2$ are taken together to form an optionally substituted carbocyclic or heterocyclic ring;

$R^4$ is hydrogen, alkyl, substituted alkyl, hydroxy, cyano or halogen;

$R^5$, $R^6$ and $R^7$ are independently hydrogen, alkyl, substituted alkyl, aryl, substituted aryl, hydroxy, hydroxyalkyl, alkoxy, substituted alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino or alkylaminocarbonyl;

$R^8$ and $R^9$ are independently hydrogen, alkyl, substituted alkyl, aryl, substituted aryl, alkylidene, substituted alkylidene, hydroxy, hydroxyalkyl, alkoxy, substituted alkoxy, alkoxyalkoxyalkyl halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, alkynyl, substituted alkynyl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino or alkylaminocarbonyl, or $R^8$ and $R^9$ are taken together with the atoms to which they are attached to form an optionally substituted carbobicyclic or heterobicyclic ring.

In another aspect of the invention, there are disclosed compounds of formula II

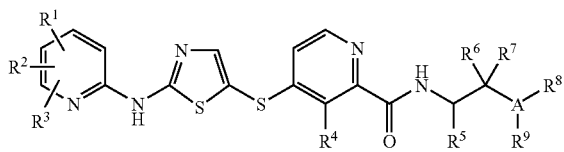

(II)

or a pharmaceutically acceptable salt or a stereoisomer thereof, wherein:

A is an aryl or a heteroaryl group;

$R^1$, $R^2$ and $R^3$ are independently hydrogen, alkyl, substituted alkyl, aryl, substituted aryl, cycloalkyl, substituted cycloalkyl, hydroxy, hydroxyalkyl, alkoxy, substituted alkoxy, halogen, haloalkyl, haloalkoxy, alkanoyl, substituted alkanoyl, amino, substituted amino, aminoalkyl, substituted aminoalkyl, alkylamino, substituted alkylamino, amide, substituted amide, carbamate, ureido, cyano, sulfonamido, substituted sulfonamido, alkylsulfone, nitro, thio, thioalkyl, alkylthio, disubstituted amino, alkylsulfonyl, alkylsulfinyl, carboxy, alkoxycarbonyl, alkylcarbonyloxy, carbamoyl, substituted carbamoyl, alkenyl, substituted alkenyl, alkynyl, substituted alkynyl or alkylcarbonyl; or $R^1$ and $R^2$ are taken together to form an optionally substituted carbocyclic or heterocyclic ring;

$R^4$ is hydrogen, alkyl, substituted alkyl, hydroxy, cyano or halogen;

$R^5$, $R^6$ and $R^7$ are independently hydrogen, alkyl, substituted alkyl, aryl, substituted aryl, hydroxy, hydroxyalkyl, alkoxy, substituted alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkynyl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino or alkylaminocarbonyl;

$R^8$ and $R^9$ are independently hydrogen, alkyl, substituted alkyl, aryl, substituted aryl, alkylidene, substituted alkylidene, hydroxy, hydroxyalkyl, alkoxy, substituted alkoxy, alkoxyalkoxyalkyl halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino or alkylaminocarbonyl, or $R^8$ and $R^9$ are taken together with the atoms to which they are attached to form an optionally substituted carbobicyclic or heterobicyclic ring.

In another aspect of the invention, there are disclosed compounds of formula III

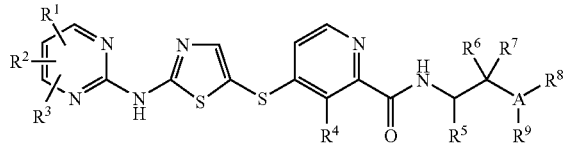

(III)

or a pharmaceutically acceptable salt or a stereoisomer thereof, wherein:

A is an aryl or a heteroaryl group;

$R^1$, $R^2$ and $R^3$ are independently hydrogen, alkyl, substituted alkyl, aryl, substituted aryl, cycloalkyl, substituted cycloalkyl, hydroxy, hydroxyalkyl, alkoxy, substituted alkoxy, halogen, haloalkyl, haloalkoxy, alkanoyl, substituted alkanoyl, amino, substituted amino, aminoalkyl, substituted aminoalkyl, alkylamino, substituted alkylamino, amide, substituted amide, carbamate, ureido, cyano, sulfonamido, substituted sulfonamido, alkylsulfone, nitro, thio, thioalkyl, alkylthio, disubstituted amino, alkylsulfonyl, alkylsulfinyl, carboxy, alkoxycarbonyl, alkylcarbonyloxy, carbamoyl, substituted carbamoyl, alkenyl, substituted alkenyl, alkynyl, substituted alkynyl or alkylcarbonyl; or $R^1$ and $R^2$ are taken together to form an optionally substituted carbocyclic or heterocyclic ring;

$R^4$ is hydrogen, alkyl, substituted alkyl, hydroxy, cyano or halogen;

$R^5$, $R^6$ and $R^7$ are independently hydrogen, alkyl, substituted alkyl, aryl, substituted aryl, hydroxy, hydroxyalkyl, alkoxy, substituted alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkynyl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino or alkylaminocarbonyl;

$R^8$ and $R^9$ are independently hydrogen, alkyl, substituted alkyl, aryl, substituted aryl, alkylidene, substituted alkylidene, hydroxy, hydroxyalkyl, alkoxy, substituted alkoxy, alkoxyalkoxyalkyl halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino or alkylaminocarbonyl, or $R^8$ and $R^9$ are taken together with the atoms to which they are attached to form an optionally substituted carbobicyclic or heterobicyclic ring.

In another aspect of the invention, there are disclosed compounds of formula IV

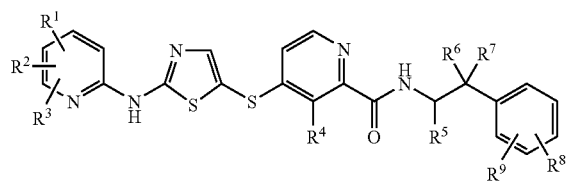

(IV)

or a pharmaceutically acceptable salt or a stereoisomer thereof, wherein:

$R^1$, $R^2$ and $R^3$ are independently hydrogen, alkyl, substituted alkyl, aryl, substituted aryl, cycloalkyl, substituted cycloalkyl, hydroxy, hydroxyalkyl, alkoxy, substituted alkoxy, halogen, haloalkyl, haloalkoxy, alkanoyl, substituted alkanoyl, amino, substituted amino, aminoalkyl, substituted aminoalkyl, alkylamino, substituted alkylamino, amide, substituted amide, carbamate, ureido, cyano, nitro, carboxy, alkoxycarbonyl, alkylcarbonyloxy, carbamoyl, substituted carbamoyl, alkenyl, substituted alkenyl, alkynyl, substituted alkynyl or alkylcarbonyl; or $R^1$ and $R^2$ are taken together to form an optionally substituted carbocyclic or heterocyclic ring;

$R^4$ is hydrogen, alkyl, substituted alkyl, hydroxy, cyano or halogen;

$R^5$, $R^6$ and $R^7$ are independently hydrogen, alkyl, substituted alkyl, aryl, substituted aryl, hydroxy, hydroxyalkyl, alkoxy, substituted alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, disubstituted amino, amide, substituted amide, carbamate, substituted carbamate, ureido, cyano, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, carboxy, alkoxycarbonyl, alkylcarbonyloxy, carbamoyl, alkenyl, substituted alkynyl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylcarbonylamino or alkylaminocarbonyl;

$R^8$ and $R^9$ are independently hydrogen, alkyl, substituted alkyl, aryl, substituted aryl, hydroxy, hydroxyalkyl, alkoxy, substituted alkoxy, alkoxyalkoxyalkyl halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, carboxy, alkoxycarbonyl, alkylcarbonyloxy, carbamoyl, alkenyl, substituted alkenyl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylcarbonylamino or alkylaminocarbonyl, or $R^8$ and $R^9$ are taken together with the atoms to which they are attached to form an optionally substituted carbobicyclic or heterobicyclic ring.

In another aspect of the invention, there are disclosed compounds of formula V

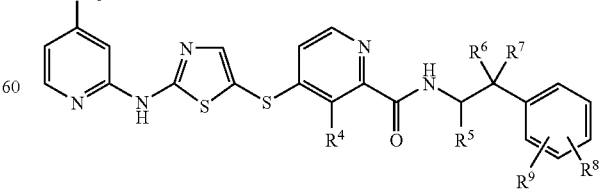

(V)

or a pharmaceutically acceptable salt or a stereoisomer thereof, wherein:

R⁴ is hydrogen, alkyl, substituted alkyl, hydroxy, cyano or halogen;

R⁵, R⁶ and R⁷ are independently hydrogen, alkyl, substituted alkyl, aryl, substituted aryl, hydroxy, hydroxyalkyl, alkoxy, substituted alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, disubstituted amino, amide, substituted amide, carbamate, substituted carbamate, ureido, cyano, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, carboxy, alkoxycarbonyl, alkylcarbonyloxy, carbamoyl, alkenyl, substituted alkynyl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylcarbonylamino or alkylaminocarbonyl;

R⁸ and R⁹ are independently hydrogen, alkyl, substituted alkyl, aryl, substituted aryl, hydroxy, hydroxyalkyl, alkoxy, substituted alkoxy, alkoxyalkoxyalkyl halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, carboxy, alkoxycarbonyl, alkylcarbonyloxy, carbamoyl, alkenyl, substituted alkenyl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylcarbonylamino or alkylaminocarbonyl, or R⁸ and R⁹ are taken together with the atoms to which they are attached to form an optionally substituted carbobicyclic or heterobicyclic ring.

Representative compounds of the invention include the following:

N-(2-hydroxy-2,2-diphenylethyl)-4-(2-(pyridin-2-ylamino)thiazol-5-ylthio)picolinamide;
N-(2-hydroxy-2-phenylpentyl)-4-(2-(pyridin-2-ylamino)thiazol-5-ylthio)picolinamide;
N-(2-hydroxy-2-(4-methylpyridin-2-yl)pentyl)-4-(2-(pyridin-2-ylamino)thiazol-5-ylthio)picolinamide;
3-fluoro-N-(2-hydroxy-2-phenylpentyl)-4-(2-(pyridin-2-ylamino)thiazol-5-ylthio)picolinamide;
(S)-3-fluoro-N-(2-hydroxy-2-phenylpentyl)-4-(2-(pyridin-2-ylamino)thiazol-5-ylthio)picolinamide;
(R)-3-fluoro-N-(2-hydroxy-2-phenylpentyl)-4-(2-(pyridin-2-ylamino)thiazol-5-ylthio)picolinamide;
3-fluoro-N-(2-hydroxy-2,2-diphenylethyl)-4-(2-(pyridin-2-ylamino)thiazol-5-ylthio)picolinamide;
N-(3-(dimethylamino)-2,2-diphenylpropyl)-3-fluoro-4-(2-(pyridin-2-ylamino)thiazol-5-ylthio)picolinamide;
3-fluoro-N-(2-hydroxy-2-(6-methylpyridin-2-yl)pentyl)-4-(2-(pyridin-2-ylamino)thiazol-5-ylthio)picolinamide;
3-fluoro-N-(2-hydroxy-2,2-diphenylethyl)-4-(2-(4-methylpyridin-2-ylamino)thiazol-5-ylthio)picolinamide;
N-(2,2-diphenylethyl)-3-fluoro-4-(2-(4-methylpyridin-2-ylamino)thiazol-5-ylthio)picolinamide;
3-fluoro-N-(3-((2-hydroxyethyl)(methyl)amino)-2,2-diphenylpropyl)-4-(2-(4-methylpyridin-2-ylamino)thiazol-5-ylthio)picolinamide;
3-fluoro-N-(3-((2-hydroxyethyl)(methyl)amino)-2,2-diphenylpropyl)-4-(2-(4-methylpyridin-2-ylamino)thiazol-5-ylthio)picolinamide;
(S)-3-Fluoro-N-(2-(2-(hydroxymethyl)phenyl)-2-phenylethyl)-4-(2-(pyridin-2-ylamino)thiazol-5-ylthio)picolinamide;
(R)-3-fluoro-N-(2-(2-(hydroxymethyl)phenyl)-2-phenylethyl)-4-(2-(pyridin-2-ylamino)thiazol-5-ylthio)picolinamide;
N-(3-(ethylamino)-2,2-diphenylpropyl)-3-fluoro-4-(2-(4-methylpyridin-2-ylamino)thiazol-5-ylthio)picolinamide;
4-(2-(5-((2-(dimethylamino)acetamido)methyl)pyridin-2-ylamino)thiazol-5-ylthio)-3-fluoro-N-(2-hydroxy-2-phenylpentyl)picolinamide;
3-fluoro-N-(2-hydroxy-2-phenylpentyl)-4-(2-(5-(methoxymethyl)pyridin-2-ylamino)thiazol-5-ylthio)picolinamide;
4-(2-(5-(1-(2-(dimethylamino)acetyl)piperidin-4-ylamino)pyridin-2-ylamino)thiazol-5-ylthio)-3-fluoro-N-(2-hydroxy-2-phenylpentyl)picolinamide;
(S)-3-fluoro-N-(2-hydroxy-2-phenylpentyl)-4-(2-(thieno[3,2-c]pyridin-4-ylamino)thiazol-5-ylthio)picolinamide;
3-fluoro-N-(2-(2-(hydroxymethyl)phenyl)-2-phenylethyl)-4-(2-(thieno[3,2-c]pyridin-4-ylamino)thiazol-5-ylthio)picolinamide; and
N-(2-hydroxy-2,2-diphenylethyl)-4-(2-(6-(4-(2-hydroxyethyl)piperazin-1-yl)-2-methylpyrimidin-4-ylamino)thiazol-5-ylthio)picolinamide, or pharmaceutically acceptable salts thereof.

The following are definitions of terms that may be used in the specification. The initial definition provided for a group or term herein applies to that group or term throughout the specification individually or as part of another group, unless otherwise indicated.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. Where noted above where the substituent is further substituted it will be with alkyl, alkoxy, aryl or arylalkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively.

The term "arylsulfonylaminocarbonyl" refers to an arylsulfonyl bonded to an aminocarbonyl.

The terms "aryloxyalkyl", "aryloxycarbonyl" or "aryloxyaryl" refer to an aryloxy bonded to an alkyl or substituted alkyl; a carbonyl; or an aryl or substituted aryl, respectively.

The term "arylalkyl" refers to an alkyl or substituted alkyl in which at least one of the hydrogen atoms bonded to at least one of the carbon atoms is replaced with an aryl or substituted aryl. Typical arylalkyls include, but are not limited to, for example, benzyl, 2-phenylethan-1-yl, 2-phenylethen-1-yl, naphthylmethyl, 2-naphthylethan-1-yl, 2-naphthylethen-1-yl, naphthobenzyl, and 2-naphthophenylethan-1-yl.

The term "arylalkyloxy" refers to an arylalkyl bonded through an oxygen linkage (—O-arylalkyl).

The term "substituted aryl" refers to an aryl group substituted by, for example, one to four substituents such as alkyl, substituted alkyl, alkenyl, substituted alkenyl, alkynyl, substituted alkynyl, aryl, substituted aryl, arylalkyl, halo, trifluoromethoxy, trifluoromethyl, hydroxy, alkoxy, alkanoyl, alkanoyloxy, aryloxy, arylalkyloxy, amino, alkylamino, arylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or arylalkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole, thiophene, indole or pyrimidine.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g. imidazolyl, furyl, thienyl, thiazolyl, pyrrolidyl, pyridyl, pyrimidyl and the like.

An "alkylidene" group refers to an alkylene group consisting of at least two carbon atoms and at least one carbon-carbon double bond.

The term "cycloalkyl" refers to an optionally substituted, saturated cyclic hydrocarbon ring systems, preferably containing 1 to 3 rings and 3 to 7 carbons per ring which may be further fused with an unsaturated $C_3$-$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclyl" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, homopiperazinyl, 2-oxohomopiperazinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include indolyl, 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, 1,3-benzodioxolyl, dihydrobenzofuryl, dihydrobenzothienyl, dihydrobenzothiopyranyl, dihydrobenzothiopyranyl sulfone, dihydrobenzopyranyl, indolinyl, indazolyl, isochromanyl, isoindolinyl, naphthyridinyl, phthalazinyl, piperonyl, purinyl, pyridopyridyl, pyrrolotriazinyl, quinazolinyl, tetrahydroquinolinyl, thienofuryl, thienopyridyl, thienothienyl, and the like.

Exemplary substituents include one or more alkyl or arylalkyl groups as described above or one or more groups described above as alkyl substituents.

Also included are smaller heterocyclyls, such as, epoxides and aziridines.

The term "carbocyclic ring" or "carbocyclyl" refers to stable, saturated, partially saturated or unsaturated, mono or bicyclic hydrocarbon rings that contain 3-12 atoms. Particularly, this includes a monocyclic ring containing 5 or 6 atoms or a bicyclic ring containing 9 or 10 atoms. Suitable values include cyclopropyl, cyclobutyl, cyclopentyl, cyclohexyl, cycloheptyl, dihydroindenyl and tetrahydronaphthyl. The term "optionally substituted" as it refers to "carbocyclic ring" or "carbocyclyl" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

The term "alkylsulfone" refers to $R^kS(=O)_2R^k$, wherein $R^k$ is an alkyl or substituted alkyl.

The term "oxo" refers to the divalent radical =O.

The term "carbamate" refers to the group —C(=O)NH$_2$.

The term "amide" refers to the group —C(=O)NH$_2$.

The term "sulfonamide" refers to the group —SO$_2$NH$_2$.

The terms "substituted amide", "substituted sulfonamide", or "substituted carbamate" refer to an amide, sulfonamide, or carbamate, respectively, having at least one hydrogen replaced with a group selected from alkyl, substituted alkyl, alkenyl, substituted alkenyl, cycloalkyl, and substituted cycloalkyl.

A substituted amide, for example, refers to the group —C(=O)NR$^m$R$^n$ wherein R$^m$ and R$^n$ are independently selected from H, alkyl, substituted alkyl, alkenyl, substituted alkenyl, cycloalkyl, and substituted cycloalkyl, provided at least one of R$^m$ or R$^n$ is a substituted moiety.

A substituted sulfonamide, for example, refers to the group —SO$_2$NR$^o$R$^p$ wherein R$^o$ and R$^p$ are independently selected from alkyl, substituted alkyl, alkenyl, substituted alkenyl, cycloalkyl, and substituted cycloalkyl, provided at least one of R$^o$ or R$^p$ is a substituted moiety.

A substituted carbamate, for example, refers to the group —C(=O)NR$^q$R$^r$ wherein R$^q$ and W are independently selected from alkyl, substituted alkyl, alkenyl, substituted alkenyl, cycloalkyl, and substituted cycloalkyl, provided at least one of R$^q$ or R$^r$ is a substituted moiety.

The term "ureido" refers to the group —NHC(=O)NH$_2$.

The term "cyano" refers to the group —CN.

The terms "cycloalkylalkyl" or "cycloalkylalkoxy" refer to a cycloalkyl or substituted cycloalkyl bonded to an alkyl or substituted alkyl; or an alkoxy, respectively.

The term "nitro" refers to the group —N(O)$_2$.

The term "thio" refers to the group —SH.

The term "alkylthio" refers to the group —SR$^s$ where R$^s$ is an alkyl, substituted alkyl, cycloalkyl, or substituted cycloalkyl.

The term "thioalkyl" refers to the group —R$^t$S where R$^t$ is an alkyl, substituted alkyl, cycloalkyl, or substituted cycloalkyl.

The term "alkylsulfonyl" refers to the group —S(=O)$_2$R$^u$ where R$^u$ is an alkyl, substituted alkyl, cycloalkyl, or substituted cycloalkyl.

The term "alkylsulfinyl" refers to the group —S(=O)R$^v$ where R$^v$ is an alkyl, substituted alkyl, cycloalkyl, or substituted cycloalkyl.

The term "carboxy" refers to the group —C(=O)OH.

The terms "carboxyalkoxy" or "alkoxycarbonylalkoxy" refer to a carboxy, or an alkoxycarbonyl, respectively, bonded to an alkoxy.

The term "alkoxycarbonyl" refers to the group —C(=O)OR$^w$ where R$^w$ is an alkyl, substituted alkyl, cycloalkyl, substituted cycloalkyl, aryl, substituted aryl, heteroaryl, or substituted heteroaryl.

The term "arylalkoxycarbonyl" refers to an aryl or substituted aryl bonded to an alkoxycarbonyl.

The terms "alkylcarbonyloxy" or "arylcarbonyloxy" refer to the group —OC(=O)R$^x$, where R$^x$ is an alkyl or substituted alkyl, or an aryl or substituted aryl, respectively.

The term "carbamoyl" refers to the groups —OC(=O)NH$_2$, —C(=O)NHR$^x$, and/or —C(=O)NR$^y$R$^z$, wherein R$^y$ and R$^z$ are independently selected from alkyl and substituted alkyl.

The term "carbonyl" refers to a C(=O).

The terms "alkylcarbonyl", "aminocarbonyl", "alkylaminocarbonyl" "aminoalkylcarbonyl", or "arylaminocarbonyl" refer to an alkyl or substituted alkyl; an amino; an alkylamino or substituted alkylamino; an aminoalkyl or substituted aminoalkyl; or an arylamino, respectively, bonded to a carbonyl.

The terms "aminocarbonylaryl" or "aminocarbonylalkyl" refer to an aminocarbonyl bonded to an aryl or substituted aryl; or an alkyl or substituted alkyl, respectively.

The term "sulfonyl" refers to the group S(=O)$_2$.

The term "sulfinyl" refers to an S(=O).

The term "carboxyalkyl" refers to an alkyl or substituted alkyl bonded to a carboxy.

The term "hydroxy" herein alone or as part of another group refers to —OH.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

It should further be understood that solvates (e.g., hydrates) of the compounds of formula I are also within the scope of the invention. Methods of solvation are generally known in the art.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the formula I may also have prodrug forms. Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 112, pp. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, 8, 1-38 (1992).

According to a further aspect of the invention, there is provided the use of a compound of the formula I, or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of formula I or a pharmaceutically acceptable salt thereof as defined herein before.

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, Zoladex; matrix metalloproteinase inhibitors; VEGF inhibitors, such as anti-VEGF antibodies (Avastin®) and small molecules such as Brivanib, ZD6474 and SU6668; Vatalanib, BAY-43-9006, SU11248, CP-547632, and CEP-7055; HER 1 and HER 2 inhibitors including anti-HER2 antibodies (Herceptin); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; Src inhibitors, e.g. Gleevec® and dasatinib; Casodex® (bicalutamide, Astra Zeneca), Tamoxifen; MEK-1 kinase inhibitors, MAPK kinase inhibitors, PI3 kinase inhibitors; PDGF inhibitors, such as imatinib; anti-angiogenic and antivascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0] heptadecane-5,9-dione (ixabepilone), [1S-[1R*,3R*(E), 7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione, and derivatives thereof; CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g. 6-thioguanine and 6-mercaptopurine; glutamine antagonists, e.g. DON (AT-125; d-oxo-norleucine); ribonucleotide reductase inhibitors; mTOR inhibitors; and haematopoietic growth factors.

Additional cytotoxic agents include cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein before may be surgery, radiotherapy or chemotherapy. Such chemotherapy may cover three main categories of therapeutic agent:

(i) antiangiogenic agents that work by different mechanisms from those defined herein before (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, exemestane), antihormones, antiprogestogens, antiandrogens (for example, flutamide, nilutamide, bicalutamide, cyproterone acetate), LHRH agonists and antagonists (for example, goserelin acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); intercalating antitumour antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide nitrosoureas, thiotepa; antimitotic agents (for example, vinca alkaloids like vincristine, vinorelbine, vinblastine and vinflunine) and taxoids such as Taxol® (paclitaxel), Taxotere® (docetaxel) and newer microbtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as Velcade® (bortezomib).

As stated above, the formula I compounds of the invention are of interest for their antiproliferative effects. Such compounds of the invention are expected to be useful in a wide range of disease states including cancer, psoriasis, and rheumatoid arthritis.

More specifically, the compounds of formula I are useful in the treatment of a variety of cancers, including (but not limited to) the following:

carcinoma, including that of the prostate, pancreatic ductal adreno-carcinoma, breast, colon, lung, ovary, pancreas, and thyroid;

tumors of the central and peripheral nervous system, including neuroblastoma, glioblastoma, and medulloblastoma; and other tumors, including melanoma and multiple myeloma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease.

The compounds of formula I are especially useful in treatment of tumors having a high incidence of tyrosine kinase activity, such as prostate, colon, brain, thyroid and pancreatic tumors. Additionally, the compounds of the invention may be useful in treatment of sarcomas and pediatric sarcomas. By the administration of a composition (or a combination) of the compounds of this invention, development of tumors in a mammalian host is reduced.

Compounds of formula I may also be useful in the treatment of other cancerous diseases (such as acute myelogenous leukemia) that may be associated with signal transduction pathways operating through kinases such as Flt-3 (Fine-like kinase-3), Tie-2, CDK2, VEGFR, FGFR and IGFR kinases.

The pharmaceutical compositions of the invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ Model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent(s).

If formulated as a fixed dose, a combination product can, for example, utilize a dosage of the compound of formula I within the dosage range described above and the dosage of another anti-cancer agent/treatment within the approved dosage range for such known anti-cancer agent/treatment. If a combination product is inappropriate, the compound of formula I and the other anti-cancer agent/treatment can, for example, be administered simultaneously or sequentially. If administered sequentially, the present invention is not limited to any particular sequence of administration. For example, compounds of formula I can be administered either prior to, or after, administration of the known anti-cancer agent or treatment.

The compounds may be administered in a dosage range of about 0.05 to 200 mg/kg/day, preferably less than 100 mg/kg/day, in a single dose or in 2 to 4 divided doses.

Biological Assays

A. CDK 2/Cyclin E Kinase Assay

The assays were performed in U-bottom 384-well plates. The final assay volume was 30 µl prepared from 15 µl additions of enzyme and substrates (fluoresceinated CDK2E substrate peptide and ATP) and test compounds in assay buffer (100 mM HEPES pH 7.4, 10 mM $MgCl_2$, 0.015% Brij35 and 4 mM DTT). The reaction was initiated by the combination of bacterially expressed, CDK2E with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 30 µM; FL-peptide, 1.5 µM; CDK2E, 0.2 nM; and DMSO, 1.6%. Dose response curves were generated to determine the concentration required to inhibit 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

B. FLT3

The assays were performed in U-bottom 384-well plates. The final assay volume was 30 µl prepared from 15 µl additions of enzyme and substrates (fluoresceinated FLT3 substrate peptide and ATP) and test compounds in assay buffer (100 mM HEPES pH 7.4, 10 mM $MgCl_2$, 0.015% Brij35 and 4 mM DTT). The reaction was initiated by the combination of FLT3 with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays are ATP, 200 FL-peptide, 1.5 FLT3, 4.5 nM and DMSO, 1.6%. Dose response curves were generated to determine the concentration required to inhibit 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

C. GSK3-β

The assays were performed in U-bottom 384-well plates. The final assay volume was 30 µl prepared from 15 µl additions of enzyme and substrates (fluoresceinated peptide FL-GSK substrate and ATP) and test compounds in assay buffer (100 mM HEPES pH 7.2, 10 mM $MgCl_2$, 0.015% Brij35, 25 mM 13-glycerolphosphate and 4 mM DTT). The reaction was initiated by the combination of GSK3-β with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 30 µM; FL-GSK substrate, 1.5 His-GSK3B, 2.4 nM; and DMSO, 1.6%.

D. IGF1-Receptor Tyrosine Kinase Assay

The assays were performed in U-bottom 384-well plates. The final assay volume was 30 µl prepared from 15 µl additions of enzyme and substrates (fluoresceinated IGF1R substrate peptide and ATP) and test compounds in assay buffer (100 mM HEPES pH 7.4, 10 mM $MnCl_2$, 0.015% Brij35 and 4 mM DTT). The reaction was initiated by the combination of IGF1-receptor with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 25 µM; FL-peptide, 1.5 µM; IGF1-Receptor, 14 nM; and DMSO, 1.6%. Dose response curves were generated to determine the concentration required to inhibit 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

Compounds described herein were tested in the above assay. The following results were obtained.

| Example# | IGF-1R IC50 (nM) |
| --- | --- |
| 36 | 2953 |
| 58 | 1518 |
| 56 | 891 |
| 49 | 886 |
| 33 | 693 |
| 83 | 394 |
| 64 | 316 |
| 67 | 288 |
| 63 | 250 |
| 55 | 199 |
| 69 | 5 |
| 77 | 4 |
| 52 | 3 |
| 82 | 3 |
| 65 | 1 |

E. Insulin Receptor Tyrosine Kinase Assay

The assays were performed in U-bottom 384-well plates. The final assay volume was 30 µl prepared from 15 µl additions of enzyme and substrates (fluoresceinated InsR substrate peptide and ATP) and test compounds in assay buffer (100 mM HEPES pH 7.4, 10 mM $MnCl_2$, 0.015% Brij35 and 4 mM DTT). The reaction was initiated by the combination of Insulin Receptor with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays are ATP, 25 µM; FL-peptide, 1.5 µM; Insulin Receptor, 14 nM; and DMSO, 1.6%. Dose response curves were generated to determine the concentration required to inhibit 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis

F. JAK2

The assays were performed in U-bottom 384-well plates. The final assay volume was 30 µl prepared from 15 µl additions of enzyme and substrates (fluoresceinated peptide FL-JAK2 substrate and ATP) and test compounds in assay buffer (100 mM HEPES pH 7.2, 10 mM $MgCl_2$, 0.015% Brij35, 25 mM β-glycerolphosphate and 4 mM DTT). The reaction was initiated by the combination of activated JAK2 with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 30 µM; FL-JAK2 peptide, 1.5 µM; His-CDK5/p25, 2.6 nM; and DMSO, 1.6%.

G. LCK Kinase Assay

The assays were performed in U-bottom 384-well plates. The final assay volume was 30 µl prepared from 15 µl additions of enzyme and substrates (fluoresceinated LCK substrate peptide and ATP) and test compounds in assay buffer (100 mM HEPES pH 7.4, 10 mM $MnCl_2$, 0.015% Brij35 and 4 mM DTT). The reaction was initiated by the combination of LCK with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 3 µM; FL-peptide, 1.5 µM; Lek, 1 nM; and DMSO, 1.6%. Dose response curves were generated to determine the concentration required to inhibit 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

H. MapKapK2

The assays were performed in U-bottom 384-well plates. The final assay volume was 30 µl prepared from 15 µl additions of enzyme and substrates (fluoresceinated MK2 substrate peptide and ATP) and test compounds in assay buffer (100 mM HEPES pH 7.4, 10 mM $MgCl_2$, 0.015% Brij35 and 4 mM DTT). The reaction was initiated by the combination of MapKapK2 with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays are ATP, 1 µM; FL-peptide, 1.5 µM; MapKapK2, 0.08 nM; Brij35, 0.015% and DMSO, 1.6%. Dose response curves were generated to determine the concentration required to inhibit 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

I. Met Kinase Assay

Kinase reactions consisted of 0.75 ng of baculovirus expressed GST-Met, 3 µg poly(Glu/Tyr) (Sigma), 0.12 µCi 33P γ-ATP, 1 µM ATP in 30 µl kinase buffer (20 mm TRIS-Cl, 5 mM $MnCl_2$, 0.1 mg/ml BSA, 0.5 mM DTT). Reactions were incubated for 1 h at 30° C. and stopped by the addition of cold trichloroacetic acid (TCA) to a final concentration 8%. TCA precipitates were collected onto GF/C unifilter plates using a Filtermate universal harvester and the filters were quantitated using a TopCount 96-well liquid scintillation counter. Dose response curves were generated to determine the concentration required to inhibit 50% of kinase activity ($IC_{50}$). Compounds were dissolved at 10 mM in dimethylsulfoxide (DMSO) and evaluated at seven concentrations, each in triplicate.

J. p38alpha Assay

The assays were performed in U-bottom 384-well plates. The final assay volume was 30 µl prepared from 15 µl additions of enzyme and substrates (fluoresceinated P38a substrate peptide and ATP) and test compounds in assay buffer (100 mM HEPES pH 7.2, 10 mM $MgCl_2$, 0.015% Brij35 and 4 mM DTT). The reaction was initiated by the combination of activated p38alpha with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 20 µM; FL-peptide, 1.5 µM; p38alpha, 6 nM; and DMSO, 1.6%.

K. p38beta Assay

The assays were performed in U-bottom 384-well plates. The final assay volume was 30 µl prepared from 15 µl additions of enzyme and substrates (fluoresceinated P38b substrate peptide and ATP) and test compounds in assay buffer (100 mM HEPES pH 7.2, 10 mM $MgCl_2$, 0.015% Brij35 and 4 mM DTT). The reaction was initiated by the combination of activated p38beta with substrates and test compounds. The reaction was incubated at room temperature for 60 min. and terminated by adding 30 µl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 20 µM; FL-peptide, 1.5 µM; p38beta, 1 nM; and DMSO, 1.6%.

L. Protein Kinase A

The assays were performed in U-bottom 384-well plates. The final assay volume was 30 µl prepared from 15 µl additions of enzyme and substrates (fluoresceinated PKA substrate peptide and ATP) and test compounds in assay buffer (100 mM HEPES pH 7.4, 10 mM $MgCl_2$, 0.015% Brij35 and 4 mM DTT). The reaction was initiated by the combination of Protein kinase A with substrates and test compounds. The reaction was incubated at room temperature for 60 min. and terminated by adding 30 μl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays are ATP, 20 μM; FL-peptide, 1.5 Protein kinase A 1 nM, and DMSO, 1.6%. Dose response curves were generated to determine the concentration required to inhibit 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

M. Protein Kinase C-alpha

The assays were performed in U-bottom 384-well plates. The final assay volume was 30 μl prepared from 15 μl additions of enzyme and substrates (fluoresceinated PKCa substrate peptide and ATP) and test compounds in assay buffer (100 mM HEPES pH 7.4, 10 mM $MgCl_2$, 0.015% Brij35 and 4 mM DTT). The reaction was initiated by the combination of Protein kinase C-alpha with lipids, substrates and test compounds. The reaction was incubated at room temperature for 60 min. and terminated by adding 30 μl of 35 mM EDTA to each sample. The reaction mixture was analyzed on the Caliper LabChip 3000 by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the assays is ATP, 1 μM; FL-peptide, 1.5 μM; Protein kinase C-alpha, 1 nM; and DMSO, 1.6%. Dose response curves were generated to determine the concentration required to inhibit 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

N. TrkA Kinase Assay

Kinase reactions consisted of 0.12 ng of baculovirus expressed His-TrkA, 3 μg poly(Glu/Tyr) (Sigma), 0.24 μCi 33P γ-ATP, 30 μM ATP in 30 μl kinase buffer (20 mm MOPS, 10 mM $MgCl_2$, 1 mM EDTA, 0.015% Brij-35, 0.1 mg/ml BSA, 0.0025% Beta-Mercaptoethanol). Reactions were incubated for 1 h at 30° C. and stopped by the addition of cold trichloroacetic acid (TCA) to a final concentration 8%. TCA precipitates were collected onto GF/C unifilter plates using a Filtermate universal harvester and the filters were quantitated using a TopCount 96-well liquid scintillation counter. Dose response curves were generated to determine the concentration required to inhibit 50% of kinase activity ($IC_{50}$). Compounds were dissolved at 10 mM in dimethylsulfoxide (DMSO) and evaluated at seven concentrations, each in triplicate.

O. TrkB Kinase Assay

Kinase reactions consisted of 0.75 ng of baculovirus expressed His-TrkB, 3 μg poly(Glu/Tyr) (Sigma), 0.24 μCi 33P γ-ATP, 30 μM ATP in 30 μl kinase buffer (20 mm MOPS, 10 mM $MgCl_2$, 1 mM EDTA, 0.015% Brij-35, 0.1 mg/ml BSA, 0.0025% Beta-Mercaptoethanol). Reactions were incubated for 1 h at 30° C. and stopped by the addition of cold trichloroacetic acid (TCA) to a final concentration 8%. TCA precipitates were collected onto GF/C unifilter plates using a Filtermate universal harvester and the filters were quantitated using a TopCount 96-well liquid scintillation counter. Dose response curves were generated to determine the concentration required to inhibit 50% of kinase activity ($IC_{50}$). Compounds were dissolved at 10 mM in dimethylsulfoxide (DMSO) and evaluated at seven concentrations, each in triplicate.

The instant compounds inhibit at least three of the following kinases: Flt-3, IGF1R, IR, JAK2, Met, TrkA or TrkB with $IC_{50}$ values between 0.001 to 1 μM. More preferred compounds have $IC_{50}$ values between 0.001 and 0.5 μM. Most preferred compounds have $IC_{50}$ values between 0.001-0.1 μM. Representative compounds are listed below:

3-Fluoro-N-(2-hydroxy-2-(6-methylpyridin-2-yl)pentyl)-4-(2-(pyridin-2-ylamino)thiazol-5-ylthio)picolinamide;

N-(2,2-diphenylethyl)-3-fluoro-4-(2-(pyridin-2-ylamino)thiazol-5-ylthio)picolinamide;

3-fluoro-N-(2-hydroxy-2,2-diphenylethyl)-4-(2-(4-methylpyridin-2-ylamino)thiazol-5-ylthio)picolinamide;

3-fluoro-N-(2-hydroxy-2-phenylpentyl)-4-(2-(5-(methoxymethyl)pyridin-2-ylamino)thiazol-5-ylthio)picolinamide;

N-(3-(ethylamino)-2,2-diphenylpropyl)-3-fluoro-4-(2-(4-methylpyridin-2-ylamino)thiazol-5-ylthio)picolinamide;

3-fluoro-N-(2-(2-(hydroxymethyl)phenyl)-2-phenylethyl)-4-(2-(pyridin-2-ylamino)thiazol-5-ylthio)picolinamide; and 4-(2-(5-(1-(2-(dimethylamino)acetyl)piperidin-4-ylamino)pyridin-2-ylamino)thiazol-4-ylthio)-N-(2-hydroxy-2-phenylpentyl)picolinamide.

Methods of Preparation

In general, the compounds of formula I can be prepared in accordance with Scheme I and the general knowledge of one skilled in the art. Tautomers and solvates (e.g., hydrates) of the compounds of formula I are also within the scope of the invention. Methods of solvation are generally known in the art. Accordingly, the compounds of the instant invention can be in the free or hydrate form, and can be obtained by methods exemplified in Scheme I.

The substituted aminothiazole intermediates VI may be prepared via a palladium-catalyzed reaction with a bromo- or chloro-heterocycle or heteroaromatic and 2-aminothiazole. These Buckwald/Hartwig type reactions are well-known to those skilled in the art and are performed in toluene, THF or dioxane and involve a palladium catalyst such as tris(dibenzylideneacetone)dipalladium (0), tetrakis(triphenylphsophine)palladium (0), palladium (II) acetate and the like, a base such as sodium or potassium carbonate or phosphate and a ligand such as XANTPHOS (9,9-dimethyl-4,5-bis(diphenylphosphino)xanthene. The same type of palladium-coupling reaction may be done with an amino-heterocycle or heteroaromatic and 2-chloro or 2-bromothiazole to give the same desired aminothiazole intermediates VI. In another approach, the substituted aminothiazole intermediates VI may be prepared by the heat-promoted displacement of various chloro- or bromo-heterocycles or heteroaromatics.

These substituted aminothiazole intermediates VI may be then further substituted to the corresponding bromides VIIb or thiocyanates VIIa by reaction with bromine in chloroform or by treatment with bromine and sodium or potassium thiocyanate in methanol.

Scheme I

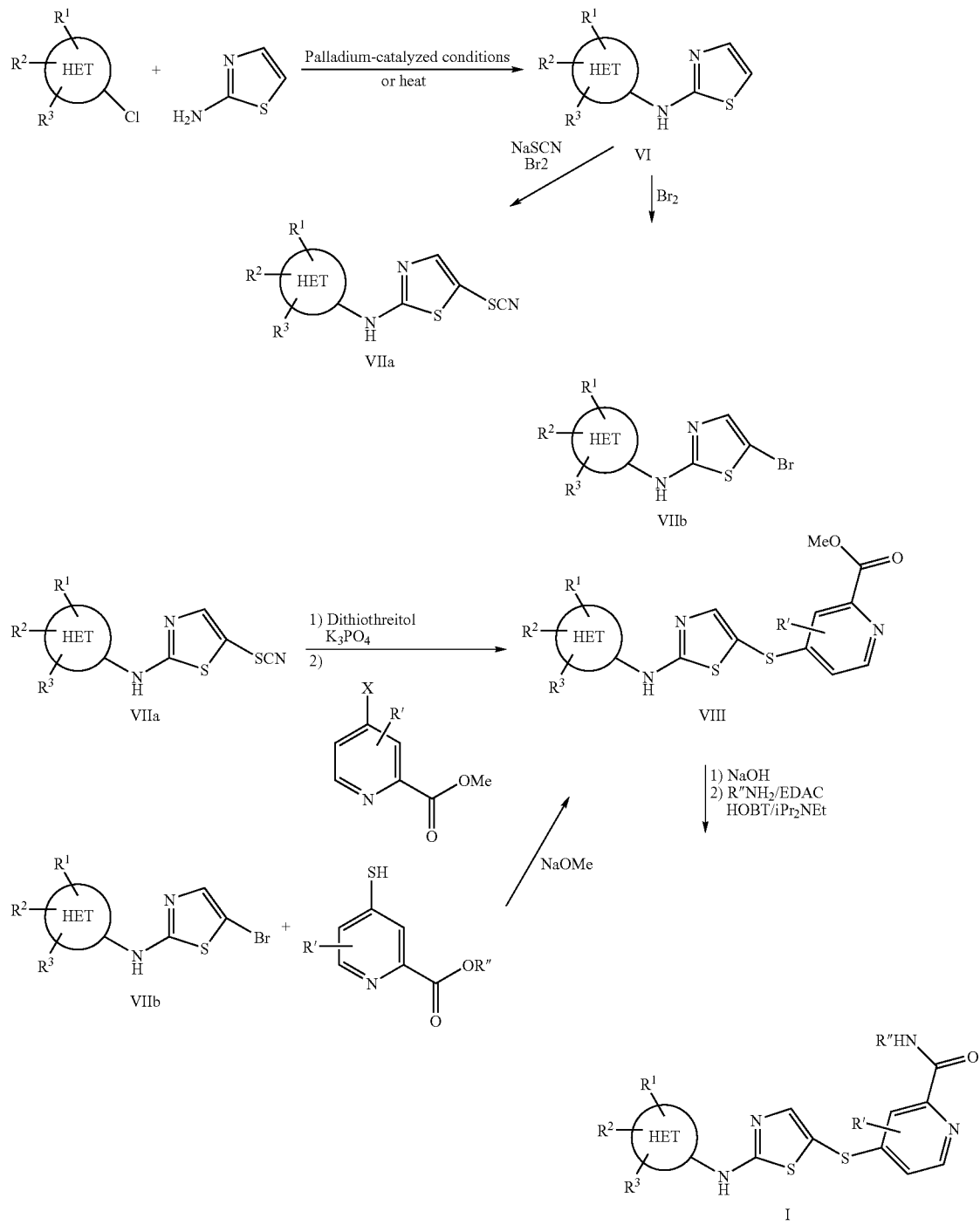

The bromides VIIb can then be substituted with various substituted thiopyridines bearing an ester or carboxylic acid in position 2 in presence of sodium methoxide in methanol. In another approach, the thiocyanates VIIa may first react with dithiothreitol in methanol and then with various substituted halopyridines bearing an ester or carboxylic acid in position 2 in presence of a base such as sodium hydroxide or potassium phosphate. The resulting ester intermediates VIII may then be saponified to the corresponding acids and coupled with various amines in presence of EDAC (1-[3-dimethylaminopropyl]-3-ethyl carbodiimide hydrochloride), hydroxybenzotriazole and a base such as diisopropylethylamine, triethylamine and the like to afford the compounds of type I.

The invention is further defined in the following Examples. It should be understood that these Examples are given by way of illustration only. From the above discussion and this Example, one skilled in the art can ascertain the essential characteristics of this invention, and without departing from the spirit and scope thereof, can make various changes and modifications to the invention to adapt the invention to various uses and conditions. As a result, the present invention is not limited by the illustrative examples set forth herein below, but rather defined by the claims appended hereto.

All temperatures are in degrees Celsius (° C.) unless indicated otherwise herein.

All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using silica gel (EMerck Kieselgel 60, 0.040-0.060 mm).

The following abbreviations may be employed herein: n-BuOH: n-butyl alcohol, CDCl$_3$: Chloroform-d, D$_2$O: deuterium oxide, DCM: dichloromethane, DMA: dimethylamine, DMF: dimethyl formamide, DMSO: dimethyl sulfoxide, EDC 1,2-dichloroethane, EtOH: ethanol, EtOAc: ethyl acetate, HCl: hydrochloric acid, HOAc: acetic acid, IPA: isopropyl alcohol, K$_2$CO$_3$: potassium carbonate, MeOH: methanol, MgSO$_4$: magnesium sulfate, NaHCO$_3$: sodium bicarbonate, Na$_2$SO$_4$: sodium sulfate, NH$_4$Cl: ammonium chloride, NH$_3$: ammonia, N$_2$: nitrogen, POCl$_3$: phosphorous oxychloride, THF: tetrahydrofuran, TFA: trifluoroacetic acid, Bn: benzyl, Me: methyl, Et: ethyl, min.: minute(s), h or hr(s): hour(s), L: liter, mL: milliliter, µL: microliter, g: gram(s), mg: milligram(s), mol.: moles, mmol: millimole(s), meq.: milliequivalent, RT or rt: room temperature, ret. t.: HPLC retention time (minutes), sat or sat'd: saturated, aq.: aqueous, TLC: thin layer chromatography, HPLC: high performance liquid chromatography, RP HPLC: reverse phase HPLC, Prep HPLC: preparative reverse phase HPLC, LC/MS: high performance liquid chromatography/mass spectrometry, MS: mass spectrometry, NMR: nuclear magnetic resonance, and mp: melting point, XANTPHOS: 9,9-dimethyl-4,5-bis(diphenylphosphino)xanthene, MeCN: acetonitrile, DMF: N,N-dimethylformamide, EDAC: 1-[3-dimethylaminopropyl]-3-ethyl carbodiimide hydrochloride, HOBT: 1-hydroxybenzotriazole hydrate, TMSCN: trimethylsilyl cyanide, LAH: lithium aluminum hydride, MOMCl: methoxymethyl chloride HPLC Conditions:

A: Primesphere C18, 4.6×30 mm, 2 min. gradient, 0% B to 100% B, Solvent A: 10% MeCN-90% water-0.1% TFA, Solvent B: 90% MeCN-10% water-0.1% TFA, 4 mL/min., 220 nM.

B: Primesphere C18, 4.6×30 mm, 2 min. gradient, 0% B to 100% B, Solvent A: 10% MeCN-90% water-5 mM NH$_4$OAc, Solvent B: 90% MeCN-10% water-5 mM NH$_4$OAc, 4 mL/min, 220 nM.

C: ZorbaxSB C18, 4.6×75 mm, 8 min. gradient, 0% B to 100% B, Solvent A: 10% MeCN-90% water-0.1% TFA, Solvent B: 90% MeCN-10% water-0.1% TFA, 2.5 mL/min, 220 nM.

D: Primesphere C18, 4.6×30 mm, 2 min. gradient, 0% B to 100% B, Solvent A: 10% MeCN-90% water-0.1% TFA, Solvent B: 90% MeCN-10% water-0.1% TFA, 4 mL/min, 254 nM.

E: Primesphere C18, 4.6×30 mm, 2 min. gradient, 0% B to 100% B, Solvent A: 10% MeCN-90% water-5 mM NH$_4$OAc, Solvent B: 90% MeCN-10% water-5 mM NH$_4$OAc, 4 mL/min, 254 nM.

G: Luna 5u C18, 4.6×30 mm, 2 min. gradient, 0% B to 100% B, Solvent A: 10% MeCN-90% water-0.1% TFA, Solvent B: 90% MeCN-10% water-0.1% TFA, 4 mL/min., 220 nM.

H: ZorbaxSB C18 4.6×75 mm, isocratic, 10% MeCN-90% water-5 mM NH$_4$OAc, 2.5 mL/min., 254 nM.

I: Luna 5u C18, 4.6×30 mm, 2 min. gradient, 0% B to 100% B, Solvent A: 10% MeCN-90% water-5 mM NH$_4$OAc, Solvent B: 90% MeCN-10% water-5 mM NH$_4$OAc, 4 mL/min, 254 nM.

J: Primesphere C18, 4.6×30 mm, 8 min. gradient, 0% B to 100% B, Solvent A: 10% MeCN-90% water-5 mM NH$_4$OAc, Solvent B: 90% MeCN-10% water-5 mM NH$_4$OAc, 4 mL/min, 254 nM.

K: ZorbaxSB C18 4.6×75 mm, 8 min gradient, 10% MeCN-90% water-5 mM NH$_4$OAc, 2.5 mL/min., 254 nM.

L: Luna 5u C18, 4.6×30 mm, 2 min. gradient, 0% B to 100% B, Solvent A: 10% MeCN-90% water-5 mM NH$_4$OAc, Solvent B: 90% MeCN-10% water-5 mM NH$_4$OAc, 4 mL/min, 220 nM.

M: Luna 5u C18, 4.6×30 mm, 2 min. gradient, 0% B to 100% B, Solvent A: 10% MeCN-90% water-0.1% TFA, Solvent B: 90% MeCN-10% water-0.1% TFA, 4 mL/min., 254 nM.

N: ZorbaxSB C18 4.6×75 mm, 8 min gradient, 10% MeCN-90% water-5 mM NH$_4$OAc, 2.5 mL/min., 220 nM.

O: ZorbaxSB C18, 4.6×75 mm, 8 min. gradient, 0% B to 100% B, Solvent A: 10% MeCN-90% water-0.1% TFA, Solvent B: 90% MeCN-10% water-0.1% TFA, 2.5 mL/min., 254 nM.

PREPARATION OF THE INTERMEDIATES

Thiazoles

A) Synthesis of N-(thiazol-2-yl)pyridine-2-amine

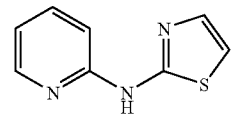

A suspension of 2-aminothiazole (7.35 g, 73.39 mmol), 2-chloropyridine (10.0 g, 88.07 mmol, 1.2 eq), sodium carbonate (10.98 g, 0.102 mol, 1.4 eq) and 9,9-dimethyl-4,5-bis (diphenylphosphino)xanthene (XANTPHOS) (0.509 g, 0.881 mmol, 0.012 eq) in toluene (160 mL, bubbled with argon for 5 minutes) was bubbled again with argon for 5 additional minutes. Tris(dibenzylideneacetone)dipalladium (0) (0.269 g, 0.293 mmol, 0.004 eq) was then added to the suspension which was heated at 140° C. for 4 days. The mixture was cooled down to RT and filtered. The resulting solid was suspended in water and this was stirred for 2 hours, after which, filtration of the suspension gave a light brown solid which was dried overnight under vacuum (10.329 g). The toluene filtrate was evaporated and the residue was triturated from methanol to give a solid (1.055 g). The two solids were combined and afforded the title compound (11.384 g, 87%). $^1$H NMR (400 MHz, DMSO-d6) δ (ppm): 6.91 (1H, dd, J=7.1, 5.1 and 0.8 Hz), 7.00 (1H, d, J=3.5 Hz), 7.06 (1H, d, J=8.3 Hz), 7.38 (1H, d, J=3.5 Hz), 7.69 (1H, ddd, J=8.3, 7.1 and 1.8 Hz), 8.29 (1H, ddd, J=5.1, 1.8 and 0.8 Hz), 11.24 (1H, s). LC/MS (M+H)+: 178. HPLC ret. time (Condition A): 0.668 min.

B) Synthesis of (6-(thiazol-2-ylamino)pyridine-3-yl)methanol

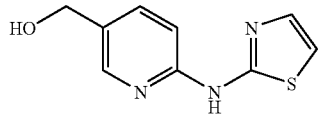

A suspension of (6-chloropyridin-3-yl)methanol (11.23 g, 78.22 mmol), 2-aminothiazole (9.40 g, 93.86 mmol, 1.2 eq), sodium carbonate (11.6 g, 109.5 mol, 1.4 eq) and XANTPHOS (0.543 g, 0.939 mmol, 0.012 eq) in THF (60 mL, bubbled with argon for 5 minutes) was bubbled again with argon for 5 additional minutes. Tris(dibenzylideneacetone)dipalladium (0) (0.269 g, 0.293 mmol, 0.004 eq) was then added to the suspension which was heated at 120° C. for 4 days. The mixture was cooled down to RT and filtered. The resulting solid was washed with toluene and tetrahydrofuran and suspended in water. This suspension was stirred for ~0.5 hour and then filtered. The resulting solid was dried overnight under vacuum to give the title material (15.072 g, 93%) as a solid. $^1$H NMR (400 MHz, DMSO-d6) δ (ppm): 4.44 (2H, d, J=5.6 Hz), 5.16 (1H, t, J=5.6 Hz), 6.98 (1H, d, J=3.7 Hz), 7.04 (1H, d, J=8.5 Hz), 7.37 (1H, d, J=3.6 Hz), 7.66 (1H, dd, J=8.5 and 2.2 Hz), 8.21 (1H, br d, J=1.5 Hz), 11.22 (1H, s). LC/MS (M+H)+: 208. HPLC ret. time (Condition A): 0.375 min.

C) Synthesis of 4-methyl-N-(thiazol-2-yl)pyridine-2-amine

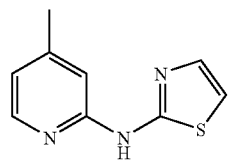

A suspension of 4-methyl-2-aminopyridine (5.10 g, 40.0 mmol), 2-aminothiazole (4.81 g, 48 mmol, 1.2 eq), sodium carbonate (5.94 g, 56.0 mmol, 1.4 eq) and XANTPHOS (0.278 g, 0.48 mmol, 0.012 eq) in THF (100 mL, bubbled with argon for 5 minutes) was bubbled again with argon for 5 additional minutes. Tris(dibenzylideneacetone)dipalladium (0) (0.146 g, 0.16 mmol, 0.004 eq) was then added to the suspension which was heated at 130° C. for 2 days. Additional quantities of XANTPHOS (0.278 g) and tris(dibenzylideneacetone)dipalladium (0) (0.146 g) were added again and the reaction was heated at 130° C. for 4 more days. The mixture was cooled down to RT and filtered. The resulting solid was suspended in water and stirred for 1 hour. After filtration, the resulting solid was dried under vacuum overnight. The THF filtrate was evaporated and the residue was combined to the previously isolated solid. This was precipitated from MeOH to give the title compound (5.14 g, 67%) as a solid. The mother liquor was evaporated and the residue purified by silica gel chromatography (50% ethyl acetate/dichloromethane to 100% ethyl acetate) and afforded the title material (0.825 g, 11%) as a solid, $^1$H NMR (400 MHz, CDCl3) δ (ppm): 2.36 (3H, s), 6.71 (1H, s), 6.75 (1H, br d, J=5.1 Hz), 6.84 (1H, d, J=3.5 Hz), 7.43 (1H, d, J=3.5 Hz), 8.24 (1H, d, J=5.3 Hz). LC/MS (M+H)+: 192. HPLC ret. time (Condition A): 1.285 min.

D) Synthesis of tert-butyl(6-(thiazolyl-2-ylamino)pyridine-3-yl)methylcarbamate

1. Synthesis of tert-butyl(6-chloropyridin-3-yl)methylcarbamate

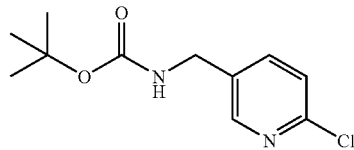

A stirred solution of (6-chloropyridin-3-yl)methanamine (6.56 g, 46.01 mmol) in dichloromethane (50 mL) was treated with triethylamine (11.2 mL, 80.51 mmol, 1.75 eq) and di-tent-butyl-di-carbonate (12.55 g, 57.51 mmol, 1.25 eq) at room temperature and this mixture was stirred overnight. Aqueous saturated ammonium chloride was added to the mixture and the two phases were separated. The aqueous phase was extracted with dichloromethane (3×) and the combined organic layers were dried over anhydrous magnesium sulfated, filtered and concentrated to give the title material (12.17 g, >100%) as a solid. $^1$H NMR (400 MHz, CDCl$_3$) δ (ppm): 1.47 (9H, s), 4.33 (1H, d, J=6.1 Hz), 4.95 (1H, br s), 7.32 (1H, d, 8.0 Hz), 7.64 (1H, br dd, J=7.8 and 1.5 Hz), 8.33 (1H, d, J=2.0 Hz). Traces of NEt$_3$HCl salt were detected by NMR. LC/MS (M+H)+: 243. The compound was used as such for the next reaction.

2. Synthesis of tert-butyl(6-(thiazolyl-2-ylamino)pyridine-3-yl)methylcarbamate

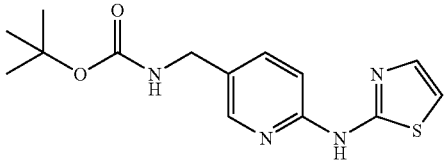

A suspension of tent-butyl(6-chloropyridin-3-yl)methylcarbamate (13.06 g, ~53.9 mmol, crude), 2-aminothiazole (8.10 g, 80.9 mmol, 1.5 eq), sodium carbonate (8.00 g, 75.5 mmol), XANTPHOS (0.374 g, 0.647 mmol, 0.012 eq) in THF (125 mL, bubbled with argon for 5 minutes) was bubbled again with argon for 5 additional minutes. Tris(dibenzylideneacetone)dipalladium (0) (0.198 g, 0.216 mmol, 0.004 eq) was then added to the suspension which was heated at 130° C. for 1 day. Additional quantities of XANTPHOS (0.374 g) and tris(dibenzylideneacetone)dipalladium (0) (0.198 g) were added again and the reaction was heated at 130° C. overnight. The mixture was cooled down to RT and filtered. The resulting solid was suspended in water and stirred for 1 hour. After filtration, the resulting solid was dried under vacuum overnight. The THF filtrate was evaporated and the residue was triturated from methanol to give a solid. The solids were combined to give the title material (13.91 g, 84%). $^1$H NMR (400 MHz, DMSO-d6) δ (ppm): 1.39 (9H, s), 4.06 (1H, d, J=6.1 Hz), 6.99 (1H, d, J=3.5 Hz), 7.02 (1H, d, J=8.6 Hz), 7.37 (1H, d, J=3.5 Hz), 7.39 (1H, br s), 7.58 (1H, dd, J=8.6 and 2.0 Hz), 8.15 (1H, br d, J~1.8 Hz), 11.21 (1H, s). LC/MS (M+H)$^+$: 307. HPLC ret. time (Condition A): 1.247 min.

E) Synthesis of 4-((tert-butyldimethylsilyloxy)methyl)-N-(thiazol-2-yl)pyridine-2-amine

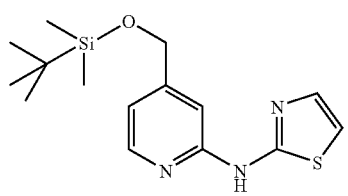

1. Synthesis of methyl 2-(thiazol-2-ylamino)isonicotinate

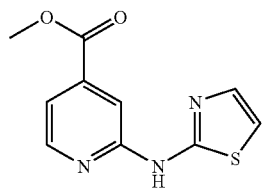

A suspension of methyl 2-chloroisonicotinate (15.0 g, 87.42 mmol), 2-aminothiazole (10.50 g, 104.9 mmol), sodium carbonate (12.97 g, 122.4 mmol, 1.4 eq) and XANTPHOS (0.607 g, 1.049 mmol, 0.012 eq) in toluene (300 mL, bubbled with argon for 5 minutes) was bubbled again with argon for 5 additional minutes. Tris(dibenzylideneacetone)dipalladium (0) (0.320 g, 0.349 mmol, 0.004 eq) was then added to the suspension which was heated at 100° C. for 5 days. The mixture was cooled down to RT and filtered. The resulting solid was suspended in water and stirred for 1 hour. After filtration, the resulting solid was dried under vacuum overnight and afforded the title material (14.17, 69%) as a solid. $^1$H NMR (400 MHz, DMSO-d6) δ (ppm): 3.90 (3H, s), 7.07 (1H, d, J=3.54), 7.32 (1H, dd, J=5.31, 1.26 Hz), 7.43 (1H, d, J=3.79 Hz), 7.61 (1H, s), 8.48 (1H, d, J=4.55 Hz), 11.56 (1H, s). LC/MS (M+H)$^+$: 236. HPLC ret. time (Condition A): 1.182 min.

2. Synthesis of 4-((tert-butyldimethylsilyloxy)methyl)-N-(thiazol-2-yl)pyridine-2-amine

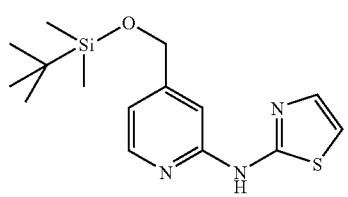

A stirred suspension of methyl 2-(thiazol-2-ylamino)isonicotinate (14.17 g, 60.23 mmol) in tetrahydrofuran (385 mL) was treated with lithium aluminum hydride (2.51 g, 66.25 mmol) at 23° C. The reaction was stirred at 23° C. for 1 hour then sodium hydroxide (5N, 20 mL) was added to the mixture which was stirred again for 2 more hours. The solid was filtered and washed with tetrahydrofuran and water. The combined washings and filtrate were concentrated to give the crude alcohol (11.17 g). The crude alcohol was dissolved in N,N-dimethylformamide (150 mL) and the resulting solution was treated with imidazole (6.60 g, 97.01 mmol) and tert-butyldimethylsilyl chloride (12.19 g, 80.84 mmol) at 23° C. The reaction was stirred for 1 hour, tert-butyldimethylsilyl chloride (6.0 g) was added again and the reaction stirred for 30 more minutes. N,N-Dimethylformamide was added and the residue was taken into dichloromethane/water/saturated ammonium chloride. The organic phase was separated and the aqueous phase was extracted with dichloromethane (3×). The combined organic layers were dried over anhydrous magnesium sulfate, filtered and concentrated. The residue was purified by silica gel chromatography (Biotage, 0% to 70% ethyl acetate in hexanes) to give the title material (10.55 g, 61% two steps). $^1$H NMR (400 MHz, CDCl$_3$) δ (ppm): 0.15 (6H, s), 0.98 (9H, s), 4.76 (2H, s), 6.81 (1H, br d, J=5.05 Hz), 6.84 (1H, d, J=3.54 Hz), 6.95 (1H, s), 7.48 (1H, d, J=3.54 Hz), 8.30 (1H, br d, J=5.31 Hz), 9.79 (1H, s). LC/MS (M+H)$^+$: 322. HPLC ret. time (Condition A): 1.800 min.

F) Synthesis of N-(5-nitropyridin-2-yl)thiazol-2-amine

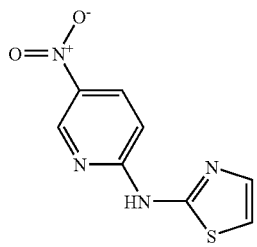

A solution of 2-chloro-5-nitropyridine (8.4 g, 53 mmol) and thiazol-2-amine (7.6 g, 76 mmol) in THF (250 mL) is cooled to 0° C. Sodium tert-butoxyde (30% w/w THF, 80 mL) is the added slowly over 15 minutes. The reaction mixture is then warmed slowly to room temperature and stirred 16 hours. The reaction mixture is then poured into a mixture of 1/1 ice/water (1.2 L) with stirring. The solid is filtered and air dried to give a powder (9.74 g, 83%). $^1$H NMR (400 MHz, DMSO-d6) δ (ppm): 7.17 (d, J=9.35 Hz, 2H), 7.20 (d, J=3.54 Hz, 1H), 7.49 (d, J=3.54 Hz, 1H), 8.43 (dd, J=9.35, 2.78 Hz, 1H), 9.15 (d, J=2.78 Hz, 1H), 12.17 (s, 1H). LCMS (M+H)$^+$: 223.

G) Synthesis of tert-butyl methyl((6-(thiazol-2-ylamino)pyridin-3-yl)methyl)carbamate

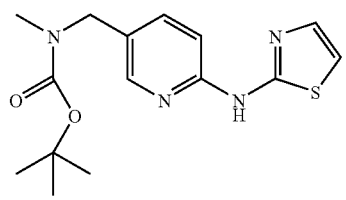

1. Synthesis of tert-butyl(6-chloropyridin-3-yl)methyl(methyl)carbamate

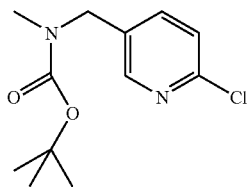

A solution of tert-butyl (6-(thiazolyl-2-ylamino)pyridine-3-yl)methylcarbamate (1.52 g crude, ~6.28 mmol) in THF (10 mL) was treated with sodium hydride (60% in oil, 0.360 g, 9.42 mmol) at 0° C. The reaction was then stirred at 23° C. for 45 minutes, then iodomethane (0.47 mL, 7.53 mmol) was added and the reaction was stirred overnight. Sat. aq ammonium chloride was then added and the two phases were separated. The aqueous phase was extracted with ethyl acetate (3×) and the combined organic layers were dried over anhydrous magnesium sulfate, filtered and concentrated to give the crude title material (1.50 g). The residue was purified on Biotage (hexane/ethylacetate 3:1 to 1:3) and gave the title material (1.24 g, 77%). $^1$H NMR (400 MHz, CDCl$_3$) δ ppm: 1.50 (9H, s) 2.86 (2H, d, J=19.70 Hz) 4.42 (s, 3H) 7.33 (1H, d, J=8.08 Hz) 7.57 (1H, d, J=17.94 Hz) 8.30 (1H, d, J=1.77 Hz). LCMS (M+H)$^+$: 257, 259. HPLC ret. time (Condition B): 1.743 min.

2. Synthesis of tert-butyl methyl((6-(thiazol-2-ylamino)pyridin-3-yl)methyl)carbamate

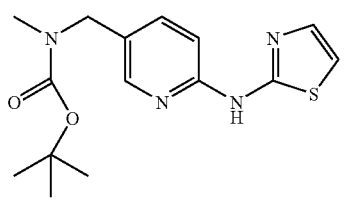

A suspension of 2-aminothiazole (0.556 g, 5.55 mmol, 1.15 eq), tert-butyl (6-chloropyridin-3-yl)methyl(methyl) carbamate (1.24 g, 4.83 mmol), sodium carbonate (0.717 g, 6.76 mol, 1.4 eq) and XANTPHOS (0.034 g, 0.058 mmol, 0.012 eq) in THF (12 mL, bubbled with argon for 5 minutes) was bubbled again with argon for 5 additional minutes. Tris (dibenzylideneacetone)dipalladium (0) (0.018 g, 0.019 mmol, 0.004 eq) was then added to the suspension which was heated at 130° C. for 18 hours. Tris(dibenzylideneacetone) dipalladium (0) (0.018 g, 0.019 mmol, 0.004 eq) and XANTPHOS (0.034 g, 0.058 mmol, 0.012 eq) were added again and the reaction was stirred for 18 more hours. The same was repeated a second time. The mixture was cooled down to RT and filtered. The THF filtrate was evaporated and the residue (1.72 g) was purified on Biotage silica gel chromatography (hexane/ethyl acetate 1:1 to 0:1) to give the title material (0.934 g, 60%). $^1$H NMR (400 MHz, CDCl$_3$) δ ppm: 1.52 (9H, s), 2.84 (3H, s), 4.40 (2H, s), 6.86 (1H, d, J=3.54 Hz), 6.92 (1H, d, J=8.59 Hz), 7.44 (1H, d, J=3.79 Hz), 7.57 (1H, d, J=19.45 Hz) 8.27 (1H, s).

H) Synthesis of N-(thiazol-2-yl)thieno[3,2-c]pyridin-4-amine

A flask charged with 4-chlorothieno[3,2-c]pyridine (New, James S. et al. J. Med. Chem., 32(6), p. 1147-1156 (1989)) (2.307 g, 13.6 mmol), 2-aminothiazole (1.67 g, 16.68 mmol), tris(dibenzylideneacetone)dipalladium (0) (0.225 g, 0.25 mmol), XANTPHOS (0.424 g, 0.73 mmol) and K$_3$PO$_4$ (4.08 g, 19.22 mmol) was purged with argon (3×). Dioxane (54 mL) was then added and the mixture was again purged with argon (5×). The reaction was heated to 100° C. with stirring under argon overnight. The reaction was then cooled to room temperature and gave a precipitate. This mixture was diluted with THF, filtered through Celite and washed with THF. SiO$_2$ was then added and the mixture was concentrated and purified on several Biotage silica gel chromatographies (5% to 100% ethyl acetate in hexane; 10% to 100% (2:1 dichloromethane: acetone) in dichloromethane; 10% to 100% (10% methanol in dichloromethane) in dichloromethane) to give the title material (1.97 g, 62%) as a solid. $^1$H NMR (400 MHz, DMSO-d$_6$) δ ppm: 11.59 (1H, s), 8.20 (1H, d, J=5.56 Hz), 8.13 (1H, d, J=5.81 Hz), 7.80 (1H, d, J=5.56 Hz), 7.60 (1H, d, J=5.56 Hz), 7.47 (1H, d, J=3.54 Hz), 7.07 (1H, d, J=3.79 Hz). LC/MS (M+H)$^+$: 234. HPLC ret. time (Condition I): 1.73 min.

I) Synthesis of N-(6-chloro-2-methylpyrimidin-4-yl)thiazol-2-amine

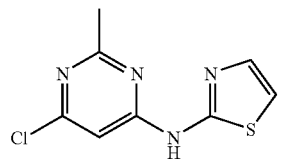

To a cool (0° C.), stirring suspension of 2-aminothiazole (3.05 g, 0.0305 mol), 4,6-dichloro-2-methylpyrimidine (5.84 g, 0.0358 mol) in THF (50 mL) was added dropwise over 10 minutes via addition funnel a solution of t-BuOK (40 mL, 30% wt in THF, 0.1069 mol). The reaction was allowed to slowly warm to room temperature overnight. To the reaction was added water (40 mL) and the resulting clear solution was extracted with chloroform and then chloroform/methanol (4:1). The combined extracts were concentrated to near dryness to give a precipitate. The solid was collected by filtration to give the title material (3.559 g) as a solid. The filtrate was concentrated to dryness and the resulting solid was dissolved in boiling methanol and allowed to precipitate overnight aided with the addition of some water. The solid was collected by filtration, washed with water and air dried to give the title material (1.451 g) as a solid. The aqueous layer from the extraction was acidified with 10% HCl and a precipitate was formed. The solid was collected by filtration, washed with water to give the title material (1.559 g) as a solid. The solids were combined to give the title material (6.569 g, 95%). $^1$H NMR (400 MHz, DMSO-$d_6$) δ (ppm): 2.53 (3H, s), 6.90 (1H, s), 7.21 (1H, d, J=3.5 Hz), 7.46 (1H, d, J=3.5 Hz), 11.87 (1H, s). LC/MS (M+H)$^+$: 227, 229. HPLC ret. time (Condition E): 1.427 min.

Bromides and Thiocyanates

A) Synthesis of 5-bromo-N-(pyridine-2-yl)thiazol-2-amine

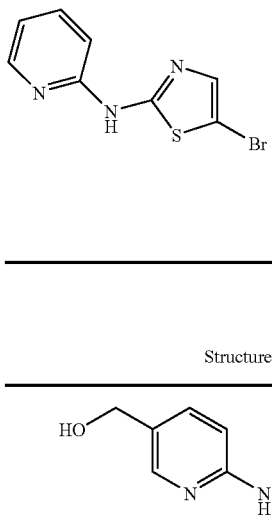

To a stirred suspension of N-(pyridin-2-yl)thiazol-2-amine (9.76 g, 55.07 mmol) in degassed chloroform (180 mL) was added bromine (3.11 mL, 60.6 mmol, 1.1 eq) at 23° C. The reaction was stirred for 15 minutes and followed by LC/MS. Bromine (2×0.3 mL) was added until reaction completed. The mixture was cooled down to 0° C. and 10% aq. NaHSO$_3$ (150 mL) was added. The suspension changed color and the solid was filtered, washed with water and vacuum dried overnight. The title compound was obtained as a solid (10.79 g, 77%). $^1$H NMR (400 MHz, DMSO-$d_6$) δ ppm 6.94-6.99 (1H, m), 7.04 (1H, d, J=8.34 Hz) 7.45 (1H, s), 7.74 (1H, td, J=7.83, 1.77 Hz), 8.31 (1H, d, J=5.31 Hz), 11.54 (1H, s). LC/MS (M+H)$^+$: 256, 258; (M−H)$^-$: 254, 256.

The bromides outlined in Table 1 were prepared according to the procedure described to prepare 5-bromo-N-(pyridine-2-yl)thiazol-2-amine

TABLE 1

| Structure | Name | LC/MS (M + H)$^+$ | Ret. Time (min.) | HPLC Condition |
| --- | --- | --- | --- | --- |
| 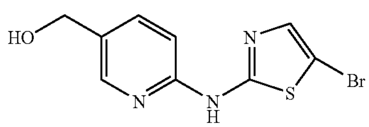 | (6-(5-Bromothiazolyl-2-ylamino)pyridine-3-yl)methanol | 286, 288 | 1.183 | A |
| 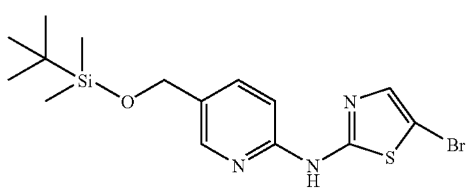 | 5-Bromo-N-(5-(tert-butyldimethylsilyloxy)methyl)pyridine-2-yl)thiazol-2-amine | 400, 402 | 2.523 | A |
| 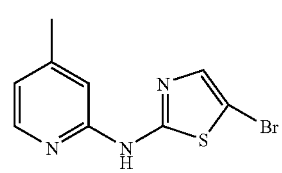 | 5-Bromo-N-(4-methyl-pyridine-2-yl)thiazol-2-amine | 270, 272 | 1.407 | A |
| 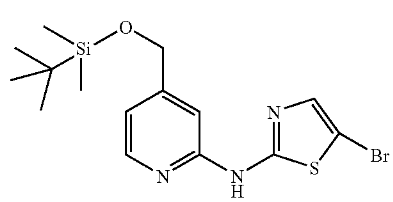 | 5-Bromo-N-(4-((tert-butyldimethylsilyloxy)methyl)pyridine-2-yl)thiazol-2-amine | 400, 402 | 2.398 | A |

B) Synthesis of N-(pyridin-2-yl)-5-thiocyanatothiazol-2-amine

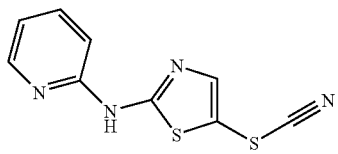

To a suspension of N-(pyridin-2-yl)thiazol-2-amine (4.26 g, 24 mmol) and sodium thiocyanate (3.9 g, 48 mmol, 2 eq) in methanol (100 mL) at 0° C., was slowly added bromine (1.23 mL, 24 mmol, 1 eq) over 2 min, then the temperature was raised to 23° C. and the mixture was stirred for 3 h. The resulting suspension was added to stirring cold water (400 mL) and the resulting precipitate was collected by filtration and vacuum dried (4.5 g, 80%). $^1$H NMR (400 MHz, DMSO-D6) δ ppm 7.00-7.08 (1H, m), 7.11 (1H, d, J=8.34 Hz), 7.74-7.84 (1H, m), 7.89 (1H, s), 8.39 (1H, d, J=5.05 Hz), 11.93 (1H, s). LC/MS (M+H)$^+$: 235.

C) Synthesis of N-(4-methylpyridin-2-yl)-5-thiocyanatothiazol-2-amine

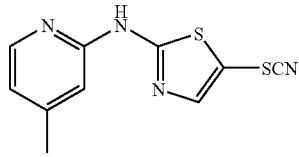

To a suspension of 4-methyl-N-(thiazol-2-yl)pyridine-2-amine (15.4 g, 80.5 mmol) and sodium thiocyanate (13.06, 161.05 mmol) in methanol (250 mL) was added dropwise bromine (4.55 mL, 88.57 mmol) over 20 min. The mixture was stirred at 23° C. After 1 h, HPLC shows complete conversion. The mixture was diluted with H$_2$O (700 mL) and concentrated on rotovap to remove the major part of the methanol. The resulting precipitate was collected by filtration and vacuum dried to give the title material (16.6 g, 100%). H$^1$ NMR (400 MHz, DMSO-d$_6$) δ (ppm): 2.31 (3H, s), 6.89 (1H, d, J=5.30 Hz), 6.91 (1H, s), 7.87 (1H, s), 8.24 (1H, d, J=5.05 Hz), 11.85 (1H, s). HPLC ret. time (Condition A): 1.585 min.

The thiocyanates shown in Table 2 were prepared according to the procedure described to prepare N-(pyridin-2-yl)-5-thiocyanatothiazol-2-amine or N-(4-methylpyridin-2-yl)-5-thiocyanatothiazol-2-amine (Examples B or C).

TABLE 2

| Structure | Name | LC/MS (M + H)$^+$ | Ret. Time (min.) | HPLC conditions |
|---|---|---|---|---|
| 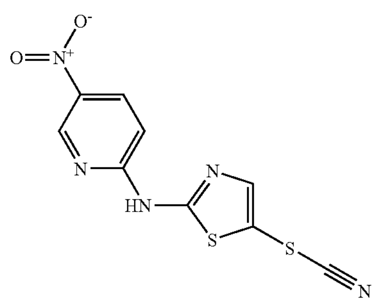 | N-(5-nitropyridin-2-yl)-4-thiocyanatothiazol-2-amine | 223 | 1.532 | B |
| 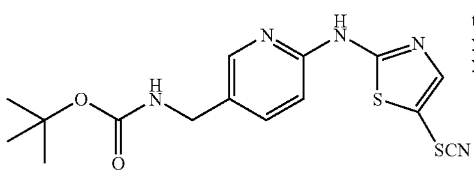 | tert-butyl (6-(5-thiocyanatothiazol-2-ylamino)pyridin-3-yl)methylcarbamate | 364 | 1.802 | B |
| 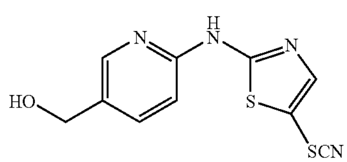 | (6-(5-thiocyanatothiazol-2-ylamino)pyridin-3-yl)methanol | 265 | 1.340 | B |
| 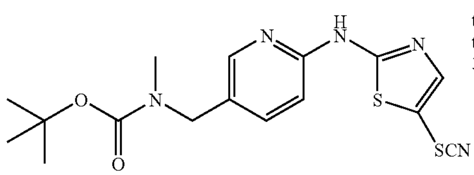 | tert-butyl methyl((6-(5-thiocyanatothiazol-2-ylamino)pyridin-3-yl)methyl)carbamate | 378 | 2.102 | A |

TABLE 2-continued

| Structure | Name | LC/MS (M + H)+ | Ret. Time (min.) | HPLC conditions |
|---|---|---|---|---|
| 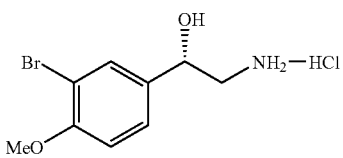 | N-(5-thiocyanatothiazol-2-yl)thieno[3,2-c]pyridin-4-amine | 291 | 1.94 | I |
| 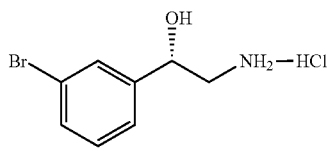 | N-(6-chloro-2-methylpyrimidin-4-yl)-5-thiocyanatothiazol-2-amine | 284, 286 | 1.637 | E |

Amines

A) Synthesis of (S)-2-amino-1-[3-bromo-4-methoxyphenyl]ethanol hydrochloride

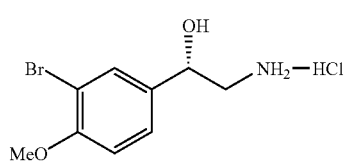

1. Synthesis of (S)-1-[4-methoxy-3-bromophenyl]-2-chloro ethanol

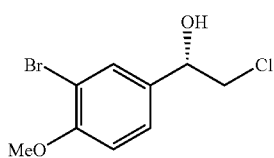

To a solution of (S)-Methyl-CBS-oxazaborolidine (1M in toluene, 0.745 mL, 0.745 mmol) and BH$_3$-THF (8 mL, 8 mmol) was added at the same time a solution of BH$_3$-THF (19 mL, 19 mmol) and a solution of the chloroketone (10.03 g, 37.98 mmol) in 19 mL of THF. Both solutions were added dropwise over 30 minutes. The solution was stirred for 1 hour and quenched with the slow addition of methanol (50 mL). The solution was concentrated and the residue chromatographed over a short silica gel column (1:1 hexane/ethyl acetate) to give a quantitative yield (10.0 g) of chlorohydrin as an oil. IR (KBr) 1053, 1258, 3406 cm$^{-1}$; $^1$H NMR (300 MHz, CDCl$_3$) δ 7.59 (s, 1H), 7.30 (dd, J=2.16 Hz, 1H), 6.90 (d, J=8.46 Hz, 1H), 4.83 (dd, J=3.57 Hz, 1H), 3.90 (s, 3H), 3.64 (ddd, J=3.6, 11.1, 8.7, 2H), 2.04 (b s, 1H). $^{13}$C NMR (CDCl$_3$, 75.5 MHz) δ 155.9, 133.5, 131.1, 126.3, 111.9, 73.1, 60.4, 56.3, 50.7.

2. Synthesis of (S)-2-amino-1-[3-bromo-4-methoxyphenyl]ethanol hydrochloride

To a solution of the chlorohydrin (10.0 g, 37.9 mmol) in 120 mL of methanol at −40° C. was added 100 grams of ammonia. The solution was sealed in a pressure bottle and warmed to ambient temperature and stirred for 48 hours. The solution was cooled and opened. The ammonia was allowed to evaporate and solution concentrated. The residue was crystallized from ethanol/ethyl acetate to give 3.83 g of a solid (35%). The material was reacted with Boc$_2$O in ethyl acetate and saturated sodium bicarbonate and analyzed by chiral HPLC using a chiralcel OJ column using 95% hexane/ethanol as elutant and determined to by 98% ee. Additional crops were collected −2.96 g and 1.41 g for a total of 75% yield. LRMS [M+H]+ 246; IR (cm$^{-1}$, KBr) 1055, 1261, 3001, 2948, 3356; $^1$H NMR (500 MHz, DMSO) δ 8.09 (b s, 2H), 7.58 (s, 1H), 7.36 (dd, J=2.05, 6.45 Hz, 1H), 7.11 (d, J=8.5 Hz, 1H) 6.10 (s, 1H), 4.80 (m, 1H), 3.84 (s, 3H), 3.00 (ddd, J=2.7, 12.6, 9.5 Hz, 2H); $^{13}$C NMR (DMSO, 75.5 MHz) δ 154.8, 135.4, 130.4, 126.6, 112.4, 110.4, 67.9, 56.2, 45.4.

B) Synthesis of (S)-2-amino-1-[3-bromophenyl]ethanol hydrochloride

The title material was prepared according to the general procedure outlined for the synthesis of (S)-2-amino-1-[3-chloro-4-methoxyphenyl]ethanol hydrochloride. LRMS [M+H]+ 217.9; IR (KBr, cm$^{-1}$) 3025, 3443, 2891; $^1$H NMR (500 MHz, DMSO-d$_6$) δ 7.93 (b s, 2H), 7.60 (s, 1H), 7.52 (d, 1H), 7.41 (s, 1H), 7.35 (d, J=7.7 Hz, 1H) 6.17 (s, 1H), 4.82 (m, 1H), 3.08 (ddd, J=2.6, 12.7, 9.6 Hz, 2H); $^{13}$C NMR (DMSO-d$_6$, 75.5 MHz) δ 144.4, 130.5, 128.7, 125.0, 121.6, 68.3, 45.1.

C) Synthesis of (S)-2-Amino-1-[3-chloro-4-methoxyphenyl]ethanol hydrochloride

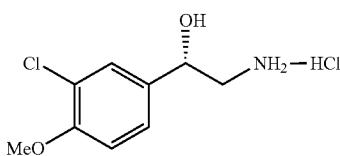

The title material was prepared according to the general procedure outlined for the synthesis of (S)-2-amino-1-[3-chloro-4-methoxyphenyl]ethanol hydrochloride. LRMS [M+H]+ 202; IR (KBr, cm$^{-1}$) 3354, 3003, 2949, 1288, 1064; $^1$H NMR (500 MHz, DMSO-d$_6$) δ 8.18 (brs, 3H), 7.43 (d, J=2.0 Hz, 1H), 7.31 (dd, J=8.5, 2.0 Hz, 1H), 7.14 (d, J=5.1 Hz, 1H), 6.11 (s, 1H), 4.81 (m, 1H), 3.84 (s, 3H), 2.99 (dd, J=13, 3.5 Hz, 1H), 2.83 (dd, J=12.5, 9 Hz, 1H); $^{13}$C NMR (DMSO-d$_6$, 125 MHz) δ 153.9, 135.0, 127.3, 125.8, 120.8, 112.6, 68.0, 56.1, 45.5; Elemental Analysis Calcd for C$_9$H$_{12}$ClNO$_2$—HCl: C, 45.39; H, 5.50; N, 5.88. Found: C, 45.38; H, 5.43; N, 5.70.

D) Synthesis of 2-amino-1,1-diphenylethanol

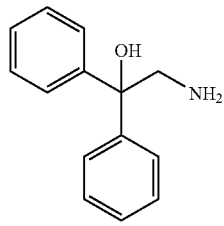

PhMgI was prepared by portionwise addition of PhI (1.45 mL, 12.85 mmol) in Et$_2$O (15 mL) to Mg (942 mg, 38.66 mmol) in Et$_2$O (5 mL). Once the reaction was completed, as evidenced by cessation of boiling, 2-aminoacetophenone•HCl (517.5 mg, 3.00 mmol) was added as a solid portionwise with stirring. Once addition was complete, the reaction was heated to reflux for 2.5 hr in a 40° C. water bath. The reaction was cooled to room temperature, ice was added followed by 50 mL of 10% aqueous HCl. The aqueous phase was extracted with ether and basified with NH$_4$OH. The organic phase was dried (MgSO$_4$), filtered and concentrated to afford 383.6 mg (60%) of the product as a solid: $^1$H NMR (400 MHz, CDCl$_3$) δ ppm 7.41-7.45 (m, 2H), 7.31 (t, J=7.45 Hz, 2H), 7.22 (t, J=7.33 Hz, 1H), 3.39 (s, 1H).

E) Synthesis of 1-amino-2-phenylpentan-2-ol

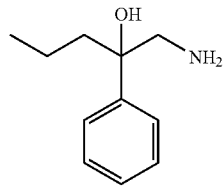

The title material was prepared according to the procedure to synthesize 2-amino-1,1-diphenylethanol (Example D). n-PrMgI (prepared from 1.20 mL of n-PrI and Mg (983 mg)) was added to stirring suspension of 2-aminoacetophenone•HCl (515 mg, 3.00 mmol). After workup, the title material was obtained (68.9 mg) as an oil: $^1$H NMR (400 MHz, CDCl$_3$) δ ppm 7.29-7.41 (m, 4H), 7.18-7.24 (m, 1H), 3.10 (d, J=12.88 Hz, 1H), 2.81 (d, J=12.38 Hz, 1H), 1.63-1.75 (m, 2H), 1.28-1.40 (m, 1H), 0.98-1.10 (m, 1H), 0.82 (t, J=7.33 Hz, 3H).

F) Synthesis of 1-amino-2-phenylbutan-2-ol

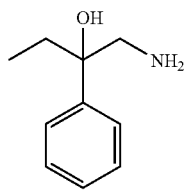

The title material was prepared according to the procedure to synthesize 2-amino-1,1-diphenylethanol (Example D). EtMgI (prepared from EtI (1.05 mL, 12.85 mmol) and Mg (944 mg)) was added to stirring suspension of 2-aminoacetophenone•HCl (514.5 mg, 3.00 mmol). After workup and HCl salt formation, the title material was obtained (195 mg) as a solid: $^1$H NMR (400 MHz, DMSO-d$_6$) δ ppm 7.71 (s, 2H), 7.43-7.46 (m, 2H), 7.33-7.41 (m, 2H), 7.27 (t, J=7.20 Hz, 1H), 3.04-3.14 (m, 2H), 1.73-1.81 (m, 2H), 0.59 (t, J=7.45 Hz, 3H).

G) Synthesis of 1-amino-4,4-dimethyl-2-phenylpentan-2-ol

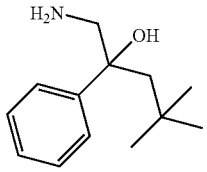

The title material was prepared according to the procedure to synthesize 2-amino-1,1-diphenylethanol (Example D). 2,2-Dimethylpropylmagnesium bromide (prepared from 2,2-dimethylpropylbromide (1.65 mL, 12.8 mmol) and Mg (942 mg)) was added to a stirring suspension of 2-aminoacetophenone•HCl (515 mg, 3.00 mmol). After workup, the title material was obtained (257 mg) as an oil, which was converted to the HCl salt to afford a solid (277 mg, 38%): $^1$H NMR (400 MHz, DMSO-d$_6$) δ ppm 8.20 (1H, d, J=6.82 Hz), 7.60-7.37 (4H, m), 3.08 (1H, dd, J=12.6, 5.8 Hz), 3.00 (1H, dd, J=12.6, 5.8 Hz), 1.85 (1H, d, J=14.4 Hz), 1.79 (1H, d, J=14.6 Hz), 0.64 (9H, s).

H) Synthesis of 2-amino-1-phenyl-1-(pyridin-2-yl)ethanol

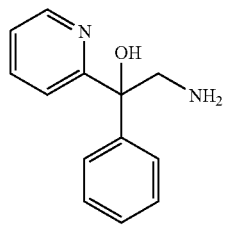

To a cold (−78° C.), stirred solution of 2-bromopyridine (0.38 mL, 4.0 mmol) in THF (40 mL) under Ar was added dropwise t-BuLi (5.2 mL, 8.8 mmol). After 30 min, 2-aminoacetophenone•HCl (687 mg, 4.00 mmol) was added as a solid in one portion. The reaction was allowed to slowly warm to RT as the bath warmed. Water was added and the reaction mixture was extracted with EtOAc, dried (MgSO$_4$), filtered and concentrated to afford a solid. Purification by flash chromatography afforded 68 mg as an oil: $^1$H NMR (400 MHz, CDCl$_3$) δ ppm 8.50 (d, J=4.80 Hz, 1H), 7.70-7.19 (m, 8H), 3.72 (d, J=13.14 Hz, 1H), 3.38 (d, J=13.14 Hz, 1H).

I) Synthesis of (S)-1-amino-2-phenylpentan-2-ol

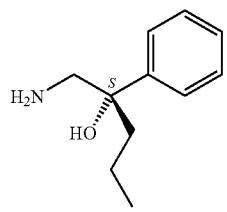

1. Synthesis of (2S)-2-phenyl-1-{[(1S)-1-phenylethyl]amino}pentan-2-ol and (2R)-2-phenyl-1-{[(1S)-1-phenylethyl]amino}pentan-2-ol

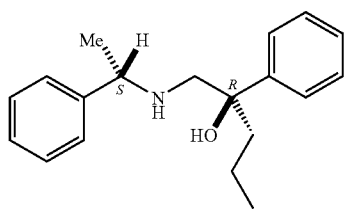

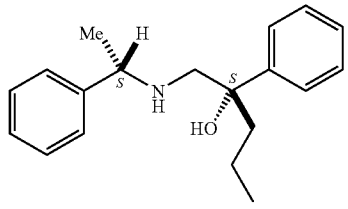

A solution of 2-bromoacetophenone (10.16 g, 51.05 mmol) in Et$_2$O (100 mL) was added to a cool (0° C.) stirring solution of S-(−)-α-methylbenzylamine (12.94 g, 106.8 mmol) in Et$_2$O (100 mL) in a flask equipped with a drying tube. The reaction was allowed to warm to RT overnight. The reaction was filtered and the solid washed with ether, and the filtrate cooled to −40° C. To the solution was added dropwise via addition funnel a solution of n-PrMgBr (prepared from n-PrBr (13.9 mL, 153 mmol), Mg (5.09 g, 209 mmol) in Et$_2$O (100 mL)) over 30 minutes. The reaction was allowed to warm to room temperature. After 5 hours, the reaction was poured onto ice, stirred until ice melted, then the phases were separated. The aqueous phase was extracted with EtOAc (2×), the combined organics were dried (MgSO4), filtered, concentrated and purified by flash chromatography (5-100% EtOAc in hexane) to afford the two diastereomers as oils:

(2S)-2-phenyl-1-{[(1S)-1-phenylethyl]amino}pentan-2-ol: 1.602 g (11%); $^1$H NMR (400 MHz, CDCl$_3$) δ ppm: 7.37-7.41 (2H, m), 7.28-7.36 (5H, m), 7.21-7.24 (3H, m), 3.65 (1H, q, J=6.57 Hz), 2.94 (1H, d, J=11.62 Hz), 2.63 (1H, d, J=11.62 Hz), 1.56-1.64 (2H, m), 1.21-1.30 (4H, m), 0.90 (1H, m), 0.75 (3H, t, J=7.20 Hz).

(2R)-2-phenyl-1-{[(1S)-1-phenylethyl]amino}pentan-2-ol: 2.264 g (16%); $^1$H NMR (400 MHz, CDCl$_3$) δ ppm: 7.27-7.36 (5H, m), 7.19-7.26 (3H, m), 7.08-7.13 (2H, m), 3.70 (1H, q, J=6.65 Hz), 2.90 (1H, d, J=11.62 Hz), 2.63 (1H, d, J=11.87 Hz), 1.59-1.66 (2H, m), 1.27-1.36 (4H, m), 1.00 (1H, m), 0.78 (3H, t, J=7.30 Hz).

2. Synthesis of (S)-1-amino-2-phenylpentan-2-ol

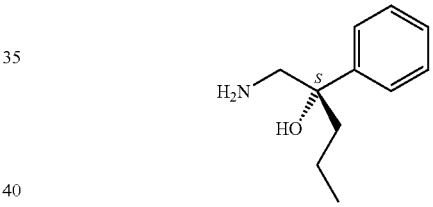

To a solution of (2S)-2-phenyl-1-{[(1S)-1-phenylethyl]amino}pentan-2-ol (0.954 g, 3.37 mmol) in EtOH (34 mL) was added Pd(OH)$_2$/C (10%, 644 mg), then stirred at room temperature under 1 atmosphere of H$_2$ overnight. The reaction was filtered through Celite, washed with EtOH, and the filtrate was concentrated to afford the desired product (609 mg, 100%) as an oil: $^1$H NMR (400 MHz, CDCl$_3$) δ ppm 7.35-7.40 (2H, m), 7.32 (2H, t, J=7.71 Hz), 7.21 (1H, t, J=7.20 Hz), 3.10 (1H, d, J=12.38 Hz), 2.86 (1H, d, J=12.63 Hz), 2.58 (3H, s), 1.65-1.76 (2H, m), 1.28-1.39 (1H, m), 0.96-1.07 (1H, m), 0.82 (3H, t, J=7.33 Hz); $[α]_D^{20°\,C.}$=+4.2° (c=1, EtOH).

J) Synthesis of (R)-1-amino-2-phenylpentan-2-ol

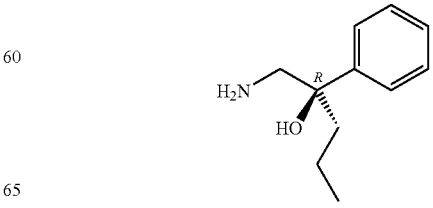

Following the same procedure used for the preparation of (S)-1-amino-2-phenylpentan-2-ol, (2R)-2-phenyl-1-{[(1S)-1-phenylethyl]amino}pentan-2-ol (1.364 g, 4.81 mmol) afforded the desired product (0.768 g, 89%) as an oil: $^1$H NMR (400 MHz, CDCl$_3$) δ ppm 7.36-7.41 (2H, m), 7.33 (2H, t, J=7.71 Hz), 7.18-7.24 (1H, m), 3.11 (1H, d, J=12.38 Hz), 2.84 (1H, d, J=12.38 Hz), 2.39 (3H, s), 1.64-1.74 (2H, m), 1.28-1.40 (1H, m), 0.97-1.08 (1H, m), 0.82 (3H, t, J=7.33 Hz); $[α]_D^{20° C.}$=−8.9° (c=1, EtOH).

K) Synthesis of 2-amino-1-(3-methoxyphenyl)ethanol

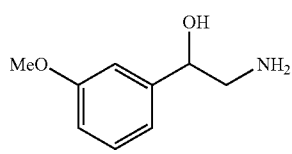

1. Synthesis of 2-nitro-1-(3-methoxyphenyl)ethanol

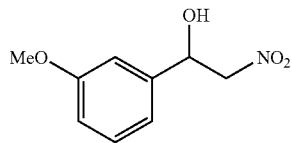

To a cool (0° C.), stirred solution of m-anisaldehyde (520 mg, 3.82 mmol) nitromethane (0.41 mL, 7.57 mmol) in MeOH (4 mL) was added over 5 seconds 10% NaOH (0.89 mL), stirred for 1 minute, then 2% HOAc (6.7 mL) was added. The reaction was stirred at 0° C. for 1 hour, was diluted with EtOAc, the organic layer was separated and washed with sat. NaHCO$_3$, brine and dried (MgSO4). Filtration and concentration afforded 688 mg of slightly impure 2-nitro-1-(3-methoxyphenyl)ethanol as an oil: $^1$H NMR (400 MHz, CD$_3$OD) δ ppm 7.27 (t, J=7.83 Hz, 1H), 6.97-7.01 (m, 2H), 6.86 (dd, J=7.83, 2.27 Hz, 1H), 5.35 (dd, J=9.85, 3.54 Hz, 1H), 4.67 (dd, J=12.63, 3.28 Hz, 1H), 4.54 (dd, J=12.63, 9.86 Hz, 1H), 3.79 (s, 3H).

2. Synthesis of 2-amino-1-(3-methoxyphenyl)ethanol

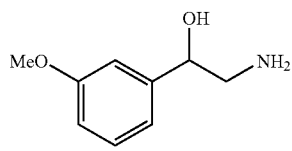

A suspension of 2-nitro-1-(3-methoxyphenyl)ethanol (688 mg, 3.49 mmol), PtO$_2$ (160 mg) in MeOH (10 mL) was pressurized to 40 psi H$_2$ and shaken in a Parr shaker overnight. The reaction was depressurized, filtered through Celite, concentrated, purified by flash chromatography (0-100% EtOAc: hexane) to afford 169 mg of the product as an oil: $^1$H NMR (400 MHz, CDCl$_3$) δ ppm 7.24 (t, J=7.96 Hz, 1H), 6.85-6.93 (m, 2H), 6.80 (m, 1H), 4.60 (dd, J=7.83, 4.04 Hz, 1H), 3.79 (s, 3H), 2.96 (dd, J=12.76, 3.92 Hz, 1H), 2.79 (dd, J=12.76, 7.71 Hz, 1H), 2.19 (s, 3H).

L) Synthesis of 1-amino-2-(pyridin-2-yl)pentan-2-ol

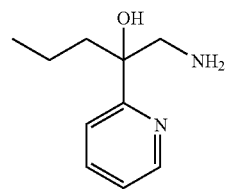

1. Synthesis of 1-(pyridin-2-yl)butan-1-one

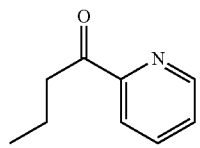

A solution of 2-cyanopyridine (2.20 g, 21.13 mmol) in Et$_2$O (35 mL) added over 10 min to a rapidly stirring solution of freshly prepared n-PrMgBr (from n-PrBr (2.71 g, 22.03 mmol) and Mg (0.62 g) in Et$_2$O (35 mL). Once addition was completed, the reaction was heated to reflux in a warm water bath for 2.5 hours. The reaction was cooled to RT then placed in ice, quenched with 5 mL H$_2$O followed by 60 mL 5N H$_2$SO$_4$. The ether phase was separated. The aqueous phase was heated in warm water for 15 minutes, then cooled in ice, basified with sat. K$_2$CO$_3$. The mixture was extracted with CHCl$_3$ and dried over K$_2$CO$_3$. The solution was filtered, concentrated and purified on Biotage Horizon (10-100% A=Hex, B=2:1 Hex:EtOAc) to afford 1.16 g of 1-(pyridin-2-yl)butan-1-one as an oil: $^1$H NMR (400 MHz, CDCl$_3$) δ ppm 8.67 (ddd, J=4.74, 1.71, 0.88 Hz, 1H), 8.03 (dt, J=7.83, 1.01 Hz, 1H), 7.82 (td, J=7.71, 1.77 Hz, 1H), 7.45 (ddd, J=7.52, 4.74, 1.14 Hz, 1H), 3.15-3.21 (m, 2H), 1.71-1.80 (m, J=7.43, 7.43, 7.43, 7.43, 7.43 Hz, 2H), 1.00 (t, J=7.33 Hz, 3H).

2. Synthesis of 1-amino-2-(pyridin-2-yl)pentan-2-ol

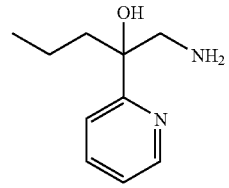

TMSCN (1.10 mL, 8.25 mmol) followed by ZnI$_2$ (163 mg, 0.51 mmol) were sequentially added to neat 1-(pyridin-2-yl)butan-1-one (1.131 g, 7.58 mmol) with stirring under Ar. The reaction was stirred at RT for 1 hour. THF (13 mL) was added to cyanohydrin, then this was slowly added dropwise over 10 min via cannula to LAH (462 mg, 12.17 mmol) in THF (30 mL) with stirring under Ar. The reaction warmed as addition progressed. Once the addition ended, the reaction was heated to reflux for 1 hour, then cooled to RT then cooled in ice. To the cooled reaction mixture was added with stirring Na$_2$SO$_4$.10H$_2$O. The reaction stirred overnight and was allowed to warm to RT as the bath warmed. The reaction was filtered, solid washed with EtOAc, the organic phase extracted with 10% HCl (2×), aqueous extracts combined and washed with Et$_2$0. The aqueous phase was basified to pH ~12 with 5M NaOH, saturated with NaCl, and then extracted with Et$_2$O (3×). Combined extracts were dried (MgSO$_4$), filtered and concentrated to afford 695 mg of 1-amino-2-(pyridin-2-yl)pentan-2-ol as an oil. $^1$H NMR showed this to be a 1:1.6 mixture of ROTMS:ROH:$^1$H NMR for desired product: $^1$H NMR (400 MHz, CDCl$_3$) δ ppm 8.53 (m, 1H), 7.64 (td, J=7.58, 1.77 Hz, 1H), 7.58 (dt, J=7.83, 1.14 Hz, 1H), 7.10 (ddd, J=7.33, 4.80, 1.26 Hz, 1H), 3.32 (d, J=13.64 Hz, 1H), 2.87 (d, J=13.64 Hz, 1H), 0.75 (m, 3H)

M) Synthesis of 1-amino-2-(pyridin-2-yl)propan-2-ol

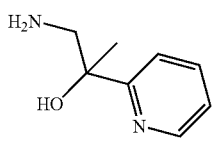

1. Preparation of 2-hydroxy-2-(pyridin-2-yl)propanenitrile

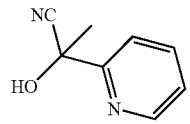

To a stirring solution of 2-acetylpyridine (500 mg, 4.128 mmol), ZnI$_2$ (64 mg, 0.201 mmol) in THF (20 mL) was added TMSCN (0.61 mL, 4.57 mmol), then the reaction was heated to 70° C. After 2.5 h, the reaction was cooled to RT, HCl (10 mL, 3M in water) was added with vigorous stirring for 2 h. The reaction was partitioned between H$_2$O and Et$_2$O; the ethereal phase was separated, washed with brine, dried over MgSO$_4$, filtered and concentrated to afford the desired product (92 mg) as an oil: $^1$H NMR (400 MHz, CDCl$_3$) δ ppm 8.56-8.61 (1H, m), 7.87 (1H, td, J=7.71, 1.77 Hz), 7.59 (1H, dt, J=8.08, 1.01 Hz), 7.40 (1H, ddd, J=7.58, 4.80, 1.01 Hz), 1.91 (4H, s).

2. Preparation of 1-amino-2-(pyridin-2-yl)propan-2-ol

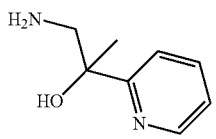

To a cool (0° C.), stirring solution of LiAlH$_4$ (57 mg, 1.502 mmol) in THF (5 mL) was added dropwise via cannula a solution of 2-hydroxy-2-(pyridin-2-yl)propanenitrile (92 mg, 0.621 mmol) in THF (5 mL). After 1 h at 0° C., powdered Na$_2$SO$_4$.10H$_2$O was added and the reaction was allowed to warm to RT until the colour dissipated. The solid was removed by filtration. The filtrate was concentrated to afford the product (65 mg) as an oil: $^1$H NMR (400 MHz, MeOD) δ ppm: 8.44 (1H, d, J=4.04 Hz), 7.76-7.86 (1H, m), 7.69 (1H, d, J=8.08 Hz), 7.21-7.30 (1H, m), 3.04 (1H, d, J=13.39 Hz), 2.86 (1H, d, J=13.14 Hz), 1.39 (3H, s).

N) Synthesis of 1-amino-2-(4-methylpyridin-2-yl)pentan-2-ol

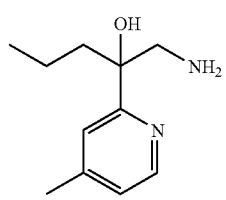

1. Synthesis of 1-(4-methylpyridin-2-yl)butan-1-one

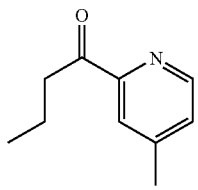

A solution of 2-cyano-4-methylpyridine (526 mg, 4.45 mmol) in Et$_2$O (10 mL) added over 10 min to a rapidly stirring solution of freshly prepared n-PrMgBr (from n-PrBr (0.40 mL, 4.45 mmol) and Mg (132 mg) in Et$_2$O (10 mL). Once addition was completed, the reaction was heated to reflux in a warm water bath for 2 hours. The reaction was cooled to RT then cooled in ice, quenched with 1 mL H$_2$O then 13 mL 5N H$_2$SO$_4$. The ether phase was separated. The aqueous phase was heated in warm water for 15 minutes, then cooled in ice and basified with sat. K$_2$CO$_3$. The solution was extracted with CHCl$_3$ and dried over K$_2$CO$_3$. The solution was filtered and concentrated to afford 372 mg of 1-(4-methylpyridin-2-yl)butan-1-one as an oil: $^1$H NMR (400 MHz, CDCl$_3$) δ ppm 8.51 (d, J=4.80 Hz, 1H), 7.85 (s, 1H), 7.27 (s, 1H), 3.17 (t, J=7.45 Hz, 2H), 2.41 (s, 3H), 1.69-1.79 (m, J=7.43, 7.43, 7.43, 7.43, 7.43 Hz, 2H), 0.99 (t, J=7.45 Hz, 4H).

2. Synthesis of 1-amino-2-(4-methylpyridin-2-yl)pentan-2-ol

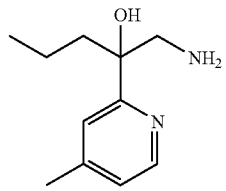

TMSCN (0.3 mL, 2.28 mmol) followed by $ZnI_2$ (51 mg, 0.16 mmol) were sequentially added to neat 1-(4-methylpyridin-2-yl)butan-1-one (372 mg, 2.28 mmol) with stirring under Ar. Reaction stirred at rt for 4 hours. THF (6 mL) was added to cyanohydrin, then this was slowly added dropwise over 10 min via cannula to LAH (140 mg, 3.6 mmol) in THF (10 mL) with stirring under Ar. Reaction warmed as addition progressed. Once addition was ended, reaction heated to reflux for 1 hour, then cooled to rt then in ice. To the cool reaction with stirring was added $Na_2SO_4.10H_2O$, the reaction stirred overnight and was allowed to warm to RT as the bath warmed. The reaction was filtered, the solid washed with EtOAc; the organic phase extracted with 10% HCl (2×). The aqueous extracts were combined and washed with $Et_2O$. Aqueous phase was basified to pH ~12 with 5M NaOH, saturated with NaCl, then extracted with $Et_2O$ (3×). The combined extracts were dried ($MgSO_4$), filtered and concentrated to afford 330 mg of 1-amino-2-(4-methylpyridin-2-yl)pentan-2-ol as an oil. $^1H$ NMR (400 MHz, $CDCl_3$) δ ppm 8.36 (d, J=5.05 Hz, 1H), 7.18 (s, 1H), 7.00 (d, J=5.81 Hz, 1H), 3.04 (d, J=12.88 Hz, 1H), 2.90 (d, J=12.88 Hz, 1H), 2.37 (s, 3H), 1.71 (m, 2H), 1.40 (m, 1H), 0.77-0.95 (m, 4H).

O) Synthesis of 1-amino-2-(6-methylpyridin-2-yl)pentan-2-ol

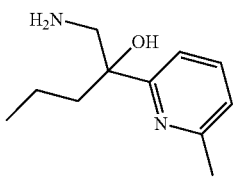

The title material was prepared as described for the synthesis of 1-amino-2-(4-methylpyridin-2-yl)pentan-2-ol (Example L) in using 6-methylpicolinonitrile and propyl magnesium bromide. LC/MS (M+H)$^+$: 195. HPLC ret. time (Condition E): 1.068 min.

P) Synthesis of 3-amino-2,2-diphenylpropan-1-ol

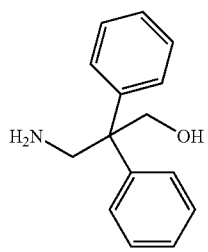

1. Preparation of 3-hydroxy-2,2-diphenylpropanenitrile

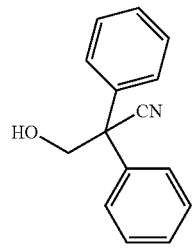

To a suspension of 2,2-diphenylacetonitrile (2.0 g, 10.35 mmol) and paraformaldehyde (1.242 g, 41.399 mmol) in pyridine (18 mL) was added Triton B (40% solution in water, 1.022 mL, 2.587 mmol) at 0° C. The suspension instantaneously changed color. The cooling bath was removed and the reaction was stirred at 23° C. for ~40 hours. The reaction was then acidified with acetic acid (2 mL) and poured into water (150 mL). The aqueous phase was extracted with diethyl ether (2×) and the combined organic extracts were washed with water (2×), 1N HCl (2×) and saturated sodium bicarbonate. The organic phase was dried over anhydrous magnesium sulfate, filtered and concentrated. The residue was purified on silica gel Biotage chromatography (ethyl acetate/hexane 10% to 50%) to give the title material (1.83 g, 100%) as an oil. HPLC ret. time (Condition A): 1.682 min. $^1H$ NMR (400 MHz, $CDCl_3$) δ ppm: 2.21 (1H, t, J=7.20 Hz), 4.37 (2H, d, J=6.82 Hz), 7.35-7.44 (10H, m).

2. Preparation of 3-amino-2,2-diphenylpropan-1-ol

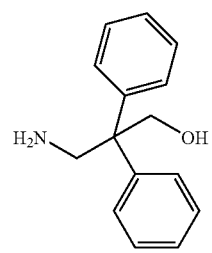

A solution of 3-hydroxy-2,2-diphenylpropanenitrile in tetrahydrofuran (50 mL) was slowly added dropwise to a suspension of LAH in tetrahydrofuran (20 mL) at 23° C. The reaction was stirred overnight, then quenched with sodium sulfate decahydrate. The resulting solid was removed by filtration and the filtrate was concentrated to dryness to give the title material (0.45 g, 88%) as an oil which was used as such for the next reaction. $^1H$ NMR (400 MHz, $CDCl_3$) δ ppm: 2.49 (2H, s), 3.77 (1H, ddd, J=6.63, 4.23 and 2.53 Hz), 3.82 (2H, s), 4.30 (2H, s), 7.25-7.36 (10H, m). LC/MS (M+H)$^+$: 228. HPLC ret. time (Condition A): 1.228 min.

Q) Synthesis of $N^1,N^1$-diethyl-2,2-diphenylpropane-1,3-diamine

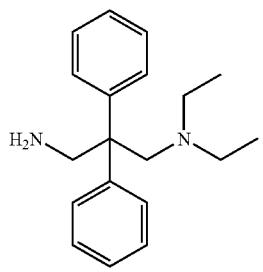

1. Preparation of 3-(diethylamino)-2,2-diphenylpropanenitrile

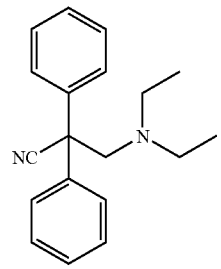

A mixture of 2,2-diphenylacetonitrile (0.5 g, 2.59 mmol), paraformaldehyde (0.155 g, 5.17 mmol) and diethylamine (1.07 mL, 10.35 mmol) in N,N-dimethylformamide (2 mL) was heated in a microwave oven at 100° C. for 1 hour. The reaction was then diluted with aqueous hydrochloric acid (1N) and washed with ethyl acetate. The aqueous phase was then basified with saturated aqueous sodium carbonate and this was extracted with ethyl acetate. The combined organic layers were dried over anhydrous magnesium sulfate, filtered and concentrated to give the title material (0.627 g, 87%) as an oil. LC/MS (M+H)$^+$: 279. HPLC ret. time (Condition B): 2.378 min. $^1$H NMR (400 MHz, CDCl$_3$) δ ppm: 0.87 (6H, t, J=7.07 Hz), 2.47 (4H, q, J=7.07 Hz), 3.44 (2H, s) 7.28-7.39 (6H, m) 7.41-7.46 (4H, m).

2. Preparation of N$^1$,N$^1$-diethyl-2,2-diphenylpropane-1,3-diamine

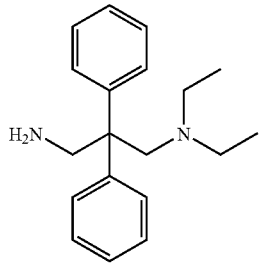

A solution of 3-(diethylamino)-2,2-diphenylpropanenitrile (0.627 g, 2.25 mmol) in diethyl ether (5 mL) was slowly added to a suspension of lithium aluminum hydride (0.171 g, 4.50 mmol) in diethyl ether (5 mL) at 0° C. The resulting slurry was stirred at 0° C. for 1.5 hours. The reaction was then quenched by adding sodium sulphate decahydrate and stirring for 30 minutes. The reaction was then diluted with ethyl acetate and celite was added. The suspension was filtered and the filtrate was concentrated to dryness to give the title material (0.511 g, 80%) as an oil. LC/MS (M+H)$^+$: 283. HPLC ret. time (Condition B): 1.602 min. $^1$H NMR (400 MHz, CDCl$_3$) δ ppm: 0.81 (6H, t, J=7.07 Hz), 2.19 (4H, q, J=7.07 Hz), 3.18 (2H, s), 3.51 (2H, s) 7.16-7.20 (6H, m) 7.24-7.32 (4H, m).

R) Synthesis of N$^1$,N$^1$-dimethyl-2,2-diphenylpropane-1,3-diamine

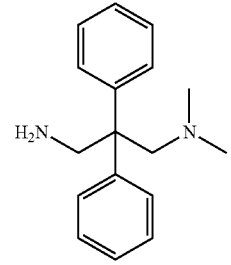

The title material was prepared as described for the synthesis of N$^1$,N$^1$-diethyl-2,2-diphenylpropane-1,3-diamine (Example Q) in using 2-(methylamino)ethanol. LC/MS (M+H)$^+$: 255. HPLC ret. time (Condition B): 1.300 min. $^1$H NMR (400 MHz, CDCl$_3$) δ ppm: 1.98 (6H, s), 3.12 (2H, s), 3.54 (2H, s), 7.19-7.22 (6H, m), 7.28-7.31 (4H, m).

S) Synthesis of 2-((3-amino-2,2-diphenylpropyl)(methyl)amino)ethanol

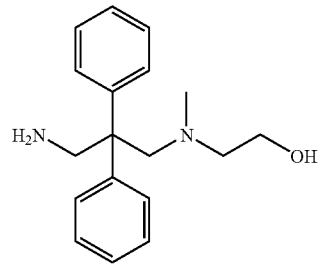

The title material was prepared as described for the synthesis of N$^1$,N$^1$-diethyl-2,2-diphenylpropane-1,3-diamine (Example Q) in using 2-(methylamino)ethanol. LC/MS (M+H)$^+$: 285. HPLC ret. time (Condition B): 1.405 min.

T) Synthesis of N$^1$-(2-methoxyethyl)-N$^1$-methyl-2,2-diphenylpropane-1,3-diamine

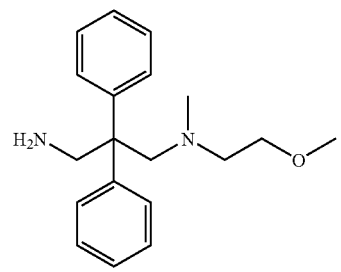

The title material was prepared as described for the synthesis of N$^1$,N$^1$-diethyl-2,2-diphenylpropane-1,3-diamine (Example Q) in using 2-methoxy-N-methylethanamine LC/MS (M+H)+: 299. HPLC ret. time (Condition B): 1.480 min.

U) Synthesis of N¹-tert-butyl-2,2-diphenylpropane-1,3-diamine

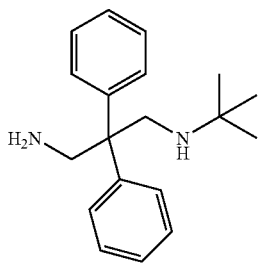

The title material was prepared as described for the synthesis of N¹,N¹-diethyl-2,2-diphenylpropane-1,3-diamine (Example Q) in using tert-butylamine LC/MS (M+H)+: 283. HPLC ret. time (Condition B): 2.202 min.

V) Synthesis of 2-(2-((methoxymethoxy)methyl)phenyl)-2-phenylethanamine

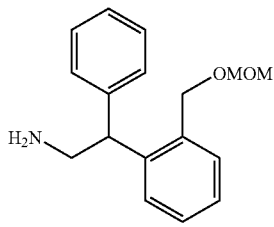

1. Preparation of 1-iodo-2-((methoxymethoxy)methyl)benzene

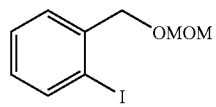

To stirring solution of 2-iodobenzyl alcohol (6.02 g, 25.72 mmol) in dichloromethane (40 mL) was added sequentially Hunig's base (6.8 mL, 38.51 mmol) followed by MOMCl (3.0 mL, 39.13 mmol), and stirred at 23° C. overnight. The reaction was treated with saturated NH$_4$Cl (30 mL), stirred vigorously for several minutes, then the phases separated. The organic phase was extracted with dichloromethane (2×). The combined organics were dried (MgSO$_4$), filtered and concentrated to an amber oil which was purified on Biotage Horizon (10-100% (7:3 hexane:EtOAc)/hexane, 40+M, SiO$_2$) to afford the product (6.06 g) as an oil: ¹H NMR (400 MHz, CDCl$_3$) δ ppm 7.83 (dd, J=7.83, 1.26 Hz, 1H), 7.45 (dd, J=7.70, 1.64 Hz, 1H), 7.35 (td, J=7.52, 1.14 Hz, 1H), 6.99 (td, J=7.58, 1.77 Hz, 1H), 4.76 (s, 2H), 4.59 (s, 2H), 3.43 (s, 3H).

2. Preparation of 1-((methoxymethoxy)methyl)-2-(2-nitro-1-phenylethyl)benzene

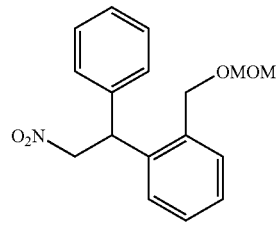

To a stirring solution of 1-iodo-2-((methoxymethoxy)methyl)benzene (4.51 g, 16.22 mmol) in THF (40 mL) under argon was added dropwise a solution of i-PrMgBr (9.5 mL, 2.12M in Et$_2$O, 20.14 mmol) via syringe. The stirring was maintained at 0° C. After 1 hour, a solution of nitrostyrene (2.014 g, 13.50 mmol) in THF (40 mL) was added via cannula over 10 minutes and the stirring was maintained at 0° C. After 30 minutes, the reaction was quenched with saturated NH$_4$Cl and extracted with EtOAc (2×). The combined extracts were dried (MgSO$_4$), filtered and concentrated to an oil which was purified on Biotage Horizon (10-50% EtOAc:hexane, SiO$_2$, 40+M) to afford the product (2.93 g) as an oil: ¹H NMR (400 MHz, CDCl$_3$) δ ppm 7.35-7.39 (m, 1H), 7.27-7.34 (m, 3H), 7.22-7.27 (m, 5H), 5.34 (t, J=8.08 Hz, 1H), 4.94-5.03 (m, 2H), 4.73 (d, J=11.87 Hz, 1H), 4.68 (q, J=6.57 Hz, 2H), 4.57 (d, J=11.87 Hz, 1H), 3.42 (s, 3H).

3. Preparation of 2-(2-((methoxymethoxy)methyl)phenyl)-2-phenylethanamine

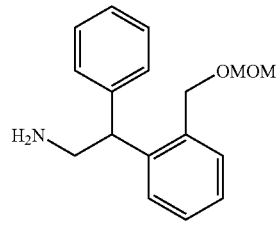

Raney nickel (3.4 g) was placed in Parr flask and was washed with MeOH (3×), then 1-((methoxymethoxy)methyl)-2-(2-nitro-1-phenylethyl)benzene (2.93 g, 9.72 mmol) in MeOH (150 mL) was added. The flask was installed on a Parr shaker, purged first with argon (3×) then H$_2$ (3×) then pressurized to ~35 psi and shaken over a weekend. The reaction was depressurized, then was filtered and concentrated to give 3.22 g of an oil. The residue was dissolved in CHCl$_3$, dried (MgSO$_4$), filtered through Celite and concentrated to afford the product (2.57 g) as an oil: ¹H NMR (400 MHz, CDCl$_3$) δ ppm 7.35 (s, 4H), 7.13-7.31 (m, 5H), 4.70 (d, J=11.87 Hz, 3H), 4.66 (s, 3H), 4.51 (d, J=11.62 Hz, 2H), 4.35 (t, J=6.06 Hz, 1H), 3.39 (s, 3H).

W) Synthesis of 2-(3-((methoxymethoxy)methyl)phenyl)-2-phenylethanamine

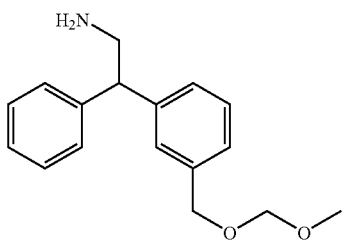

The title material was prepared as described for the synthesis of 2-(2-((methoxymethoxy)methyl)phenyl)-2-phenylethanamine (Example V) in using 3-iodobenzyl alcohol. LC/MS (M+H)+: 272. HPLC ret. time (Condition A): 1.213 min.

X) Synthesis of 2-(4-((methoxymethoxy)methyl)phenyl)-2-phenylethanamine

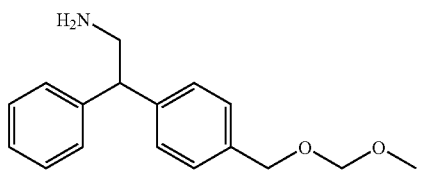

The title material was prepared as described for the synthesis of 2-(2-((methoxymethoxy)methyl)phenyl)-2-phenylethanamine (Example V) in using 4-iodobenzyl alcohol. LC/MS (M+H)+: 272. HPLC ret. time (Condition B): 1.248 min.

Y) Synthesis of (1-phenylcyclopropyl)methanamine

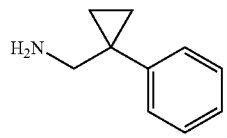

1. Preparation of 1-phenylcyclopropanecarboxamide

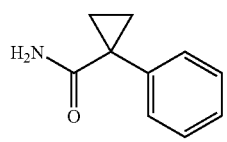

Thionyl chloride (0.225 mL, 3.08 mmol) was slowly added to a solution of 1-phenylcyclopropanecarboxylic acid (0.50 g, 3.08 mmol) in toluene (10 mL) and DMF (0.3 mL). The reaction was then heated at reflux for 2 hours, then cooled down to 23° C. and treated (slow addition) with a solution of ammonia (2M in methanol, 10 mL). The reaction was then stirred at 23° C. overnight. The reaction was then diluted with hydrochloric acid (1N) and extracted with ethyl acetate (3×). The combined organic layers were dried over anhydrous magnesium sulfate, filtered and concentrated to give the crude title material (0.474 g, 95%) as a solid which was used as such in the next reaction. $^1$H NMR (400 MHz, CDCl$_3$) δ: 1.11 (2H, q, J=3.79 Hz), 1.60-1.66 (2H, m), 5.34 (1H, br s), 5.91 (1H, br s), 7.31-7.41 (3H, m), 7.43-7.47 (2H, m). HPLC ret. time (Condition B): 1.225 min.

2. Preparation of (1-phenylcyclopropyl)methanamine

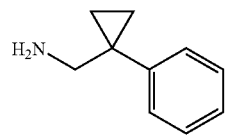

A solution of 1-phenylcyclopropanecarboxamide (0.450 g, 2.79 mmol) in tetrahydrofuran (5 mL) was slowly added to a suspension of LAH (0.117 g, 3.07 mmol) in tetrahydrofuran (5 mL) at 23° C. over 2 minutes. The reaction was then heated to 65° C. for 6 hours. The reaction was quenched with the Rochelle salt (1N in water, 10 mL) and extracted with ethyl acetate (3×). The combined organic layers were then dried over anhydrous magnesium sulfate, filtered and concentrated to give the crude title material (0.200 g, 49%) as an oil which was used as such in the next reaction. An aliquot was purified on preparative HPLC (ammonium acetate/water/acetonitrile). $^1$H NMR (400 MHz, CDCl$_3$, acetic acid salt) δ: 0.83-0.94 (4H, m), 1.98 (3H, s), 2.90 (2H, s), 4.98 (3H, br s), 7.23-7.37 (5H, m).

Z) Synthesis of 2-amino-1,1-dim-tolylethanol

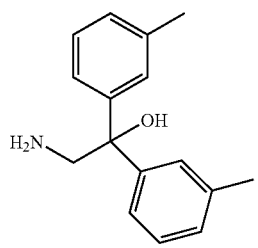

1. Preparation of benzyl 2-hydroxy-2,2-dim-tolylethylcarbamate

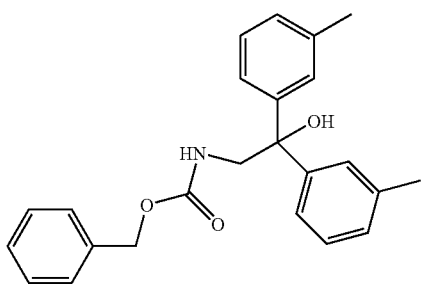

3-Bromotoluene (0.8 mL, 6.6 mmol) was added to Mg turnings (0.312 g, 13 mmol) in diethyl ether (5 mL) and an iodine crystal was also added. The reaction was stirred for 30 minutes. The solution was then transferred to another flask (via a pipet) to separate from the excess Mg. A solution of carbobenzyloxyglycine methyl ester (0.294 g, 1.32 mmol) in diethyl ether (3 mL) was then added to the solution of the Grignard reagent and the reaction was stirred for 1 hour. The reaction was then quenched with sat. aq ammonium chloride and the aqueous phase was extracted with ethyl acetate (3×). The combined organic layers were dried over anhydrous magnesium sulfate, filtered and concentrated. The residue was purified on Biotage chromatography (10% to 10% ethyl acetate/hexane) to give the title material (0.309 g, 62%) as an oil. $^1$H NMR (400 MHz, DMSO-d6) δ: 2.26 (6H, s), 3.82 (2H, d, J=5.81 Hz), 4.99 (2H, s), 5.76 (1H, s), 6.79 (1H, t, J=5.56 Hz), 7.01 (2H, d, J=7.07 Hz), 7.09-7.40 (11H, m). LC/MS (M−H)$^-$: 374. HPLC ret. time (Condition B): 2.133 min.

2. Preparation of 2-amino-1,1-dim-tolylethanol

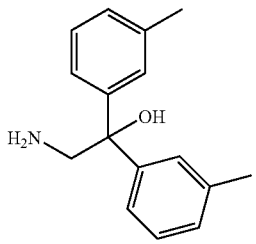

Benzyl 2-hydroxy-2,2-dim-tolylethylcarbamate (0.309 g, 0.823 mmol) was dissolved in ethanol (6 mL) and treated with 5% Pd/C (~20 mgs). The reaction was stirred overnight under a hydrogen atmosphere (balloon). The reaction was filtered and the residue was purified on Biotage chromatography (10% to 60% methanol/dichloromethane) to give the title material (0.119 g, 60%) as an oil. $^1$H NMR (400 MHz, DMSO-d6) δ: 2.24 (6H, s), 3.16 (2H, ddd, J=3.16, 1.77 and 1.64 Hz), 4.27 (2H, s), 6.96 (2H, d, J=7.07 Hz), 7.15 (4H, m), 7.23 (2H, br s). LC/MS (M+H)$^+$: 242. HPLC ret. time (Condition B): 1.328 min.

AA) Synthesis of 2-methoxy-2,2-diphenylethanamine

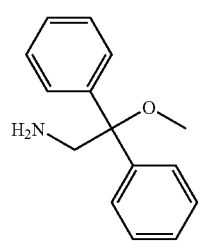

1. Preparation of tert-butyl 2-hydroxy-2,2-diphenylethylcarbamate

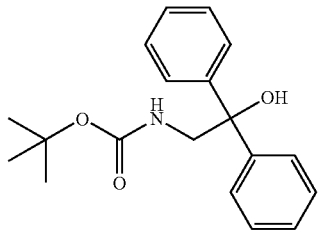

To a solution of carbo-tert-butyloxyglycine methyl ester (0.50 g, 2.6 mmol) in dry tetrahydrofuran (10 mL) was slowly added phenylmagnesium bromide (1M in THF, 7.9 mL, 7.9 mmol) and the reaction was stirred at 23° C. for 3 hours. Water was added and the aqueous phase was extracted with ethyl acetate (4×). The organic layers were dried over anhydrous magnesium sulfate, filtered and concentrated to give the crude title material (0.815 g, 100%) as an oil which solidified on standing. The compound was used as such in the next reaction. $^1$H NMR (400 MHz, CDCl$_3$) δ: 1.41 (9H, s), 3.96 (2H, d, J=6.32 Hz), 7.25-7.30 (2H, m), 7.32-7.38 (4H, m), 7.42-7.47 (4H, m).

2. Preparation of 2-methoxy-2,2-diphenylethanamine

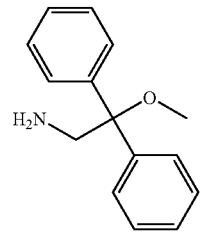

A solution of tent-butyl 2-hydroxy-2,2-diphenylethylcarbamate (0.42 g, 1.39 mmol) in methanol (10 mL) was treated with concentrated sulfuric acid (2 mL). The reaction was stirred at 23° C. for a week and then at 40° C. for 2 hours. Solid sodium bicarbonate was added to the reaction until the pH reached ~6-7 and the methanol was evaporated. The residue was then taken into ethyl acetate/water and the aqueous phase was extracted with ethyl acetate (3×). The combined organic layers were dried over anhydrous magnesium sulfate, filtered and concentrated. The residue was purified on preparative HPLC (ammonium acetate/acetonitrile/water) to give the title material (0.140 g, 46%). $^1$H NMR (400 MHz, CDCl$_3$) δ: 3.11 (3H, s), 3.54 (2H, br s), 3.98 (2H, br s), 7.24-7.30 (2H, m), 7.31-7.36 (8H, m).

BB) Synthesis of N$^1$-neopentyl-2,2-diphenylpropane-1,3-diamine

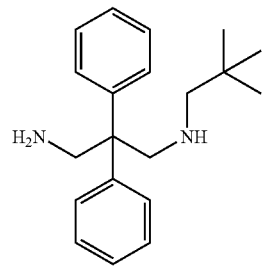

1. Preparation of tert-butyl 3-hydroxy-2,2-diphenylpropylcarbamate

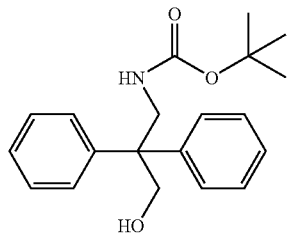

A solution of 3-amino-2,2-diphenylpropan-1-ol (5.13 g, 22.569 mmol, described in Example M) in dichloromethane (40 mL) was treated with Boc$_2$O (5.91 g, 27.083 mmol) at 23° C. The reaction was stirred for 45 minutes, then washed with water, dried over anhydrous magnesium sulfate, filtered and concentrated to give the crude title material (7.9 g, >100%) as a solid which was used as such in the next reaction. $^1$H NMR (400 MHz, CDCl$_3$) δ: 1.45 (9H, s), 3.46 (1H, t, J=7.33 Hz), 4.01 (2H, d, J=6.82 Hz), 4.20 (2H, d, J=7.33 Hz), 4.55 (1H, br s), 7.18-7.22 (4H, m), 7.25 (2H, t, J=7.33 Hz), 7.33 (4H, t, J=7.33 Hz). HPLC ret. time (Condition A): 1.990 min.

2. Preparation of tert-butyl 3-oxo-2,2-diphenylpropylcarbamate

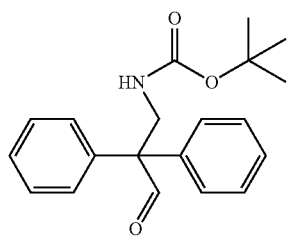

To a stirred solution of oxalyl chloride (0.441 mL, 5.039 mmol) in dichloromethane (15 mL) was added dropwise DMSO (0.716 mL) at −78° C. After 5 minutes, a solution of tent-butyl 3-hydroxy-2,2-diphenylpropylcarbamate (1.5 g, 4.58 mmol) in dichloromethane (7 mL) was slowly added at −78° C. and the reaction was stirred at −78° C. for 30 minutes. Triethylamine (3.193 mL, 22.906 mmol) was then added, the reaction was stirred at −78° C. for 10 minutes and then warmed up to 23° C. The reaction was then diluted with water, the phases were separated and the organic phase was dried over anhydrous magnesium sulfate, filtered and concentrated to give an oil. This was purified on Biotage chromatography (10% to 20% ethyl acetate/hexane) to give the title material (1.15 g, 77%) as an oil. $^1$H NMR (400 MHz, CDCl$_3$) δ: 1.31 (9H, s), 4.09 (2H, d, J=6.32 Hz), 4.79 (1H, br s), 7.22 (4H, d, J=7.33 Hz), 7.32-7.43 (6H, m), 9.90 (1H, s).

3. Preparation of N$^1$-neopentyl-2,2-diphenylpropane-1,3-diamine

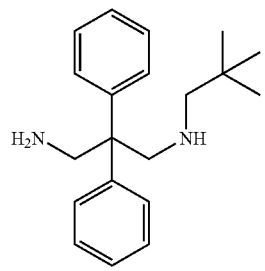

A mixture of tert-butyl 3-oxo-2,2-diphenylpropylcarbamate (0.10 g, 0.307 mmol) in DMF (4 mL) and trimethylorthoformate (4 mL) was treated with neopentylamine (0.054 g, 0.615 mmol), sodium triacetoxyborohydride (0.098 g, 0.461 mmol) and acetic acid (2 drops) and the reaction was stirred at 23° C. overnight. LC/MS shows only formation of the imine. The reaction was then treated with sodium borohydride (0.050 g, 1.32 mmol) and methanol (~2 mL) and stirred at 23° C. for 30 minutes. The reaction was acidified with 1N HCl and washed with diethyl ether. The aqueous phase was basified with sat. aq. sodium bicarbonate, extracted with diethyl ether (3×) and the combined organic layers were dried over anhydrous magnesium sulfate, filtered and concentrated to give the crude tert-butyl 3-(neopentylamino)-2,2-diphenylpropylcarbamate (0.055 g, 45%) as an oil. $^1$H NMR (400 MHz, CDCl$_3$) δ: 0.82 (9H, s), 0.92-0.96 (2H, m), 1.42 (9H, s), 2.35 (2H, s), 3.47 (2H, s), 3.86 (2H, d, J=4.80 Hz), 7.15 (1H, br s), 7.17-7.26 (6H, m), 7.28-7.34 (4H, m). HPLC ret. time (Condition A): 2.68 min. LC/MS (M+H)$^+$: 397.

The title material was prepared by treating a solution of the crude tert-butyl 3-(neopentylamino)-2,2-diphenylpropylcarbamate (0.055 g) in dichloromethane (5 mL) with trifluoroacetic acid (1 mL) at 23° C. for 30 minutes. The reaction was concentrated to dryness and the residue was used as such in the next reaction.

CC) Synthesis of 2,2-diphenyl-3-(piperidin-1-yl)propan-1-amine

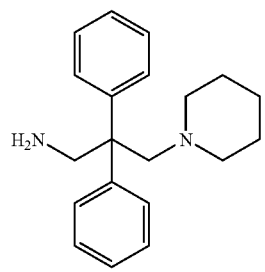

A mixture of tert-butyl 3-oxo-2,2-diphenylpropylcarbamate (0.60 g, 1.844 mmol) and piperidine (0.314 g, 3.688 mmol) in ethanol (10 mL) was treated with titanium isopropoxide (1.62 mL, 5.53 mmol) and this was stirred at 65° C. overnight. The reaction was then cooled down to 23° C. and sodium borohydride (0.279 g, 7.38 mmol) was added. The reaction was stirred for 2 more hours, then quenched with 10% ammonium hydroxide (10 mL), diluted with ethyl acetate and stirred for 30 minutes. The solid was removed by filtration and the filtrate was acidified with 1N HCl and washed with ethyl acetate. The filtrate was then basified with sat. aq. sodium bicarbonate and extracted with ethyl acetate (3×). The combined organic extracts were dried over anhydrous magnesium sulfate, filtered and concentrated to give the crude title material (0.28 g) as a colorless film. This was purified by silica gel chromatography (Biotage, ethyl acetate/hexane 20% to 50%) to give tert-butyl 2,2-diphenyl-3-(piperidin-1-yl)propylcarbamate (0.13 g, 18%) as an oil. $^1$H NMR (400 MHz, CDCl$_3$) δ ppm: 1.28-1.46 (6H, m), 1.41 (9H, s), 2.04-2.11 (4H, m), 3.06 (2H, br s), 3.98 (2H, d, J=5.56 Hz), 7.19-7.30 (10H, m). HPLC ret. time (Condition B): 2.633 min. LC/MS (M+H)$^+$: 395.

The title material was obtained by treating a solution of tert-butyl 2,2-diphenyl-3-(piperidin-1-yl)propylcarbamate (0.109 g) in dichloromethane (5 mL) with trifluoroacetic acid (1 mL) at 23° C. for 45 minutes. The reaction was then concentrated to dryness and the residue was used as such in the next reaction.

DD) Synthesis of
2-(4-methoxyphenyl)-2-phenylethanamine

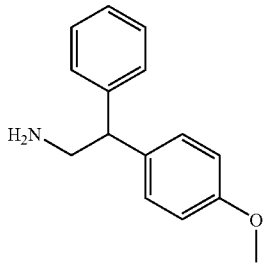

1. Preparation of
(E)-1-methoxy-4-(2-nitrovinyl)benzene

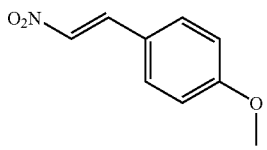

To a cool (0° C.), stirred solution of 4-anisaldehyde (1.75 mL, 14.3 mmol), nitromethane (2.0 mL, 36.9 mmol) in MeOH (6.0 mL) was added NaOH (1M, 40 mL), and allowed to warm to room temperature. After 2.5 hours, ice water was added with stirring, extracted with DCM (3×), the combined extracts were dried (MgSO$_4$), filtered, concentrated and purified on Biotage Horizon to provide the product as a solid: $^1$H NMR (400 MHz, CDCl$_3$) δ ppm: 7.97 (1H, d, J=13.64 Hz), 7.51 (1H, d, J=13.64 Hz), 7.50 (1H, d, J=8.84 Hz), 6.95 (2H, d, J=8.84 Hz), 3.86 (3H, s).

2. Preparation of
1-methoxy-4-(2-nitro-1-phenylethyl)benzene

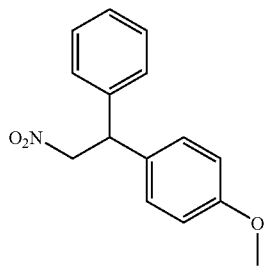

To a cold (−78° C.), stirred solution of (E)-1-methoxy-4-(2-nitrovinyl)benzene (153 mg, 0.86 mmol) in THF (20 mL) was added PhLi (0.64 mL, 1.6M) under Ar. After 1.5 h, the reaction was treated with MeOH, sat. NH4Cl and brine, and allowed to warm to room temperature. The reaction was extracted with EtOAc (3×), dried (MgSO4), filtered, concentrated then purified on Biotage Horizon to provide the product (150 mg, 68%) as an oil: $^1$H NMR (400 MHz, CDCl$_3$) δ ppm: 7.32 (2H, t, J=7.20 Hz), 7.19-7.25 (3H, m), 7.14 (2H, d, J=8.84 Hz), 6.84 (2H, d, J=8.84 Hz), 4.90-4.96 (2H, m), 4.81-4.87 (1H, m), 3.77 (3H, s).

3. Preparation of
2-(4-methoxyphenyl)-2-phenylethanamine

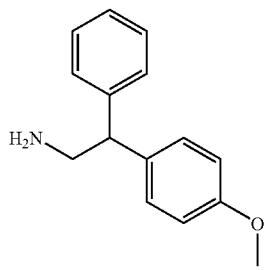

To prewashed (3× water, 3×MeOH) RaNi (0.40 g) in MeOH (10 mL) was added 1-methoxy-4-(2-nitro-1-phenylethyl)benzene (0.188 g, 0.73 mmol), then shaken under H$_2$ atmosphere (35 psi) in Parr shaker overnight. The reaction was filtered through Celite, washed with MeOH. The filtrate was concentrated to afford the product (155 mg, 94%) as a solid: $^1$H NMR (400 MHz, CDCl$_3$) δ ppm 7.11-7.36 (7H, m), 6.79-6.89 (2H, m), 4.21 1H, (t, J=7.45 Hz), 3.76 (3H, s), 3.24 (2H, d, J=8.84 Hz).

EE) Synthesis of 2-(1,3-dioxolan-2-yl)-2,2-diphenylethanamine

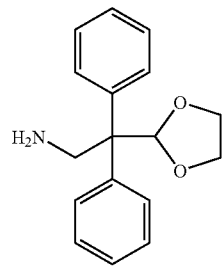

1. Preparation of benzyl 3-hydroxy-2,2-diphenylpropylcarbamate

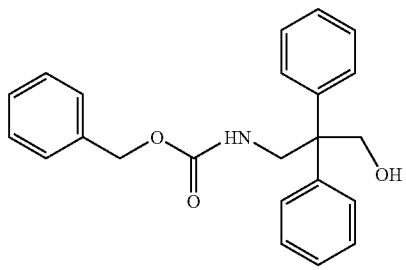

A solution of 3-amino-2,2-diphenylpropan-1-ol (18.4 g, 80.95 mmol) in dichloromethane (250 mL) was treated with triethylamine (16.9 mL, 121.4 mmol) and benzyl chloroformate (12.7 mL, 89.0 mmol) was then added dropwise over a period of 15 minutes. The reaction was stirred at 23° C., then diluted with water and stirred for 15 more minutes. The phases were separated and the organic phase was washed with 1N HCl, dried over anhydrous magnesium sulfate, filtered and concentrated to give the crude title material as an oil. This was purified on silica gel column (20% ethyl acetate/hexane) to give the title material (13.9 g, 47%) as an oil. $^1$H NMR (400 MHz, CDCl$_3$) δ ppm: 2.29 (1H, br s), 4.08 (2H, d, J=6.57 Hz), 4.20 (2H, s), 4.82 (1H, t, J=6.06 Hz), 5.12 (2H, s), 7.14-7.21 (4H, m), 7.23-7.29 (2H, m), 7.31-7.41 (9H, M). HPLC ret. time (Condition C): 6.098 min. LC/MS (M+H)$^+$: 362.

2. Preparation of benzyl 3-oxo-2,2-diphenylpropylcarbamate

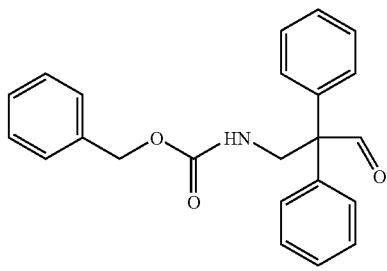

To a solution of oxalyl chloride (5.39 mL, 61.53 mmol) in dichloromethane (100 mL) was added dropwise dry DMSO (6.83 mL, 96.15 mmol) at −78° C. After 10 minutes at this temperature, a solution of benzyl 3-hydroxy-2,2-diphenylpropylcarbamate (13.9 g, 38.46 mmol) in dichloromethane (100 mL) was slowly added and stirred at −78° C. The reaction was stirred for 1 hour and triethylamine (26.8 mL, 192.3 mmol) was added and the reaction stirred at −78° C. for 10 more minutes then warmed to room 23° C. The reaction was diluted with 1N HCl and the phases were separated. The organic phase was dried over anhydrous magnesium sulfate, filtered and concentrated to give the crude title material (12.09 g, 87%) as an oil which was used as such in the next reaction. HPLC ret. time (Condition A): 2.093 min. LC/MS (M+H)$^+$: 360. $^1$H NMR (400 MHz, CDCl$_3$) δ ppm: 4.18 (2H, d, J=6.57 Hz), 4.98 (2H, s), 5.00 (1H, t, J=5.81 Hz), 7.17-7.42 (15H, 2 m), 9.90 (1H, s).

3. Preparation of 2-(1,3-dioxolan-2-yl)-2,2-diphenylethanamine

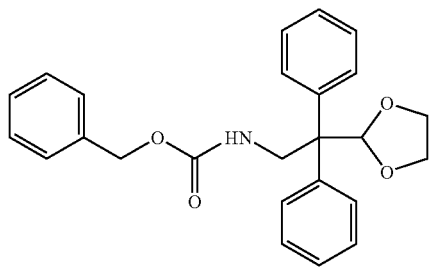

A mixture of benzyl 3-oxo-2,2-diphenylpropylcarbamate (12.0 g, 33.39 mmol), p-toluenesulfonic acid (0.635 g, 3.34 mmol), glycol (9.31 mL, 166.94 mmol) in toluene (300 mL) was heated overnight to reflux in a flask mounted with a Dean-Stark apparatus. The reaction was then concentrated to dryness and the residue was diluted with ethyl acetate, washed with aq. sat. sodium bicarbonate, dried over anhydrous magnesium sulfate, filtered and concentrated. The residue was triturated with hot ethyl acetate to give the title material (9.2 g, 68%) as a solid. HPLC ret. time (Condition A): 2.153 min. LC/MS (M+H)$^+$: 404. $^1$H NMR (400 MHz, CDCl$_3$) δ ppm: 3.72-3.80 (2H, m), 3.83-3.90 (2H, m), 4.20 (2H, d, J=5.56 Hz), 5.00 (2H, s), 5.07 (1H, s), 5.64 (1H, s), 7.22-7.34 (15H, m).

4. Preparation of 2-(1,3-dioxolan-2-yl)-2,2-diphenylethanamine

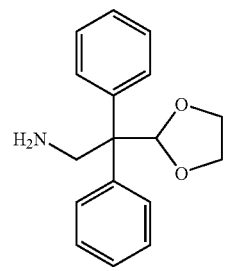

To a solution of 2-(1,3-dioxolan-2-yl)-2,2-diphenylethanamine (1.0 g, 2.48 mmol) in ethanol/THF (60 mL, 1:1), was added 10% Pd/C (~0.10 g) and the reaction was vigorously stirred under H$_2$ atmosphere (balloon). After 3 hours, the catalyst was removed by filtration on a Whatman Autovial PTFE filter and the filtrate was concentrated to dryness to give the title material (0.653 g, 98%) as an oil. $^1$H NMR (400 MHz, CDCl$_3$) δ ppm: 1.38 (2H, br s), 3.58-3.64 (4H, m), 3.79-3.88 (2H, m), 5.77 (1H, s), 7.22-7.34 (10H, m).

FF) Synthesis of 2-phenyl-2-o-tolylethanamine

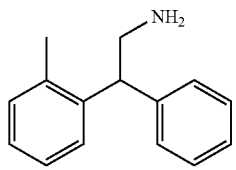

Potassium tert-butoxyde (8.64 g, 77 mmol) was added, in one portion, to a cold (0° C.) solution of Tosmic (6.04 g, 27.8 mmol) in DMSO (15 mL) and stirred for 5 min. MeOH (0.2 mL) was then added followed by phenyl(o-tolyl)methanone (1.82 g, 9.2 mmol) in one portion. The reaction was warmed up slowly over 12 hours to room temperature. The reaction mixture was partitioned between saturated aqueous sodium carbonate and ethyl acetate. The organic phase was dried over sodium sulfate and evaporated under reduced pressure to give a residue. TFA (3.85 mL, 50 mmol) in THF (5 mL) was slowly added to a cool (0° C.) suspension of sodium borohydride (2.1 g, 50 mmol) in THF (5 mL) over 10 minutes. To this solution was added the residue dissolved in THF (5 mL) over 5 minutes. The resulting mixture was warmed to room temperature and stirred 16 hrs. The reaction mixture was partitioned between saturated aqueous sodium carbonate and ethyl acetate. The organic phase was dried over sodium sulfate and evaporated under reduced pressure and dissolved in methanol. This solution was then passed through SCX resin (12 g, 0.78 mmol/g) and washed with methanol. These washes were discarded and the cartridge treated with 2M ammonia in methanol. The ammonia solution was then evaporated to generate the desired compound (1.322 g, 63%). $^1$H NMR (400 MHz, DMSO-d$_6$) δ ppm: 2.22 (3H, s) 3.04-3.16 (2H, m) 4.13 (1H, t, J=7.45 Hz) 7.08-7.31 (11H, m).

GG) Synthesis of 2-(2-bromophenyl)-2-phenylethanamine

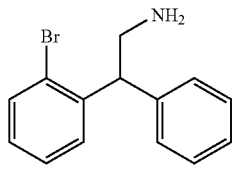

The title material was prepared as described for the synthesis of 2-phenyl-2-o-tolylethanamine (Example FF) in using (2-bromophenyl)(phenyl)methanone. $^1$H NMR (400 MHz, DMSO-d6) δ ppm: 3.15 (2H, dd, J=7.45, 2.65 Hz) 4.36 1H, (t, J=7.45 Hz) 7.12-7.20 (2H, m) 7.22-7.29 (5H, m) 7.38 (1H, td, J=7.52, 1.14 Hz) 7.48 (1H, dd, J=7.71, 1.64 Hz) 7.58 (1H, dd, J=7.83, 1.26 Hz).

HH) Synthesis of 2-phenyl-2-(pyridin-2-yl)ethanamine

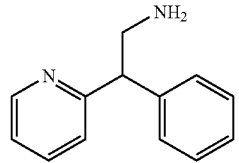

The title material was prepared as described for the synthesis of 2-phenyl-2-o-tolylethanamine (Example FF) in using phenyl(pyridin-2-yl)methanone. $^1$H NMR (400 MHz, DMSO-d$_6$) δ ppm 3.09 (1H, dd, J=12.51, 6.69 Hz) 3.36 (1H, dd, J=12.51, 8.21 Hz) 4.10 (1H, dd, J=8.20, 6.70 Hz) 7.16-7.21 (3H, m) 7.23-7.31 (7H, m) 7.64-7.70 (1H, m) 8.51-8.54 (1H, m). HPLC ret. time (Condition L): 1.098 min. LC/MS (M+H)$^+$: 199.

II) Synthesis of 2-(2-(methoxymethoxy)phenyl)-2-phenylethanamine

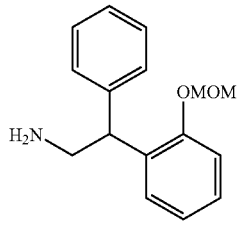

1. Preparation of (2-(methoxymethoxy)phenyl)(phenyl)methanone

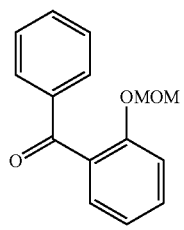

To a stirring solution of 2-hydroxybenzophenone (3.0 g, 15.1 mmol) and K$_2$CO$_3$ (9.94 g, 71.9 mmol) in acetone (80 mL) under reflux was added MOMCl (2.9 mL, 37.8 mmol) and allowed to stir overnight. The reaction was then cooled to 23° C., diluted with EtOAc, washed with 2N NaOH (3×), the organic phase dried (Na$_2$SO$_4$), filtered and concentrated to provide the product (605 mg) as an oil: $^1$H NMR (400 MHz, DMSO-d$_6$) δ ppm 7.67-7.72 (2H, m), 7.63 (1H, d, J=7.07 Hz), 7.48-7.54 (3H, m), 7.34 (1H, dd, J=7.33, 1.52 Hz), 7.24 (1H, d, J=8.34 Hz), 7.13 (1H, t, J=7.45 Hz), 5.08 (2H, s), 3.13 (3H, s).

2. Preparation of 2-(2-(methoxymethoxy)phenyl)-2-phenylethanamine

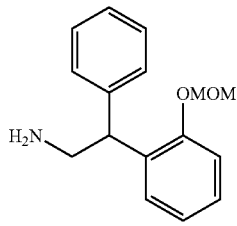

The title material was prepared as described for the synthesis of 2-phenyl-2-o-tolylethanamine (Example FF) in using (2-(methoxymethoxy)phenyl)(phenyl)methanone. $^1$H NMR (400 MHz, DMSO-d$_6$) δ ppm: 6.88-7.44 (9H, m), 5.16-5.18 (1H, m), 5.09-5.15 (2H, m), 3.41-3.46 (2H, m), 3.21-3.23 (3H, m).

Example 1

N-(2-hydroxy-2,2-diphenylethyl)-4-(2-(pyridin-2-ylamino)thiazol-5-ylthio)picolinamide

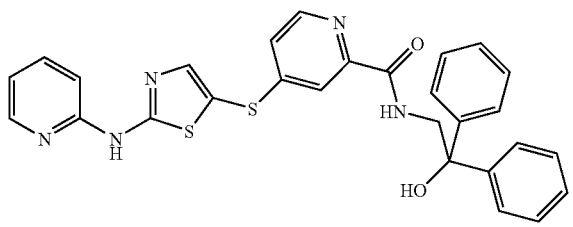

A) Synthesis of 4-(2-(pyridin-2-ylamino)thiazol-5-ylthio)picolinic acid

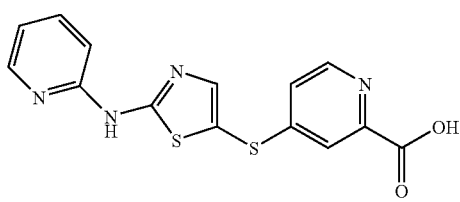

A DMF (3 mL) suspension of 4-chloropicolinic acid (0.160 g, 1.01 mmol) and sodium hydrogensulfide hydrate (0.225 g, 3.03 mmol, 3 eq) was heated to 100° C. After 3 h, the suspension was diluted with methanol (10 mL), 5-bromo-N-(pyridine-2-yl)thiazol-2-amine (0.256 g, 1.0 mmol, 1 eq, described in the synthesis of thiazoles Example A) was added followed by a solution of sodium methoxide 25% (2 mL). The resulting mixture was heated at 80° C. for 15 min., concentrated to remove most of the methanol, diluted with DMF and acidified with acetic acid. The resulting solution was purified on preparative HPLC (ammonium acetate/water/acetonitrile) and freeze dried to give the title compound as a solid (0.094 mg, 28%). $^1$H NMR (400 MHz, DMSO-d$_6$) δ ppm 7.00 (1H, dd, J=6.69, 5.68 Hz), 7.12 (1H, d, J=8.34 Hz), 7.34 (1H, dd, J=5.31, 1.77 Hz), 7.68 (1H, d, J=1.52 Hz), 7.73-7.83 (2H, m), 8.31 (1H, d, J=4.04 Hz), 8.48 (1H, d, J=5.31 Hz), 11.80 (1H, s). LC/MS (M+H)$^+$: 331, (M−H)$^−$: 329.

Synthesis of N-(2-hydroxy-2,2-diphenylethyl)-4-(2-(pyridine-2-ylamino)thiazol-5-ylthio)picolinamide

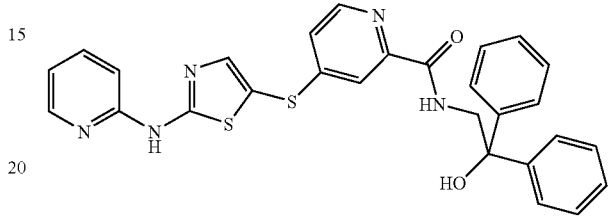

To a solution of 4-(2-(pyridine-2-ylamino)thiazol-5-ylthio)picolinic acid (0.063 g, 0.19 mmol) and 2-amino-1,1-diphenylethanol (0.060 g, 0.28 mmol, 1.5 eq, described in Example D) in NMP (3 mL), was added EDAC (0.055 g, 0.28 mmol, 1.5 eq), HOBt (0.026 g, 0.19 mmol, 1 eq) and diisopropylethylamine (0.100 mL, 0.57 mmol, 3 eq). The resulting mixture was stirred at 23° C. for 3.5 h. The mixture was purified on preparative HPLC (ammonium acetate/water/acetonitrile) and freeze dried to give the title compound as a solid (0.024 mg, 24%). The product was converted to the HCl salt by dissolving it in ethyl acetate (2 mL) and tetrahydrofuran (2 mL) and treating the mixture with a solution of HCl (4.0 M in dioxane, 0.011 mL, 0.045 mmol, 1 eq). The mixture was concentrated, then diluted with water and lyophilized to give the HCl salt of the title material (0.029 g) as a solid. $^1$H NMR (400 MHz, DMSO-d$_6$) δ ppm 4.10 (2H, d, J=5.56 Hz), 6.30 (1H, s), 7.01 (1H, dd, J=6.69 and 5.43 Hz), 7.11-7.20 (3H, m), 7.28 (4H, t, J=7.71 Hz), 7.37 (1H, dd, J=5.31, 2.02 Hz), 7.42-7.48 (4H, m), 7.66 (1H, d, J=1.52 Hz), 7.79 (1H, ddd, J=9.22, 6.32 and 1.89 Hz), 8.31 (1H, dd, J=5.43 and 1.39 Hz), 8.40 (1H, t, J=4.80 Hz), 8.41 (1H, d, J=4.8 Hz), 11.86 (1H, s). LC/MS (M+H)$^+$: 526. Ret. time: 2.00 (Condition D). HRMS: calcd: 526.1371; found: 526.1387.

The following examples were prepared according to the procedure described in Example 1.

Example 2

N-(2-phenylpropyl)-4-(2-(pyridin-2-ylamino)thiazol-5-ylthio)picolinamide

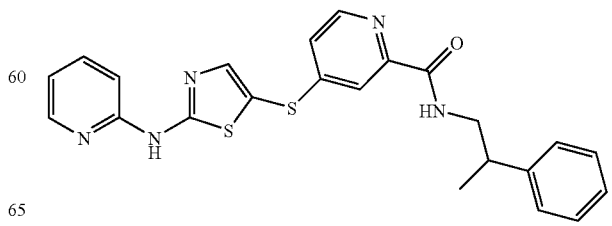

The title material was prepared using 2-phenylpropan-1-amine (commercially available). LC/MS (M+H)+: 448. Ret. time: 2.04 min. (Condition D). HRMS calcd: 448.1266; found: 448.1283.

Example 3

N-((2-phenyl-1,3-dioxolan-2-yl)methyl)-4-(2-(pyridin-2-ylamino)thiazol-5-ylthio)picolinamide

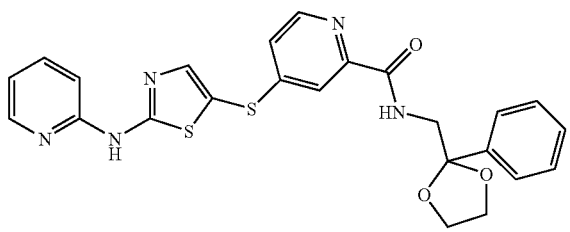

The title material was prepared using (2-phenyl-1,3-dioxolan-2-yl)methanamine (Adachi, J.; Sato, N. *J. Org. Chem.* 1972, 37, 221). LC/MS (M+H)+: 492. Ret. time: 1.95 min. (Condition D). HRMS calcd: 492.1164; found: 492.1162.

Example 4

N-(2,2-diphenylethyl)-4-(2-(pyridin-2-ylamino)thiazol-5-ylthio)picolinamide

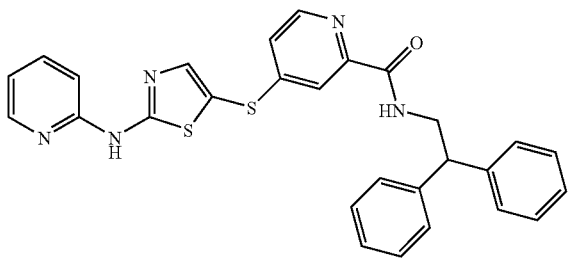

The title material was prepared using 2,2-diphenylethanamine (commercially available). LC/MS (M+H)+: 510. Ret. time: 2.16 min. (Condition D). HRMS calcd: 510.1422; found: 510.1422.

Example 5

N-((1S,2R)-2-phenylcyclopropyl)-4-(2-(pyridin-2-ylamino)thiazol-5-ylthio)picolinamide

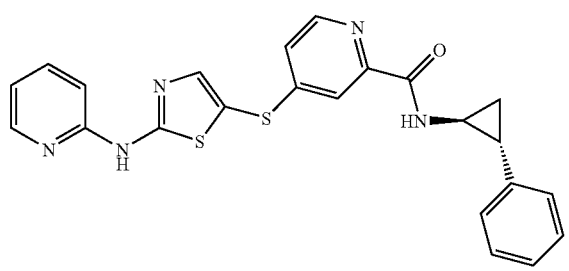

The title material was prepared using (1S,2R)-2-phenylcyclopropanamine (commercially available). LC/MS (M+H)+: 446. Ret. time: 2.00 min. (Condition D). HRMS calcd: 446.1109; found: 446.1110.

Example 6

N-(2-hydroxy-2-phenylbutyl)-4-(2-(pyridin-2-ylamino)thiazol-5-ylthio)picolinamide

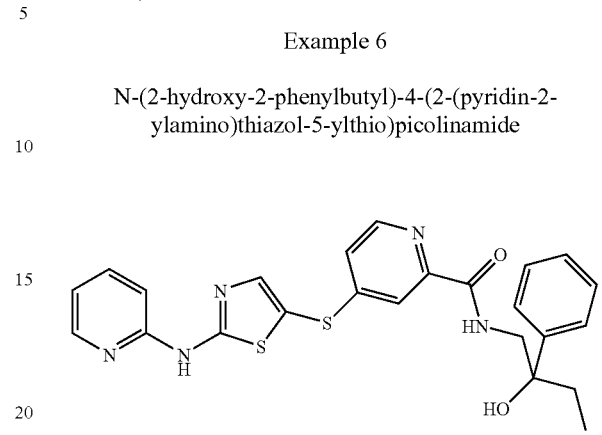

The title material was prepared using 1-amino-2-phenylbutan-2-ol (described in the synthesis of amines, Example F). LC/MS (M+H)+: 478. Ret. time: 1.87 min. (Condition D). HRMS calcd: 478.1371; found: 478.1388.

Example 7

(S)—N-(2-(3-chloro-4-methoxyphenyl)-2-hydroxyethyl)-4-(2-(pyridin-2-ylamino)thiazol-5-ylthio)picolinamide

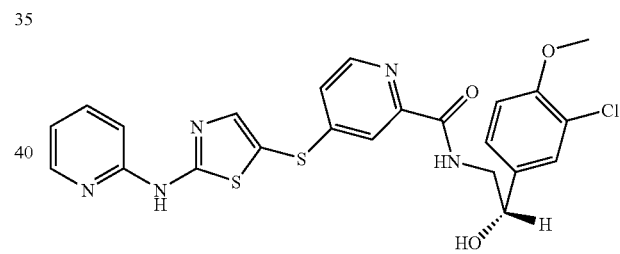

The title material was prepared using (S)-2-amino-1-(3-chloro-4-methoxyphenyl)ethanol (described in the synthesis of amines, Example C). LC/MS (M+H)+: 514, 516. Ret. time: 1.77 min. (Condition D). HRMS calcd: 514.0774; found: 514.0784.

Example 8

(S)—N-(2-(3-bromophenyl)-2-hydroxyethyl)-4-(2-(pyridin-2-ylamino)thiazol-5-ylthio)picolinamide

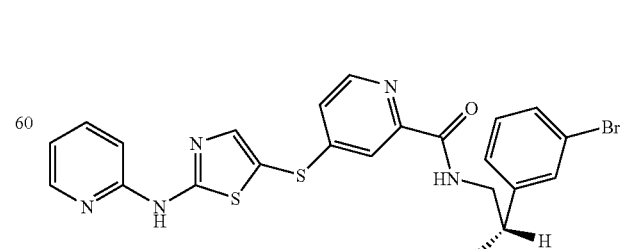

The title material was prepared using 1-amino-2-phenylpentan-2-ol (described in the synthesis of amines, Example E). LC/MS (M+H)$^+$: 528, 530. Ret. time: 1.83 min. (Condition D). HRMS: calcd: 528.0164; found: 528.0166.

Example 9

N-(2-hydroxy-2-phenylpentyl)-4-(2-(pyridin-2-ylamino)thiazol-5-ylthio)picolinamide

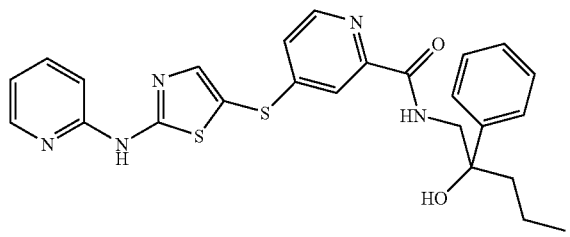

The title material was prepared using (S)-2-amino-1-[3-bromophenyl]ethanol hydrochloride (described in the synthesis of amines, Example B). LC/MS (M+H)$^+$: 492. Ret. time: 1.97 min. (Condition D). HRMS calcd: 492.1528; found: 492.1526.

Example 10

N-(2-hydroxy-4,4-dimethyl-2-phenylpentyl)-4-(2-(pyridin-2-ylamino)thiazol-5-ylthio)picolinamide

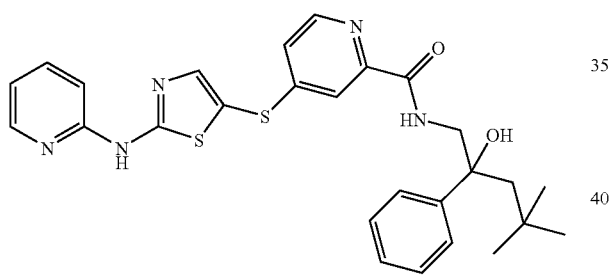

The title material was prepared using 1-amino-4,4-dimethyl-2-phenylpentan-2-ol (described in the synthesis of amines, Example G). LC/MS (M+H)$^+$: 520. Ret. time: 2.22 min. (Condition D). HRMS calcd: 520.1841; found: 520.1827.

Example 11

N-((1S)-1,3-dihydroxy-1-phenylpropan-2-yl)-4-(2-(pyridin-2-ylamino)thiazol-5-ylthio)picolinamide

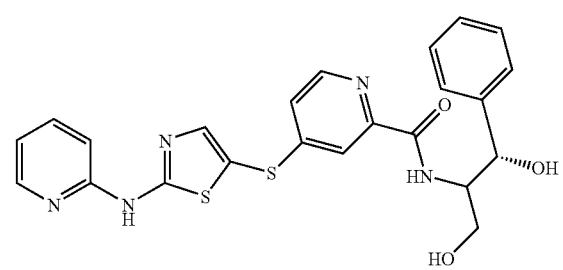

The title material was prepared using (1S)-2-amino-1-phenylpropane-1,3-diol (commercially available). LC/MS (M+H)$^+$: 480. Ret. time: 1.55 min. (Condition D). HRMS calcd: 480.1164; found: 480.1154.

Example 12

N-((1S,2S)-1-hydroxy-3-methoxy-1-phenylpropan-2-yl)-4-(2-(pyridin-2-ylamino)thiazol-5-ylthio)picolinamide

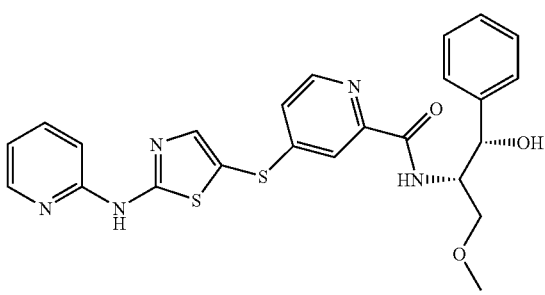

The title material was prepared using (1S,2S)-2-amino-3-methoxy-1-phenylpropan-1-ol (commercially available). LC/MS (M+H)$^+$: 494. Ret. time: 1.76 min. (Condition D). HRMS calcd: 494.1321; found: 494.1314.

Example 13

N-(2-hydroxy-2-(4-hydroxyphenyl)ethyl)-4-(2-(pyridin-2-ylamino)thiazol-5-ylthio)picolinamide

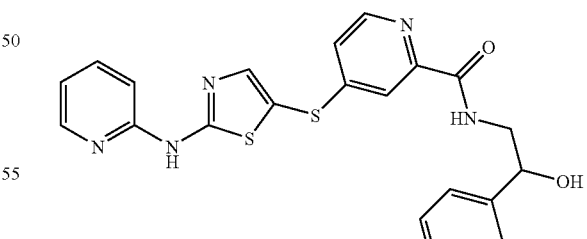

The title material was prepared using 4-(2-amino-1-hydroxyethyl)phenol (commercially available). LC/MS (M+H)$^+$: 466. Ret. time: 1.51 min. (Condition D). HRMS calcd: 466.1008; found: 466.0986.

Example 14

N-(2-oxo-2-phenylethyl)-4-(2-(pyridin-2-ylamino)thiazol-5-ylthio)picolinamide

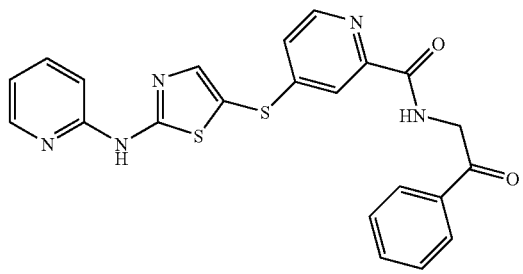

The title material was prepared using 2-amino-1-phenylethanone (commercially available). LC/MS (M+H)+: 448. Ret. time: 1.86 min. (Condition D). HRMS calcd: 448.0902; found: 448.0896.

Example 15

N-(2-hydroxy-2-phenyl-2-(pyridin-2-yl)ethyl)-4-(2-(pyridin-2-ylamino)thiazol-5-ylthio)picolinamide

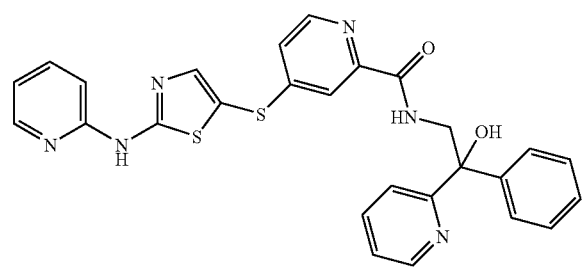

The title material was prepared using 2-amino-1-phenyl-1-(pyridin-2-yl)ethanol (described in synthesis of amines, Example H). LC/MS (M+H)+: 527. Ret. time: 2.04 min. (Condition D). HRMS calcd: 527.1324; found: 527.1323.

Example 16

N-(2-hydroxy-2-(3-methoxyphenyl)ethyl)-4-(2-(pyridin-2-ylamino)thiazol-5-ylthio)picolinamide

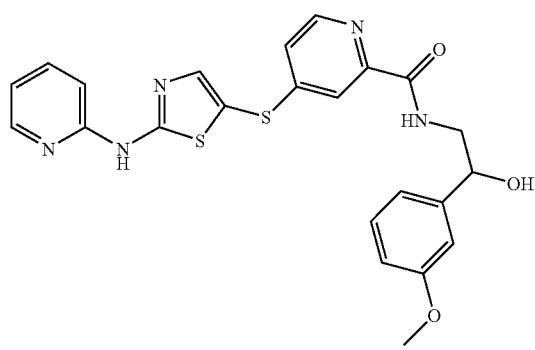

The title material was prepared using 2-amino-1-(3-methoxyphenyl)ethanol (described in synthesis of amines, Example K). LC/MS (M+H)+: 480. Ret. time: 1.68 min. (Condition D). HRMS calcd: 480.1164; found: 480.1147.

Example 17

N-(2-hydroxy-2-(pyridin-2-yl)pentyl)-4-(2-(pyridin-2-ylamino)thiazol-5-ylthio)picolinamide

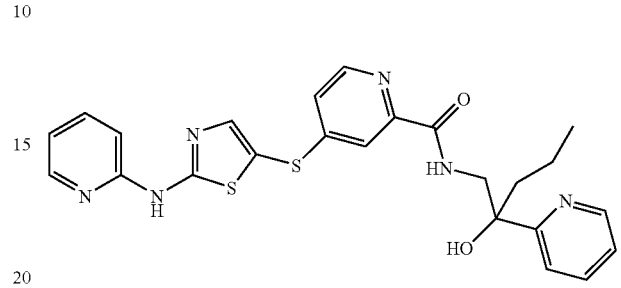

The title material was prepared using 1-amino-2-(pyridin-2-yl)pentan-2-ol (described in synthesis of amines, Example L). LC/MS (M+H)+: 493. Ret. time: 1.99 min. (Condition D). HRMS calcd: 493.1480; found: 493.1485.

Example 18

N-(2-hydroxy-2-(4-methylpyridin-2-yl)pentyl)-4-(2-(pyridin-2-ylamino)thiazol-5-ylthio)picolinamide

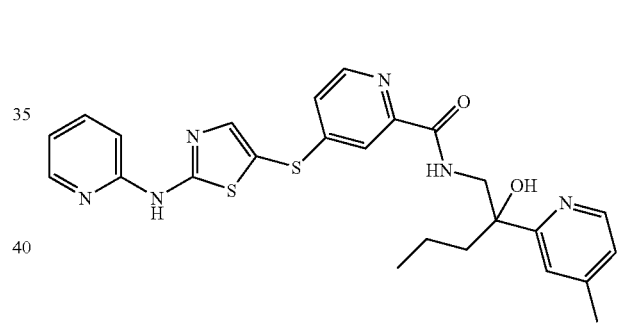

The title material was prepared using 1-amino-2-(4-methylpyridin-2-yl)pentan-2-ol (described in synthesis of amines, Example M). LC/MS (M+H)+: 507. Ret. time: 2.06 min. (Condition D). HRMS calcd: 507.1637; found: 507.1654.

Example 19

3-fluoro-N-(2-hydroxy-2-phenylpentyl)-4-(2-(pyridin-2-ylamino)thiazol-5-ylthio)picolinamide

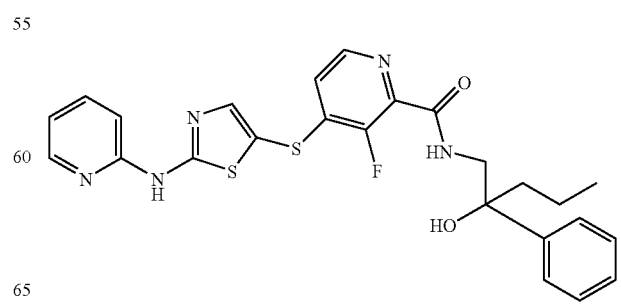

A. Synthesis of methyl 4-chloro-3-fluoropicolinate

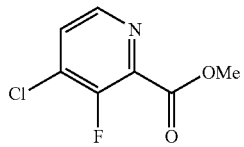

The title compound was prepared according to the procedure described in Org. Prep. and Proc. Int., 29 (1), 117-122 (1997). A suspension of lithium 4-chloro-3-fluoropicolinate (20.0 g, 136 mmol) and sodium bromide (28.0 g, 272 mmol, 2 eq) in thionyl chloride (99 mL, 1.36 mmol, 10 eq) was heated to reflux (95° C.) with an argon flush. The reaction was refluxed for 2 days then thionyl chloride (50 mL, 680 mmol, 5 eq) was added again and the reaction was refluxed for 3 more days. The mixture was then evaporated and the residue cooled down to 0° C. Methanol (300 mL) was cautiously added by portions and the mixture was stirred at 23° C. overnight. The reaction was then partitioned into ethyl acetate/sat. aq sodium carbonate and the aqueous phase was extracted with ethyl acetate. The combined organic layers were dried over magnesium sulfate, filtered and concentrated. The residue was dissolved in boiling hexanes and the residual tar was decanted. The filtrate was evaporated to give the title material (24.36 g, 94%) as a solid. $^1$H NMR (400 MHz, DMSO-$d_6$) δ ppm 3.92 (3H, s), 8.01 (1H, t, J=5.1 Hz), 8.50 (1H, d, J=5.1 Hz). LC/MS (M+H)$^+$: 190.

B. Synthesis of 3-fluoro-4-(2-(pyridin-2-ylamino)thiazol-5-ylthio)picolinic acid

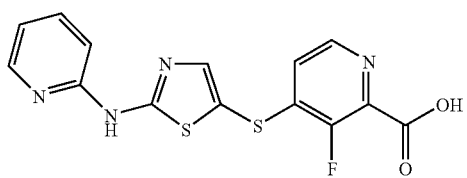

A DMF (3 mL) solution of methyl 4-chloro-3-fluoropicolinate (0.3 g, 1.58 mmol) was bubbled 10 min with argon, then sodium hydrogensulfide hydrate (0.146 g, 1.98 mmol, 1.25 eq) was added and the mixture was gently heated to 37° C. The mixture was diluted with methanol then 5-bromo-N-(pyridin-2-yl)thiazol-2-amine (0.404 g, 1.58 mmol, 1 eq, described in the synthesis of thiazoles Example A) was added, followed by a solution of sodium methoxide 25% (0.725 mL, 3.16 mmol, 2 eq). The mixture was heated at 65° C. for 1 h, cooled to 23° C., diluted with water (5 ml) and stirred 5 days. The mixture was neutralized with HCl 1N, concentrated to dryness, suspended in water, sonicated and the resulting solid was collected by filtration. The solid was purified on preparative HPLC (TFA/water/acetonitrile) and the fractions were concentrated on speedvac to give the title compound as a solid (0.023 g, 4%). The compound was used as such in the next step.

C. Synthesis of 3-fluoro-N-(2-hydroxy-2-phenylpentyl)-4-(2-(pyridin-2-ylamino)thiazol-5-ylthio)picolinamide

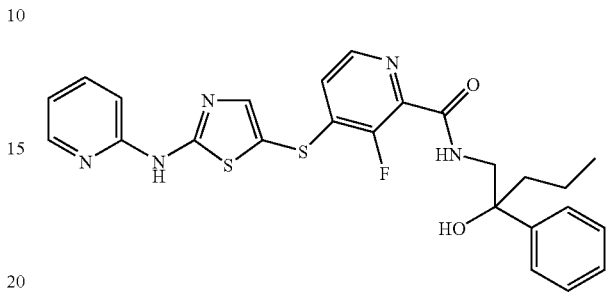

1-Amino-2-phenylpentan-2-ol (0.099 g, 0.45 mmol, 1.5 eq) was dissolved in NMP (3 mL) and to this solution was added 3-fluoro-4-(2-(pyridin-2-ylamino)thiazol-5-ylthio)picolinic acid (0.101 g, 0.30 mmol), EDAC (0.089 g, 0.45 mmol, 1.5 eq), HOBt (0.042 g, 0.30 mmol, 1 eq) and diisopropylethylamine (0.16 mL, 0903 mmol, 3 eq). The resulting mixture was stirred at 23° C. for 2 h. The mixture was then purified on preparative HPLC (ammonium acetate/water/acetonitrile) and freeze dried to give the title compound (0.0552 g, 36%). $^1$H NMR (400 MHz, DMSO-$d_6$) δ ppm: 0.76 (3H, t, J=7.33 Hz), 0.84-0.96 (1H, m), 1.19-1.30 (1H, m), 1.68-1.79 (2H, m), 3.63 (2H, d, J=5.81 Hz), 5.29 (1H, s), 7.01 (1H, dd, J=6.82 and 5.56 Hz), 7.05 (1H, t, J=5.18 Hz), 7.12 (1H, d, J=8.34 Hz), 7.20 (1H, t, J=7.33 Hz), 7.31 (2H, t, J=7.71 Hz), 7.42-7.46 (2H, m), 7.78 (1H, td, J=7.77 and 1.89 Hz), 7.82 (1H, s), 8.22-8.26 (2H, m), 8.31 (1H, dd, J=5.05 and 1.01 Hz), 11.88 (1H, s). LC/MS (M+H)$^+$: 510. HPLC ret. time (Condition J): 6.095 min. HRMS calcd: 510.1434; found: 510.1412.

The following examples were prepared according to the procedure described in Example 19.

Example 20

(S)-3-fluoro-N-(2-hydroxy-2-phenylpentyl)-4-(2-(pyridin-2-ylamino)thiazol-5-ylthio)picolinamide

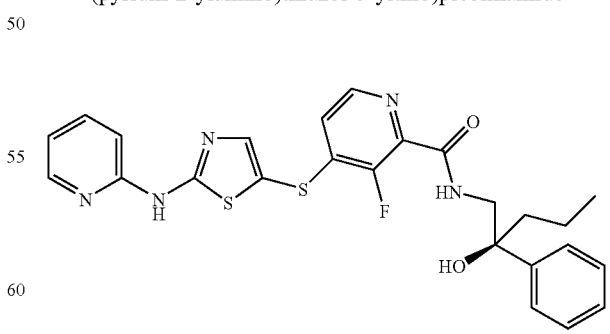

The title material was prepared using (S)-1-amino-2-phenylpentan-2-ol (described in the synthesis of amines, Example I). LC/MS (M+H)$^+$: 510. Ret. time: 2.02 min. (Condition E). Chiral HPLC (Chiralpack AD, 4.6×250 mm, 10 um, P/N 19025, 70:30 Heptane:Ethanol, 1.0 mL/min, 25° C., 315 nm): 99.4% ee; Retention time: 15.92 min.

Example 21

(R)-3-fluoro-N-(2-hydroxy-2-phenylpentyl)-4-(2-(pyridin-2-ylamino)thiazol-5-ylthio)picolinamide

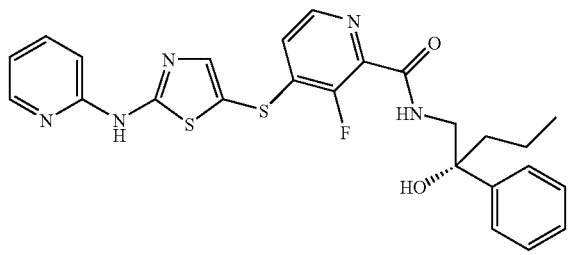

The title material was prepared using (R)-1-amino-2-phenylpentan-2-ol (described in the synthesis of amines, Example J). LC/MS (M+H)⁺: 510. Ret. time: 2.02 min. (Condition E). Chiral HPLC (Chiralpack AD, 4.6×250 mm, 10 um, P/N 19025, 70:30 Heptane:Ethanol, 1.0 mL/min, 25° C., 315 nm): 99.4% ee; Retention time: 11.88 min.

Example 22

N-(2,2-diphenylethyl)-3-fluoro-4-(2-(pyridin-2-ylamino)thiazol-5-ylthio)picolinamide

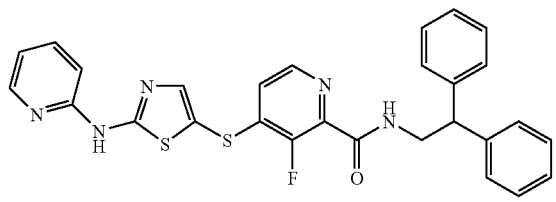

The title material was prepared using 2,2-diphenylethanamine (commercially available). LC/MS (M+H)⁺: 528. Ret. time: 6.996 min. (Condition C). HRMS: calc. 528.1328; found 528.1340.

Example 23

3-Fluoro-N-(3-fluorophenethyl)-4-(2-(pyridin-2-ylamino)thiazol-5-ylthio)picolinamide

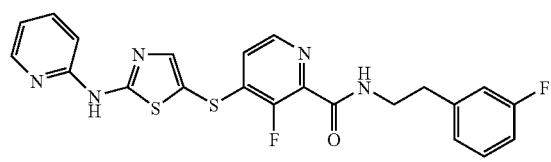

The title material was prepared using 2-(3-fluorophenyl)ethanamine (commercially available). LC/MS (M+H)⁺: 470. Ret. time: 6.130 min. (Condition C). HRMS: calc. 470.0921; found 470.0929.

Example 24

3-Fluoro-N-(2-hydroxy-2,2-diphenylethyl)-4-(2-(pyridin-2-ylamino)thiazol-5-ylthio)picolinamide

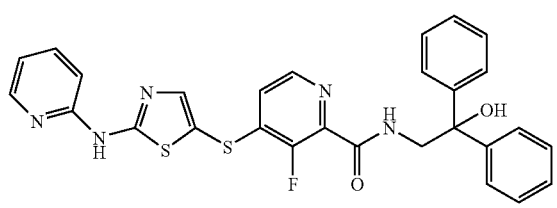

The title material was prepared using 2-amino-1,1-diphenylethanol (described in synthesis of amines, Example D). LC/MS (M+H)⁺: 544. Ret. time: 6.395 min. (Condition C). HRMS: calc. 544.1277; found 544.1281.

Example 25

3-Fluoro-N-((1-phenylcyclopropyl)methyl)-4-(2-(pyridin-2-ylamino)thiazol-5-ylthio)picolinamide

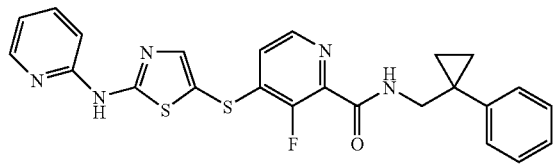

The title material was prepared using 2-amino-1,1-diphenylethanol (described in synthesis of amines, Example V). LC/MS (M+H)⁺: 478. Ret. time: 8.628 min. (Condition C). HRMS: calc. 478.1172; found 478.1185.

Example 26

N-(2,2-diphenylpropyl)-3-fluoro-4-(2-(pyridin-2-ylamino)thiazol-5-ylthio)picolinamide

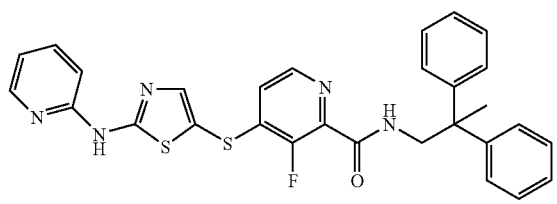

The title material was prepared using 2,2-diphenylpropan-1-amine (commercially available). LC/MS (M+H)⁺: 542. Ret. time: 7.513 min. (Condition C). HRMS: calc. 542.1485; found 542.1465.

Example 27

3-Fluoro-N-(2-hydroxy-2-phenylethyl)-4-(2-(pyridin-2-ylamino)thiazol-5-ylthio)picolinamide

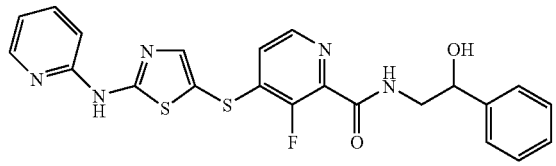

The title material was prepared using 2-amino-1-phenylethanol (commercially available). LC/MS (M+H)⁺: 468. Ret. time: 5.080 min. (Condition C). HRMS: calc. 468.0964; found 468.0984.

Example 28

3-Fluoro-N-phenethyl-4-(2-(pyridin-2-ylamino)thiazol-5-ylthio)picolinamide

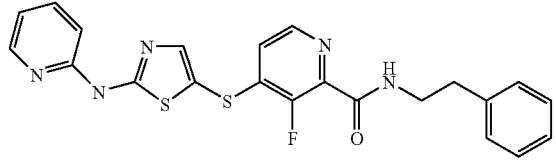

The title material was prepared using 2-phenylethanamine (commercially available). LC/MS (M+H)⁺: 452. Ret. time: 6.103 min. (Condition C). HRMS: calc. 452.1015; found 452.1035.

Example 29

3-Fluoro-N-(3-hydroxy-2,2-diphenylpropyl)-4-(2-(pyridin-2-ylamino)thiazol-5-ylthio)picolinamide

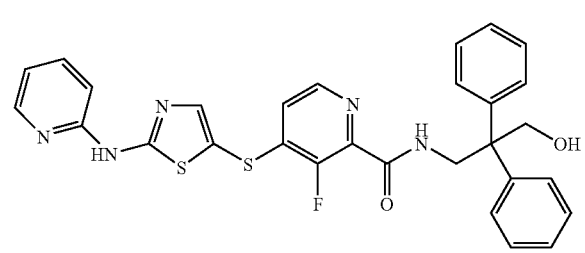

The title material was prepared using 3-amino-2,2-diphenylpropan-1-ol (described in synthesis of amines, Example P). LC/MS (M+H)⁺: 558. Ret. time: 6.450 min. (Condition C). HRMS: calc. 558.1434; found 558.1422.

Example 30

3-Fluoro-N-(2-hydroxy-2,2-dim-tolylethyl)-4-(2-(pyridin-2-ylamino)thiazol-5-ylthio)picolinamide

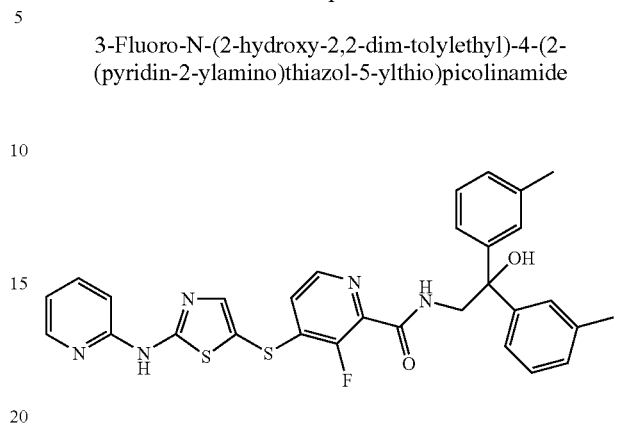

The title material was prepared using 2-amino-1,1-dim-tolylethanol (described in synthesis of amines, Example Z). LC/MS (M+H)⁺: 572. Ret. time: 6.936 min. (Condition C). HRMS: calc. 572.1590; found 572.1606.

Example 31

3-Fluoro-N-(2-methoxy-2,2-diphenylethyl)-4-(2-(pyridin-2-ylamino)thiazol-5-ylthio)picolinamide

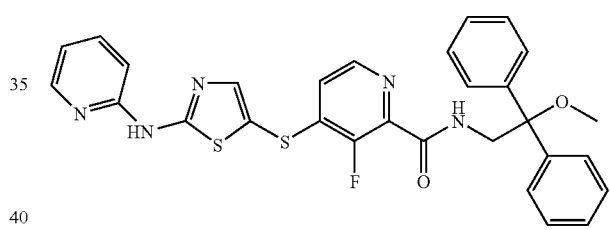

The title material was prepared using 2-methoxy-2,2-diphenylethanamine (described in synthesis of amines, Example AA). LC/MS (M+H)⁺: 558. Ret. time: 7.311 min. (Condition C). HRMS: calc. 558.1434; found 558.1442.

Example 32

3-Fluoro-4-(2-(pyridin-2-ylamino)thiazol-5-ylthio)-N-(2-(thiophen-2-yl)ethyl)picolinamide

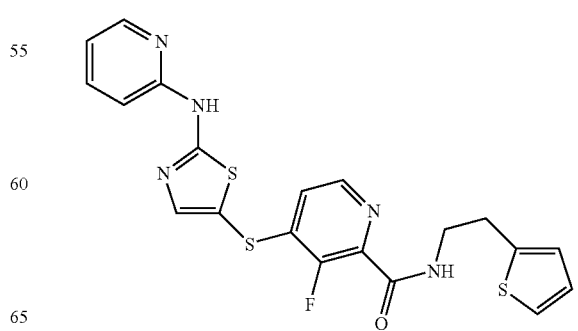

The title material was prepared using 2-(thiophen-2-yl)ethanamine (commercially available). LC/MS (M+H)+: 458. Ret. time: 1.83 min. (Condition A).

Example 33

3-Fluoro-N-(2-(5-hydroxy-1H-indol-3-yl)ethyl)-4-(2-(pyridin-2-ylamino)thiazol-5-ylthio)picolinamide

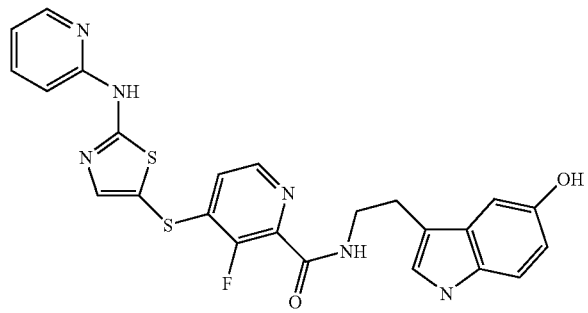

The title material was prepared using 2-(thiophen-2-yl)ethanamine (commercially available). LC/MS (M+H)+: 507. Ret. time: 1.57 min. (Condition A).

Example 34

3-Fluoro-N-(2-phenyl-2-(pyrrolidin-2-yl)ethyl)-4-(2-(pyridin-2-ylamino)thiazol-5-ylthio)picolinamide

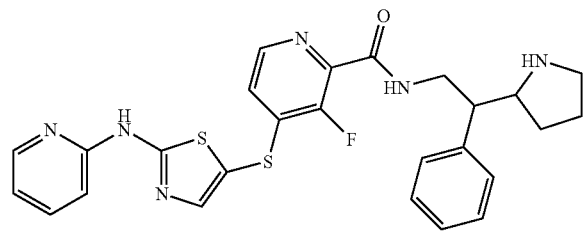

The title material was prepared using 2-phenyl-2-(pyrrolidin-2-yl)ethanamine (commercially available). LC/MS (M+H)+: 521. Ret. time: 1.44 min. (Condition A). HRMS calcd: 521.1594; found: 521.1615.

Example 35

N-(3-(dimethylamino)-2,2-diphenylpropyl)-3-fluoro-4-(2-(pyridin-2-ylamino)thiazol-5-ylthio)picolinamide

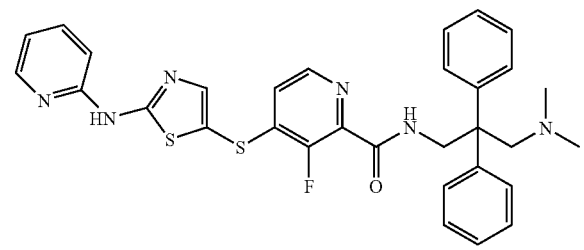

The title material was prepared using $N^1,N^1$-dimethyl-2,2-diphenylpropane-1,3-diamine (described in the synthesis of amines, Example R). LC/MS (M+H)+: 585. Ret. time: 5.211 min. (Condition C). HRMS: calc. 585.1907; found 585.1932.

Example 36

3-Fluoro-N-(3-(neopentylamino)-2,2-diphenylpropyl)-4-(2-(pyridin-2-ylamino)thiazol-5-ylthio)picolinamide

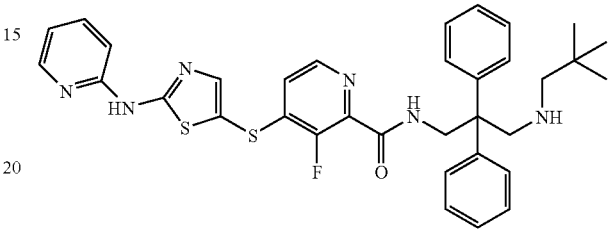

The title material was prepared using $N^1$-neopentyl-2,2-diphenylpropane-1,3-diamine (described in the synthesis of amines, Example BB). LC/MS (M+H)+: 627. Ret. time: 6.305 min. (Condition C). HRMS: calc. 627.2376; found 627.2372.

Example 37

3-Fluoro-N-(2-(2-((methoxymethoxy)methyl)phenyl)-2-phenylethyl)-4-(2-(pyridin-2-ylamino)thiazol-5-ylthio)picolinamide

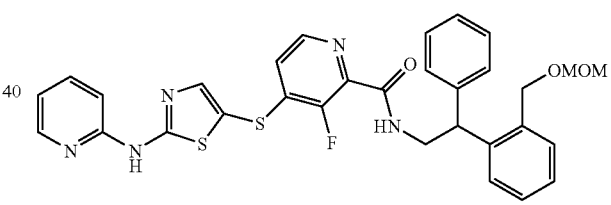

The title material was prepared using 2-(2-((methoxymethoxy)methyl)phenyl)-2-phenylethanamine (described in the synthesis of amines, Example V). LC/MS (M+H)+: 602. Ret. time: 2.07 min. (Condition E). HRMS: calc: 602.1696; found: 602.1699.

Example 38

3-Fluoro-N-(2-(pyridin-2-yl)ethyl)-4-(2-(pyridin-2-ylamino)thiazol-5-ylthio)picolinamide

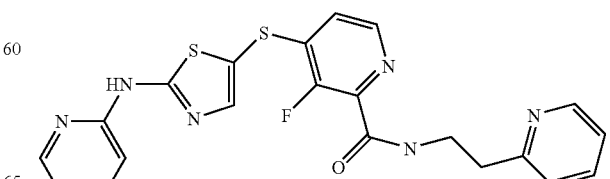

The title material was prepared using 2-(2-aminoethyl) pyridine (commercially available). LC/MS (M+H)+: 453. Ret. time: 3.503 min. (Condition H). HRMS: calc: 602.1696; found: 602.1699.

Example 39

3-Fluoro-N-(2-hydroxy-2-(pyridin-2-yl)propyl)-4-(2-(pyridin-2-ylamino)thiazol-5-ylthio)picolinamide

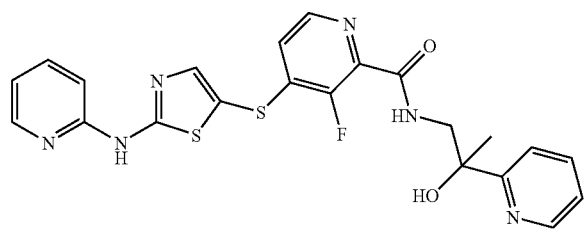

The title material was prepared using 1-amino-2-(pyridin-2-yl)propan-2-ol (described in synthesis of amines, Example M). LC/MS (M+H)+: 483, (M−H)−: 481. Ret. time: 6.078 min. (Condition J). HRMS: calc: 483.1073; found: 483.1091.

Example 40

3-fluoro-N-(2-hydroxy-2-(6-methylpyridin-2-yl)pentyl)-4-(2-(pyridin-2-ylamino)thiazol-5-ylthio)picolinamide

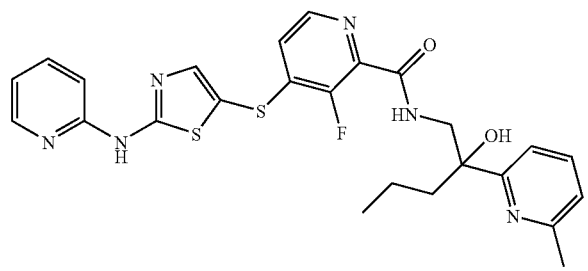

The title material was prepared using 1-amino-2-(6-methylpyridin-2-yl)pentan-2-ol (described in synthesis of amines, Example O). LC/MS (M+H)+: 525, (M−H)−: 523. Ret. time: 6.215 min. (Condition J). HRMS: calc: 525.1543; found: 525.1552.

Example 41

3-Fluoro-N-(2-(4-methoxyphenyl)-2-phenylethyl)-4-(2-(pyridin-2-ylamino)thiazol-5-ylthio)picolinamide

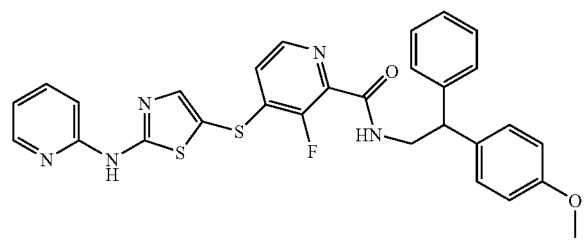

The title material was prepared using 2-(4-methoxyphenyl)-2-phenylethanamine (described in synthesis of amines, Example DD). LC/MS (M+H)+: 558. Ret. time: 2.07 min. (Condition A). HRMS: calc: 558.1434; found: 558.1415.

Example 42

4-(2-(4-Methylpyridin-2-ylamino)thiazol-5-ylthio)-N-(2-phenylcyclopropyl)picolinamide

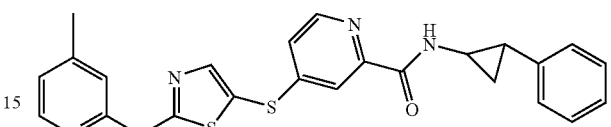

A. Synthesis 4-(2-(4-methylpyridin-2-ylamino)thiazol-5-ylthio)picolinic acid

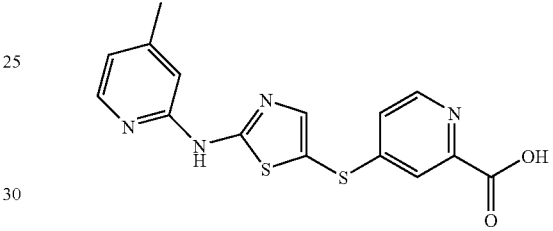

A DMF (8 mL) suspension of methyl 4-mercaptopicolinate (1.40 g, 8.16 mmol, prepared as described in Org. Prep. and Proc. Int. vol. 29 no 1, p. 117 (1997)) and sodium hydrogensulfide hydrate (0.685 g, 12.24 mmol, 1.5 eq) was bubbled with argon and heated to 35° C. 5-bromo-N-(4-methylpyridin-2-yl)thiazol-2-amine (1.103 g, 4.08 mmol, 1 eq, described in the synthesis of bromides, Example A) was diluted in methanol (15 mL) and this was treated by the DMF suspension of mercaptopyridine followed by a solution of sodium methoxide (4.6M in methanol, 2.7 mL, 12.24 mmol). The reaction was purged with argon and stirred at 65° C. for 1 hour. The reaction was then concentrated to remove most of the methanol, diluted in ethyl acetate/THF and acidified with 1N HCl. The aqueous phase was extracted with ethyl acetate (3×) but part of the compound remained in the aqueous phase. The two phases were combined and evaporated. The residue was then mixed with aqueous sodium hydroxide (5N, 8 mL, 40.8 mmol) and methanol followed by water were added. The reaction was stirred at 23° C. overnight, then acidified with 1N HCl. Methanol was evaporated and the solid was collected by filtration to give the crude title material (0.812 g, 58%) as a solid which was used as such in the next reaction. LC/MS (M+H)+: 345. HPLC ret. time (Condition B): 1.187 min.

B. Synthesis of 4-(2-(4-methylpyridin-2-ylamino)thiazol-5-ylthio)-N-(2-phenylcyclopropyl)picolinamide

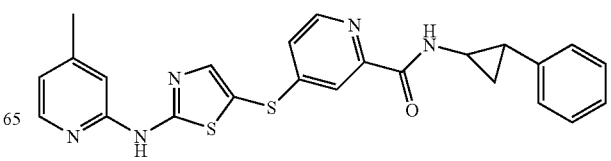

4-(2-(4-Methylpyridin-2-ylamino)thiazol-5-ylthio)picolinic acid (0.080 g, 0.233 mmol) was diluted with tetrahydrofuran (5 mL) and treated with 2-phenylcyclopropanamine (0.059 g, 0.35 mmol, 1.5 eq), HOBT (0.041 g, 0.303 mmol, 1.3 eq), EDAC (0.089 g, 0.466 mmol, 2 eq) and diisopropylethylamine (0.203 mL, 1.165 mmol, 5 eq). The reaction was stirred overnight at 23° C., then the solvent was evaporated. The residue was dissolved in DMF (2 mL) and precipitated by the addition of water. The solid was collected by filtration and dried under high vacuum to give the crude title material (0.080 g). This was purified by preparative HPLC (ammonium acetate/water/acetonitrile). The resulting solid obtained after lyophilization (0.034 g, 32%) was dissolved in ethyl acetate/THF and treated with HCl (0.1N in dioxane, 0.747 mL, 0.074 mmol). The solvents were evaporated and the residue was lyophilized to the HCl salt of the title material (0.037 g, 32%) as a solid. $^1$H NMR (400 MHz, DMSO-$d_6$) δ ppm: 1.21 (1H, dt, J=8.08 and 5.94 Hz), 1.43-1.50 (1H, m), 2.13 (1H, ddd, J=9.41, 6.13 and 3.41 Hz), 2.31 (3H, s), 3.00 (1H, td, J=8.21 and 4.80 Hz), 6.85 (1H, d, J=5.31 Hz), 6.92 (1H, s), 7.11-7.18 (3H, m), 7.26 (2H, t, J=7.45 Hz), 7.41 (1H, dd, J=5.31 and 2.02 Hz), 7.67 (1H, d, J=1.52 Hz), 7.79 (1H, s), 8.16 (1H, d, J=5.31 Hz), 8.46 (1H, d, J=5.31 Hz), 9.07 (1H, d, J=5.31 Hz), 11.70 (1H, s). LC/MS (M+H)$^+$: 460. HPLC ret. time (Condition B): 2.426 min. HRMS calcd: 460.1266, found: 460.1266.

The following example was prepared according to the procedure described in Example 42.

Example 43

4-(2-(4-Methylpyridin-2-ylamino)thiazol-5-ylthio)-N-(2-phenylpropyl)picolinamide

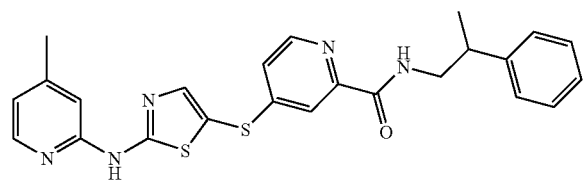

The title material was prepared using 2-phenylpropan-1-amine (commercially available). LC/MS (M+H)$^+$: 462. Ret. time: 2.456 min. (Condition B). HRMS: calc: 461.1422; found: 462.1403.

Example 44

3-Fluoro-N-(2-hydroxy-2,2-diphenylethyl)-4-(2-(4-methylpyridin-2-ylamino)thiazol-5-ylthio)picolinamide

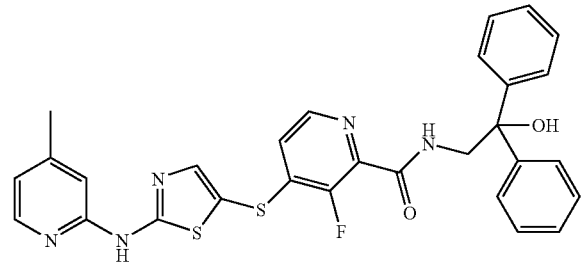

A. Synthesis of 3-fluoro-4-(2-(4-methylpyridin-2-ylamino)thiazol-5-ylthio)picolinic acid

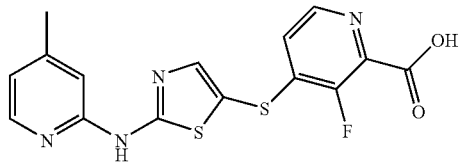

To a suspension of N-(4-methylpyridin-2-yl)-5-thiocyanatothiazol-2-amine (3.4 g, 13.69 mmol, described in the synthesis of thiocyanates, Example C) in methanol (150 mL, previously bubbled with argon) was added dithiothreitol (3.70 g, 23.96 mmol). The reaction was stirred at 23° C. for 10 minutes, then methyl 4-chloro-3-fluoropicolinate (2.27 g, 11.98 mmol) was added followed by an aqueous solution of NaOH (1N, 12 mL, 11.98 mmol). The resulting reaction mixture was stirred for 1 hour, then concentrated to about one-fourth of the volume. The mixture was then diluted with water (200 mL) and neutralized with ammonium chloride. The resulting solid was collected by filtration and vacuum dried to give the crude title material (5.7 g) as a solid. This solid was purified on silica gel Biotage chromatography (ethyl acetate) to give the title material (3.01 g, 70%) as a solid. $^1$H NMR of the compound showed contamination with dithiothreitol. The compound was used as such in the next reaction.

The solid was dissolved in THF (100 mL) and the solution was treated with aqueous sodium hydroxide (1N, 12 mL, 11.95 mmol). The reaction was stirred at 23° C. for 2 hours, then diluted with water and neutralized with 1N aq. HCl. The mixture was concentrated to remove THF and the resulting off-white solid was collected by filtration and vacuum dried to give the title material (1.86 g, 64%) as a solid. $^1$H NMR (400 MHz, DMSO-$d_6$) δ ppm: 2.31 (3H, s), 6.67-6.73 (1H, m), 6.84 (1H, d, J=4.55 Hz), 6.92 (1H, s), 7.74-7.78 (1H, m), 8.04 (1H, d, J=4.29 Hz), 8.17 (1H, t, J=4.55 Hz).

B. Synthesis of 3-fluoro-N-(2-hydroxy-2,2-diphenylethyl)-4-(2-(4-methylpyridin-2-ylamino)thiazol-5-ylthio)picolinamide

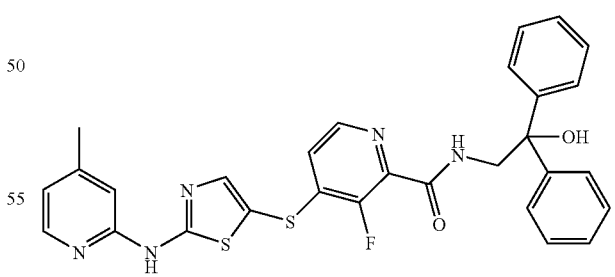

3-Fluoro-4-(2-(4-methylpyridin-2-ylamino)thiazol-5-ylthio)picolinic acid (0.25 g, 0.69 mmol) was diluted with NMP (8 mL) and treated with 2-amino-1,1-diphenylethanol (0.222 g, 1.04 mmol, 1.5 eq, described in the synthesis of amines Example D), HOBT (0.121 g, 0.897 mmol, 1.3 eq), EDAC (0.193 g, 1.38 mmol, 2 eq) and diisopropylethylamine (0.60 mL, 3.45 mmol, 5 eq). The reaction was stirred overnight at 23° C., then purified by preparative HPLC (trifluoroacetic acid/water/acetonitrile). The resulting solid obtained after lyophilization was dissolved in methanol and treated with the MP-carbonate resin (3 eq.) for 1 hour. The resin was filtered and the solvent evaporated to give the title material (0.122 g, 32%). This was dissolved in methanol and treated with HCl (0.1N in MeOH, 1 eq.). The solvent was evaporated and the residue was lyophilized to afford the title material (0.130 g) as a solid. $^1$H NMR (400 MHz, DMSO-$d_6$) δ ppm: 2.31 (3H, s), 4.12 (2H, s, J=5.56 Hz), 6.86 (1H, d, J=5.31 Hz), 6.92 (1H, s), 7.05 (1H, t, J=5.31 Hz), 7.20 (2H, t, J=7.33 Hz), 7.27-7.33 (4H, m), 7.48 (4H, d, J=7.33 Hz), 7.80 (1H, s), 8.16 (1H, d, J=5.05 Hz), 8.21 (1H, d, J=5.05 Hz), 8.31 (1H, t, J=5.43 Hz), 11.70 (1H, s). LC/MS (M+H)$^+$: 558. HPLC ret. time (Condition C): 6.145 min. HRMS calcd: 558.1434, found: 558.1437.

The following examples were prepared according to the procedure described in Example 44.

Example 45

3-Fluoro-N-(2-hydroxy-2-phenylpentyl)-4-(2-(4-methylpyridin-2-ylamino)thiazol-5-ylthio)picolinamide

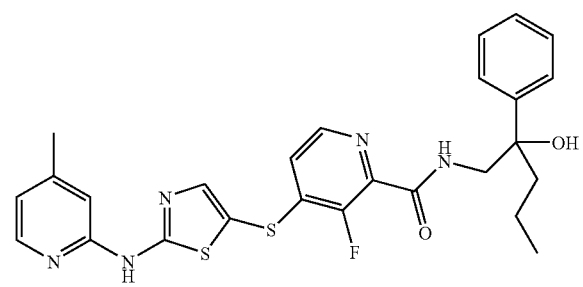

The title material was prepared using 1-amino-2-phenylpentan-2-ol (described in synthesis of amines, Example E). LC/MS (M+H)$^+$: 524, (M−H)$^-$: 522. Ret. time: 6.086 min. (Condition C). HRMS: calc: 524.1590; found: 524.1584.

Example 46

N-(2,2-Diphenylethyl)-3-fluoro-4-(2-(4-methylpyridin-2-ylamino)thiazol-5-ylthio)picolinamide

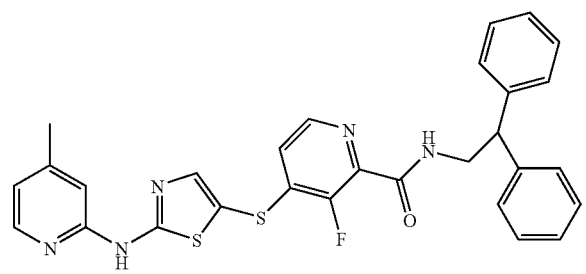

The title material was prepared using 2,2-diphenylethanamine (commercially available). LC/MS (M+H)$^+$: 542, (M−H)$^-$: 540. Ret. time: 6.783 min. (Condition C). HRMS: calc: 542.1485; found: 542.1497.

Example 47

3-Fluoro-N-(3-hydroxy-2,2-diphenylpropyl)-4-(2-(4-methylpyridin-2-ylamino)thiazol-5-ylthio)picolinamide

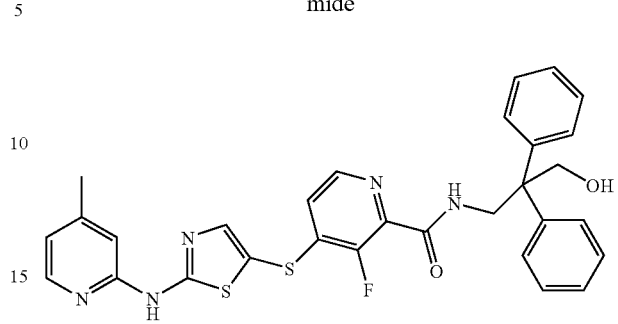

The title material was prepared using 3-amino-2,2-diphenylpropan-1-ol (described in the synthesis of amines Example P). LC/MS (M+H)$^+$: 572. Ret. time: 6.275 min. (Condition C). HRMS: calc: 572.1590; found: 572.1597.

Example 48

N-(2,2-diphenylethyl)-3-fluoro-4-(2-(4-methylpyridin-2-ylamino)thiazol-5-ylthio)picolinamide

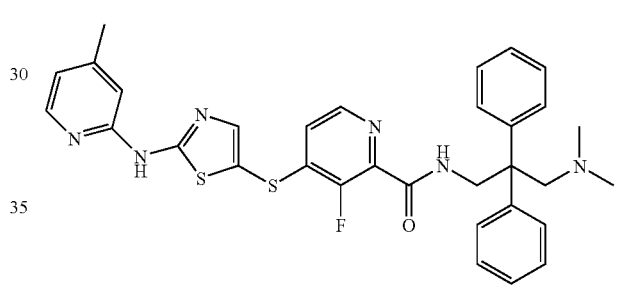

The title material was prepared using $N^1,N^1$-dimethyl-2,2-diphenylpropane-1,3-diamine (described in the synthesis of amines Example R). LC/MS (M+H)$^+$: 599. Ret. time: 5.155 min. (Condition C). HRMS: calc: 599.2063; found: 599.2047.

Example 49

N-(2,2-diphenyl-3-(piperidin-1-yl)propyl)-3-fluoro-4-(2-(4-methylpyridin-2-ylamino)thiazol-5-ylthio)picolinamide

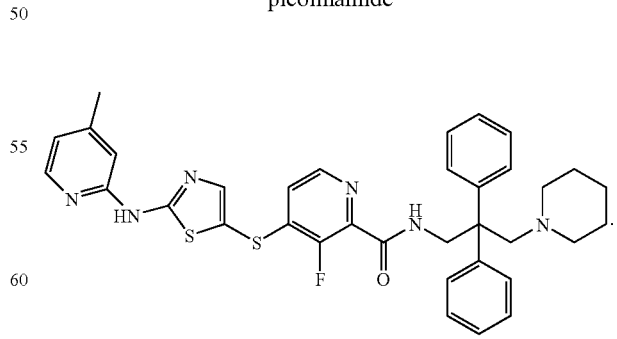

The title material was prepared using 2,2-diphenyl-3-(piperidin-1-yl)propan-1-amine (described in the synthesis of amines Example CC). LC/MS (M+H)$^+$: 639. Ret. time: 5.696 min. (Condition C). HRMS: calc: 639.2376; found: 639.2405.

Example 50

N-(2-(1,3-dioxolan-2-yl)-2,2-diphenylethyl)-3-fluoro-4-(2-(4-methylpyridin-2-ylamino)thiazol-5-ylthio)picolinamide

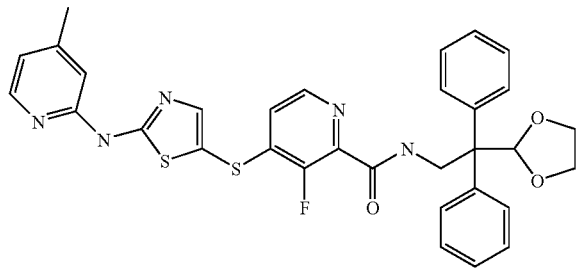

The title material was prepared using 2-(1,3-dioxolan-2-yl)-2,2-diphenylethanamine (described in the synthesis of amines Example EE). LC/MS (M+H)$^+$: 614. Ret. time: 6.796 min. (Condition C). HRMS: calc: 614.1696; found: 614.1699.

Example 51

N-(3-(diethylamino)-2,2-diphenylpropyl)-3-fluoro-4-(2-(4-methylpyridin-2-ylamino)thiazol-5-ylthio)picolinamide

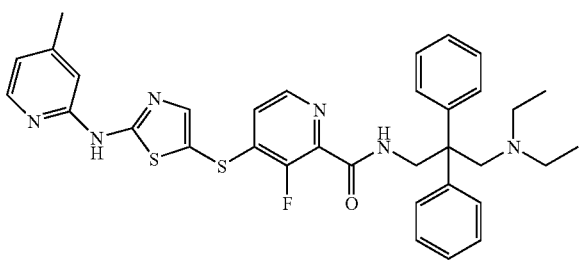

The title material was prepared using N$^1$,N$^1$-diethyl-2,2-diphenylpropane-1,3-diamine (described in the synthesis of amines Example Q). LC/MS (M+H)$^+$: 627. Ret. time: 5.573 min. (Condition C). HRMS: calc: 627.2376; found: 627.2407.

Example 52

3-Fluoro-N-(3-((2-hydroxyethyl)(methyl)amino)-2,2-diphenylpropyl)-4-(2-(4-methylpyridin-2-ylamino)thiazol-5-ylthio)picolinamide

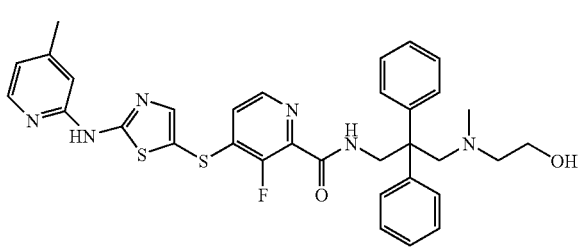

The title material was prepared using 2-((3-amino-2,2-diphenylpropyl)(methyl)amino)ethanol (described in the synthesis of amines Example S). LC/MS (M+H)$^+$: 629. Ret. time: 4.893 min. (Condition C). HRMS: calc: 629.2169; found: 629.2158.

Example 53

3-Fluoro-N-(3-((2-methoxyethyl)(methyl)amino)-2,2-diphenylpropyl)-4-(2-(4-methylpyridin-2-ylamino)thiazol-5-ylthio)picolinamide

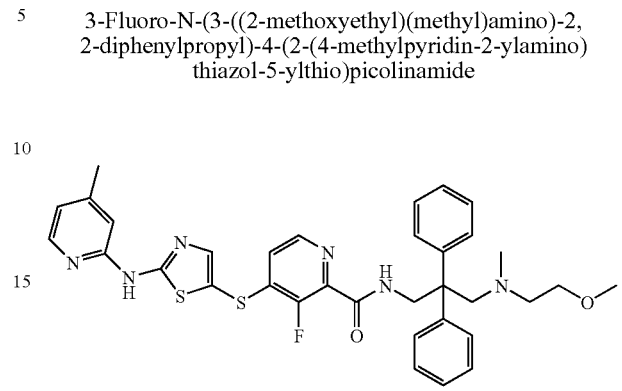

The title material was prepared using N$^1$-(2-methoxyethyl)-N$^1$-methyl-2,2-diphenylpropane-1,3-diamine (described in the synthesis of amines Example T). LC/MS (M+H)$^+$: 643. Ret. time: 5.490 min. (Condition C). HRMS: calc: 643.2325; found: 643.2314.

Example 54

N-(2-(dimethylamino)-2-phenylethyl)-3-fluoro-4-(2-(4-methylpyridin-2-ylamino)thiazol-5-ylthio)picolinamide

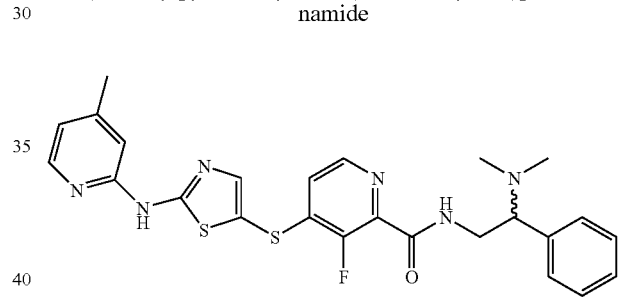

The title material was prepared using N$^1$,N$^1$-dimethyl-1-phenylethane-1,2-diamine (commercially available). LC/MS (M+H)$^+$: 509. Ret. time: 4.128 min. (Condition C).

Example 55

N-(3-(tert-butylamino)-2,2-diphenylpropyl)-3-fluoro-4-(2-(4-methylpyridin-2-ylamino)thiazol-5-ylthio)picolinamide

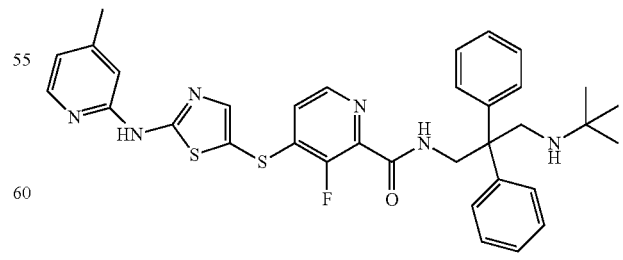

The title material was prepared using N$^1$-tert-butyl-2,2-diphenylpropane-1,3-diamine (described in the synthesis of amines, Example U). LC/MS (M+H)$^+$: 627. Ret. time: 5.775 min. (Condition C).

Example 56

3-fluoro-4-(2-(4-methylpyridin-2-ylamino)thiazol-5-ylthio)-N-(2-phenyl-2-o-tolylethyl)picolinamide

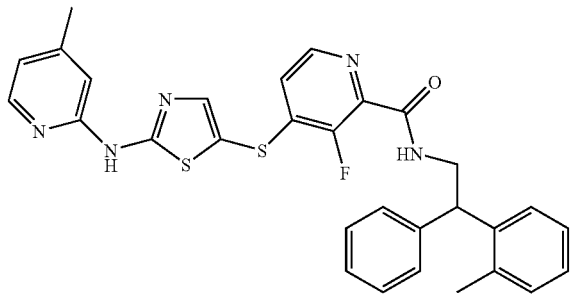

The title material was prepared using 2-phenyl-2-o-tolylethanamine (described in the synthesis of amines, Example FF). LC/MS (M+H)+: 556. Ret. time: 8.04 min. (Condition K).

Example 57

3-Fluoro-4-(2-(4-methylpyridin-2-ylamino)thiazol-5-ylthio)-N-(2-phenyl-2-(pyridin-2-yl)ethyl)picolinamide

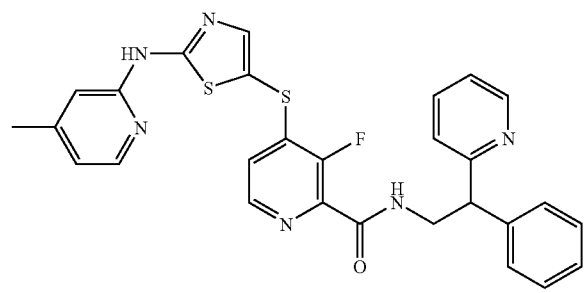

The title material was prepared using 2-phenyl-2-(pyridin-2-yl)ethanamine (described in the synthesis of amines, Example HH). LC/MS (M+H)+: 543. Ret. time: 4.461 min. (Condition C).

Example 58

N-(2-(2-bromophenyl)-2-phenylethyl)-3-fluoro-4-(2-(4-methylpyridin-2-ylamino)thiazol-5-ylthio)picolinamide

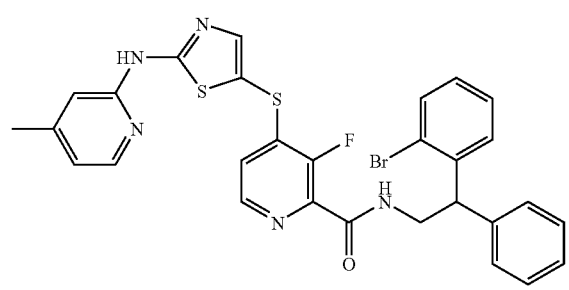

The title material was prepared using 2-(2-bromophenyl)-2-phenylethanamine (described in the synthesis of amines, Example GG). LC/MS (M+H)+: 620, 622. Ret. time: 7.141 min. (Condition C).

Example 59

3-Fluoro-N-(2-(2-((methoxymethoxy)methyl)phenyl)-2-phenylethyl)-4-(2-(4-methylpyridin-2-ylamino)thiazol-5-ylthio)picolinamide

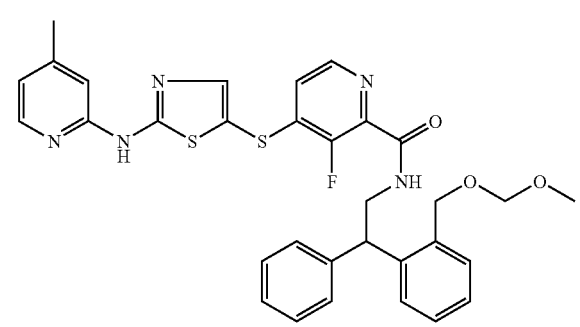

The title material was prepared using 2-(2-((methoxymethoxy)methyl)phenyl)-2-phenylethanamine (described in the synthesis of amines, Example V). LC/MS (M+H)+: 616. Ret. time: 2.112 min. (Condition M).

Example 60

3-Fluoro-N-(2-(3-((methoxymethoxy)methyl)phenyl)-2-phenylethyl)-4-(2-(4-methylpyridin-2-ylamino)thiazol-5-ylthio)picolinamide

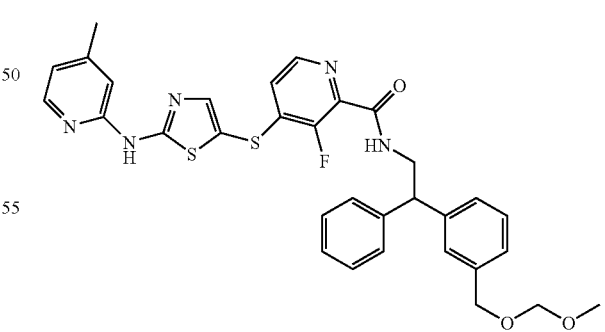

The title material was prepared using 2-(3-((methoxymethoxy)methyl)phenyl)-2-phenylethanamine (described in the synthesis of amines, Example W). LC/MS (M+H)+: 616. Ret. time: 2.32 min. (Condition I).

Example 61

3-Fluoro-N-(2-(4-((methoxymethoxy)methyl)phenyl)-2-phenylethyl)-4-(2-(4-methylpyridin-2-ylamino)thiazol-5-ylthio)picolinamide

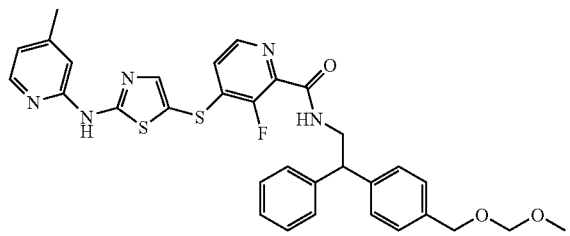

The title material was prepared using 2-(4-((methoxymethoxy)methyl)phenyl)-2-phenylethanamine (described in the synthesis of amines, Example X). LC/MS (M+H)$^+$: 616. Ret. time: 2.245 min. (Condition I).

Example 62

3-Fluoro-N-(2-(2-(methoxymethoxy)phenyl)-2-phenylethyl)-4-(2-(pyridin-2-ylamino)thiazol-5-ylthio)picolinamide

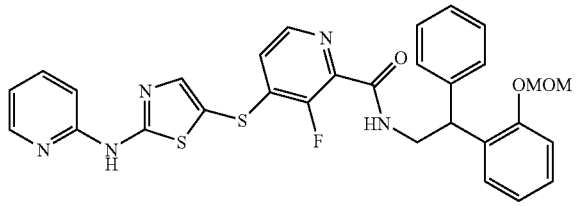

The title material was prepared using 2-(2-(methoxymethoxy)phenyl)-2-phenylethanamine (described in the synthesis of amines, Example II). LC/MS (M+H)$^+$: 602. Ret. time: 2.30 min. (Condition I).

Example 63

3-Fluoro-N-(2-(2-(hydroxymethyl)phenyl)-2-phenylethyl)-4-(2-(pyridin-2-ylamino)thiazol-5-ylthio)picolinamide

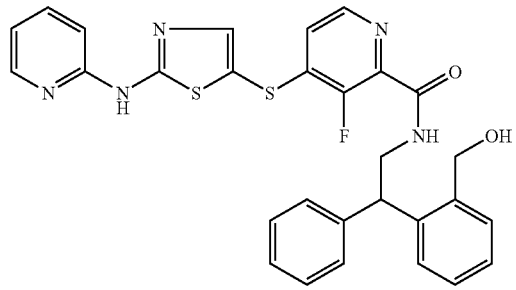

Trifluoroacetic acid (5 mL) was added to a stirring solution of 3-fluoro-N-(2-(2-((methoxymethoxy)methyl)phenyl)-2-phenylethyl)-4-(2-(pyridin-2-ylamino)thiazol-5-ylthio)picolinamide (659 mg, 1.10 mmol, described in Example 37) in dichloromethane (20 mL) and was allowed to stir overnight. LCMS of the solution showed complete conversion, with desired (21%) and TFA ester (79%). The reaction was concentrated on the Rotovap. The residue was dissolved in THF (20 mL), and with stirring NaOH (1M, 20 mL) was added. The reaction was stirred for 15 minutes and partitioned between water and dichloromethane. The dichloromethane layer was separated, washed with brine then dried (MgSO$_4$), filtered and concentrated to an oily residue which was purified on Biotage (20-100% EtOAc/Hexane, SiO$_2$, 40+S, dichloromethane solution applied by injection). The title material was obtained (306 mg) as a solid. The solid was suspended in MeOH (1 mL), then HCl (5.5 mL, 0.1M in MeOH) was added and the mixture was diluted with water and lyophilized overnight to give the salt of the product (281 mg) as a solid: $^1$H NMR (400 MHz, DMSO-d$_6$) δ ppm 8.70 (t, J=5.81 Hz, 1H), 8.29 (d, J=4.29 Hz, 1H), 8.18 (d, J=5.05 Hz, 1H), 7.80 (s, 1H), 7.74-7.79 (m, 1H), 7.36-7.40 (m, 1H), 7.25-7.33 (m, 6H), 7.16-7.23 (m, 3H), 7.10 (d, J=8.34 Hz, 1H), 6.97-7.03 (m, 2H), 4.61-4.71 (m, 2H), 4.47 (d, J=13.64 Hz, 1H); LCMS method E: ret. time: 1.98 min, (M+H)$^+$=558.

Example 64

(S)-3-Fluoro-N-(2-(2-(hydroxymethyl)phenyl)-2-phenylethyl)-4-(2-(pyridin-2-ylamino)thiazol-5-ylthio)picolinamide and (R)-3-fluoro-N-(2-(2-(hydroxymethyl)phenyl)-2-phenylethyl)-4-(2-(pyridin-2-ylamino)thiazol-5-ylthio)picolinamide

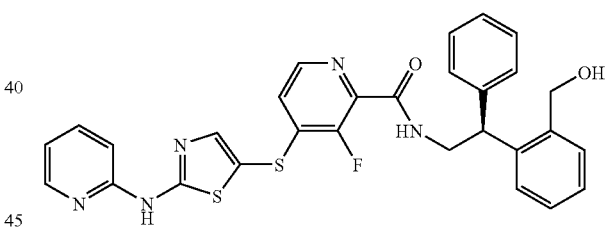

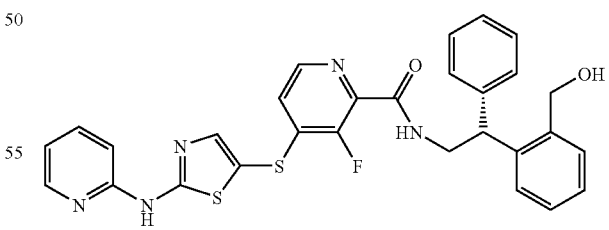

SFC chiral prep separation of 3-fluoro-N-(2-(2-(hydroxymethyl)phenyl)-2-phenylethyl)-4-(2-(pyridin-2-ylamino)thiazol-5-ylthio)picolinamide (described in Example 59) was performed on a preparative Chiralcel OD-H column using the Berger MultiGram SFC instrument (mobile phase: 30% methanol/0.1% DEA-70% CO$_2$). Two fractions, peak 1 at 38.5 min and peak 2 at 46 min were collected.

Peak 1: analyzed by using the SFC method (OD-H column, 25% methanol/0.1% DEA –75% CO$_2$) showed 99.8% chiral purity.

Peak 2: analyzed as above, showed 94.7% chiral purity.

Example 65

3-Fluoro-N-(2-(2-(hydroxymethyl)phenyl)-2-phenylethyl)-4-(2-(4-methylpyridin-2-ylamino)thiazol-5-ylthio)picolinamide

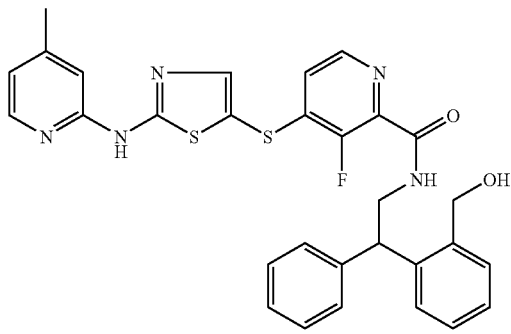

The title material was prepared as described in Example 63 in using 3-fluoro-N-(2-(2-((methoxymethoxy)methyl)phenyl)-2-phenylethyl)-4-(2-(4-methylpyridin-2-ylamino)thiazol-5-ylthio)picolinamide (described in Example 59). LC/MS (M+H)$^+$: 572. HPLC ret. time (Condition M): 1.88 min.

Example 66

3-Fluoro-N-(2-(4-(hydroxymethyl)phenyl)-2-phenylethyl)-4-(2-(4-methylpyridin-2-ylamino)thiazol-5-ylthio)picolinamide hydrochloride

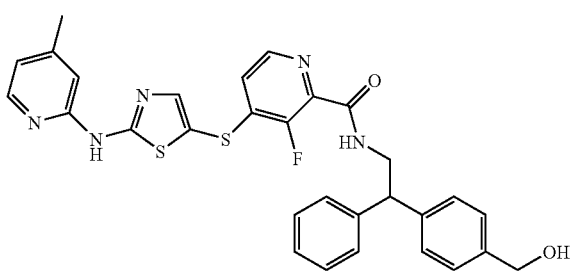

The title material was prepared as described in Example 63 in using 3-fluoro-N-(2-(4-((methoxymethoxy)methyl)phenyl)-2-phenylethyl)-4-(2-(4-methylpyridin-2-ylamino)thiazol-5-ylthio)picolinamide (described in Example 61). LC/MS (M+H)$^+$: 572. HPLC ret. time (Condition K): 5.595 min.

Example 67

3-Fluoro-N-(2-(3-(hydroxymethyl)phenyl)-2-phenylethyl)-4-(2-(4-methylpyridin-2-ylamino)thiazol-5-ylthio)picolinamide hydrochloride

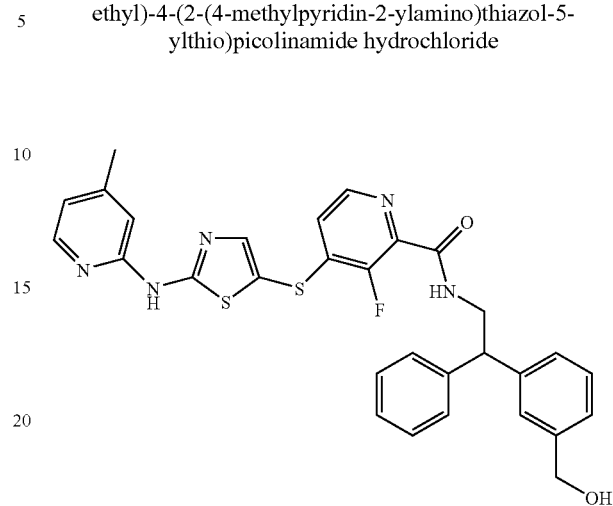

The title material was prepared as described in Example 63 in using 3-fluoro-N-(2-(3-((methoxymethoxy)methyl)phenyl)-2-phenylethyl)-4-(2-(4-methylpyridin-2-ylamino)thiazol-5-ylthio)picolinamide (described in Example 60). LC/MS (M+H)$^+$: 572. HPLC ret. time (Condition K): 5.638 min.

Example 68

3-Fluoro-N-(2-(2-hydroxyphenyl)-2-phenylethyl)-4-(2-(pyridin-2-ylamino)thiazol-5-ylthio)picolinamide

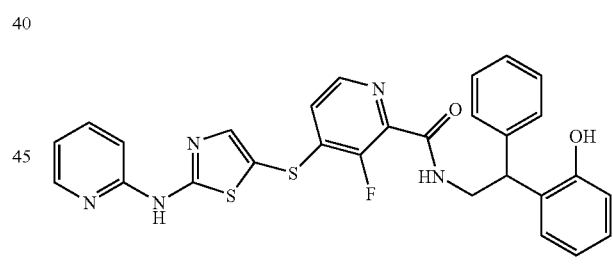

To a stirring solution of 3-fluoro-N-(2-(2-(methoxymethoxy)phenyl)-2-phenylethyl)-4-(2-(pyridin-2-ylamino)thiazol-5-ylthio)picolinamide (262 mg, 0.435 mmol, described in Example 62) in i-PrOH (4 mL) and THF (4 mL) was added HCl (conc., 0.1 mL) and allowed to stir overnight. LCMS showed some conversion, and HCl (conc. 0.9 mL) was added. After 7 h, LCMS showed complete reaction. The reaction was concentrated, dissolved in MeOH, purified by preparative HPLC (NH4OAc). The fractions containing product were combined and lyophilized to afford 48 mg of a solid, which was converted to the HCl salt affording 49 mg of a solid. $^1$H NMR (400 MHz, DMSO-d$_6$) δ ppm: 11.78 (1H, s), 9.38 (1H, s), 8.54 (1H, t, J=5.94 Hz), 8.16 (2H, dd, J=7.71, 5.18 Hz), 7.78 (1H, s), 7.21-7.29 (5H, m), 7.11-7.18 (1H, m), 6.97-7.02 (2H, m), 6.90 (1H, s), 6.84 (1H, d, J=4.80 Hz), 6.72-6.78 (2H, m), 4.69 (1H, t, J=7.96 Hz), 3.80-3.92 (2H, m), 2.29 (3H, s). LC/MS (M+H)$^+$: 558. HPLC ret. time (Condition M): 2.09 min.

Example 69

N-(3-(ethylamino)-2,2-diphenylpropyl)-3-fluoro-4-(2-(4-methylpyridin-2-ylamino)thiazol-5-ylthio)picolinamide

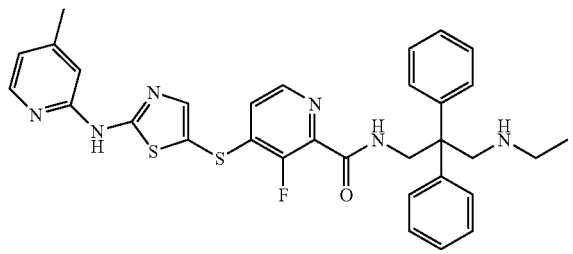

A. Synthesis of 3-fluoro-4-(2-(4-methylpyridin-2-ylamino)thiazol-5-ylthio)-N-(3-oxo-2,2-diphenylpropyl)picolinamide

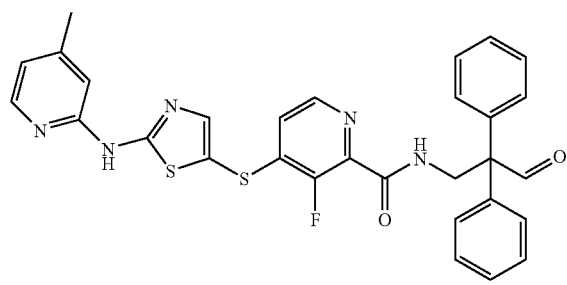

A solution of N-(2-(1,3-dioxolan-2-yl)-2,2-diphenylethyl)-3-fluoro-4-(2-(4-methylpyridin-2-ylamino)thiazol-5-ylthio)picolinamide (0.248 g, 0.4040 mmol, described in Example 50) in acetone (10 mL), water (5 mL), THF (5 mL) and conc. HCl (1 mL) was heated at gentle reflux for 10 hours. The reaction was then neutralized with aq. sat. sodium bicarbonate and the volatiles were evaporated. The solid was collected by filtration and vacuum dried to give the crude title material (0.240 g, 100%). $^1$H NMR (400 MHz, DMSO-d$_6$) δ ppm: 2.30 (3H, s), 4.27 (2H, d, J=6.32 Hz), 6.83 (1H, d, J=4.55 Hz), 6.89 (1H, s), 7.03 (1H, t, J=5.31 Hz) 7.22 (4H, d, J=7.07 Hz) 7.31-7.37 (2H, m), 7.40 (4H, t, J=7.33 Hz) 7.77 (1H, s), 8.15 (1H, d, J=5.05 Hz), 8.19 (1H, d, J=5.05 Hz), 8.28 (1H, t, J=6.19 Hz). 9.99 (1H, s) 11.82 (1H, s).

B. Synthesis of N-(3-(ethylamino)-2,2-diphenylpropyl)-3-fluoro-4-(2-(4-methylpyridin-2-ylamino)thiazol-5-ylthio)picolinamide

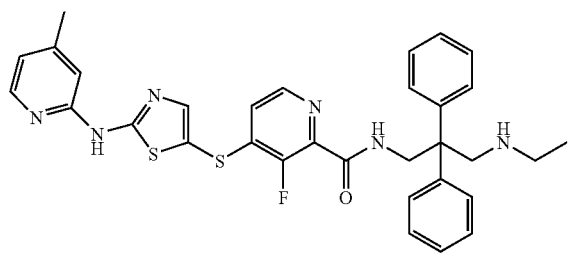

A solution of 3-fluoro-4-(2-(4-methylpyridin-2-ylamino)thiazol-5-ylthio)-N-(3-oxo-2,2-diphenylpropyl)picolinamide (0.138 g, 0.242 mmol) and ethylamine (2M in THF, 0.242 mL, 0.484 mmol) in DMF (2 mL) and trimethylorthoformate (2 mL) was stirred at 23° C. for 6 hours. Sodium triacetoxyborohydride (0.103 g, 0.484 mmol) was then added and the reaction was stirred at 23° C. for 4 days. LC/MS shows no reaction. Sodium borohydride (40 mgs) was then added followed by methanol and the reaction was stirred for 30 minutes. The reaction was then diluted with 90% acetonitrile/10% water/0.05% TFA and purified on preparative HPLC (acetonitrile/water/TFA). The solid obtained after lyophilization was dissolved in methanol and applied on a SCX SPE cartridge, washed with methanol and eluted with 2M ammonia in methanol/THF. The filtrate was evaporated and the residue was triturated in diethyl ether to give the title material (0.064 g, 44%) as a solid. This was dissolved in acetonitrile and treated with HCl (0.1N in methanol, 1.07 mL, 0.107 mmol). The solution was diluted with water and freeze dried. $^1$H NMR (400 MHz, CD$_3$OD) δ ppm: 1.37 (3H, t, J=7.33 Hz) 2.38 (3H, s) 3.13-3.19 (2H, m), 3.85 (2H, s), 4.41 (2H, s), 6.86 (1H, d, J=5.31 Hz), 6.89 (1H, s), 7.11 (1H, t, J=5.31 Hz), 7.27-7.31 (4H, m), 7.33-7.38 (2H, m), 7.39-7.45 (4H, m), 7.67 (1H, s), 8.14 (1H, d, J=5.05 Hz), 8.18 (1H, d, J=5.05 Hz). LC/MS (M+H)$^+$: 599. HPLC ret. time (Condition C): 5.183 min. HRMS calcd: 599.2063, found: 599.2047.

Example 70

4-(2-(4-(Hydroxymethyl)pyridin-2-ylamino)thiazol-5-ylthio)-N-(2-phenylcyclopropyl)picolinamide

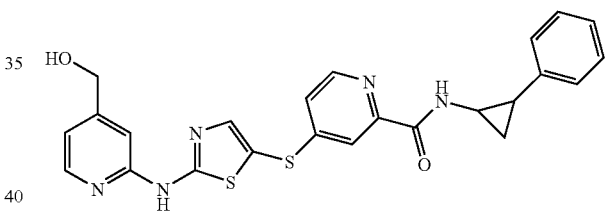

A. Synthesis of 4-(2-(4-(hydroxymethyl)pyridin-2-ylamino)thiazol-5-ylthio)picolinic acid

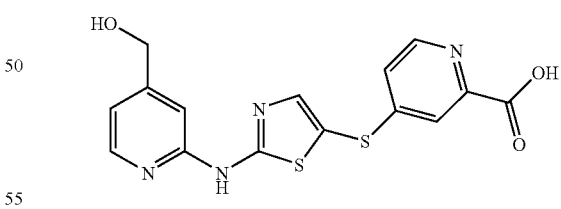

A solution of methyl 4-chloropicolinate (1.40 g, 8.16 mmol) in N,N-dimethylformamide (8 mL) was treated with sodium hydrosulfide hydrate (0.685 g, 12.24 mmol). Argon was bubbled in the solution and the reaction was stirred at room temperature for 30 minutes. The resulting solution was then stirred at 35° C. for 30 minutes. The solution changed color and was used as such in the next reaction.

A solution of 5-bromo-N-(4-((tert-butyldimethylsilyloxy)methyl)pyridine-2-yl)thiazol-2-amine (0.907 g, 2.27 mmol, described in the synthesis of bromides or thioisocyanates, Example A) in methanol (15 mL) was treated with the previously prepared solution of methyl 4-mercaptopicolinate in N,N-dimethylformamide and sodium methoxide (1.47 mL, 25% in MeOH, 6.3 mmol). The reaction was stirred at 65° C. for 1 hour. The solvent was then evaporated and the residue was dissolved in ethyl acetate/tetrahydrofuran. The reaction was acidified with 1N hydrochloric acid and the solvents were evaporated. The crude residue was then diluted in methanol (10 mL) and treated with sodium hydroxide (5N, 4.5 mL, 22.7 mmol) at 23° C. and the reaction was stirred overnight. The reaction was then acidified with 1N hydrochloric acid and the solvent was evaporated. The residue was dissolved in N,N-dimethylformamide (8 mL) and precipitated by addition of water. This was allowed to stand at 0° C. The solid was then filtered and dried under high vacuum to give the title material (0.411 g, 50%) as a solid. LC/MS (M+H)+: 361. HPLC ret. time (Condition B): 1.067 min.

B. Synthesis of 4-(2-(4-(hydroxymethyl)pyridin-2-ylamino)thiazol-5-ylthio)-N-(2-phenylcyclopropyl)picolinamide

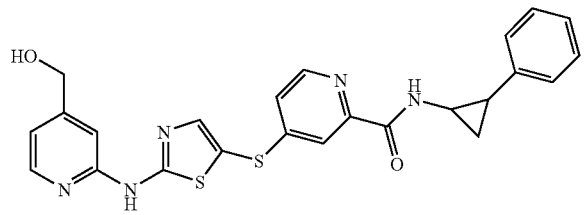

4-(2-(4-(Hydroxymethyl)pyridin-2-ylamino)thiazol-5-ylthio)picolinic acid (0.080 g, 0.222 mmol) was dissolved in THF (5 mL) and treated with 2-phenylcyclopropanamine (0.056 g, 0.333 mmol), HOBT (0.039 g, 0.289 mmol), EDAC (0.085 g, 0.444 mmol) and diisopropylethylamine (0.194 mL, 1.11 mmol). The reaction was stirred at 23° C. overnight, then the solvent was evaporated. The residue was dissolved in DMF (2 mL) and precipitated by adding water (40 mL). The solid was collected by filtration and dried under vacuum to give the title material (0.085 g) as a solid. This was purified by preparative HPLC (ammonium acetate/acetonitrile/water) and the resulting solid (0.044 g, 41%) was dissolved in ethyl acetate/THF and treated with HCl (0.1N in dioxane, 0.919 mL, 1 eq). The solvent was evaporated and the compound was lyophilized to give the HCl salt of the title material (0.047 g) as a solid. $^1$H NMR (400 MHz, DMSO-$d_6$) δ ppm: 1.21 (1H, ddd, J=7.96, 5.94, 5.81 Hz), 1.47 (1H, ddd, J=9.60, 5.18, 4.93 Hz), 2.14 (1H, ddd, J=9.47, 6.19, 3.54 Hz), 3.00 (1H, td, J=8.21, 5.05 Hz), 4.53 (3H, s), 6.91 (1H, d, J=4.55 Hz), 7.10-7.18 (4H, m) 7.26 (2H, t, J=7.33 Hz), 7.41 (1H, dd, J=5.31, 2.02 Hz), 7.68 (1H, d, J=1.52 Hz), 7.80 (1H, s), 8.21 (1H, d, J=5.30 Hz), 8.46 (1H, d, J=5.31 Hz), 9.06 (1H, d, J=5.30 Hz), 11.85 (1H, s). LC/MS (M+H)+: 476. HPLC ret. time (Condition B): 1.900 min. HRMS calcd: 476.1215, found: 476.1200.

The following example was prepared according to the procedure described in Example 70.

Example 71

4-(2-(4-(Hydroxymethyl)pyridin-2-ylamino)thiazol-5-ylthio)-N-(2-phenylpropyl)picolinamide

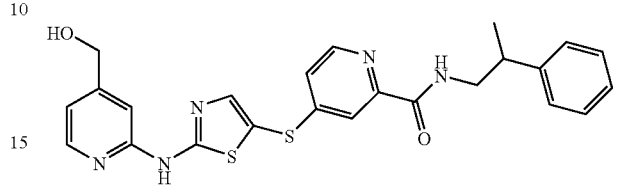

The title material was prepared as described in Example 70 in using 2-phenylpropan-1-amine (commercially available). LC/MS (M+H)+: 478. HPLC ret. time (Condition B): 1.928 min.

Example 72

3-Fluoro-N-(2-hydroxy-2,2-diphenylethyl)-4-(2-(5-(hydroxymethyl)pyridin-2-ylamino)thiazol-5-ylthio)picolinamide

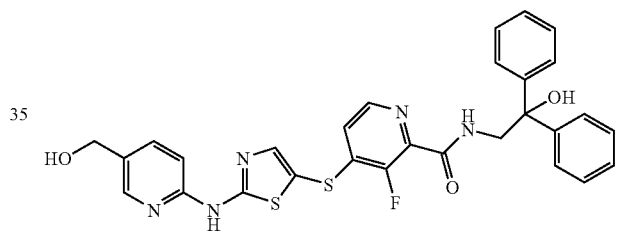

A. Synthesis of methyl 3-fluoro-4-(2-(5-(hydroxymethyl)pyridin-2-ylamino)thiazol-5-ylthio)picolinate

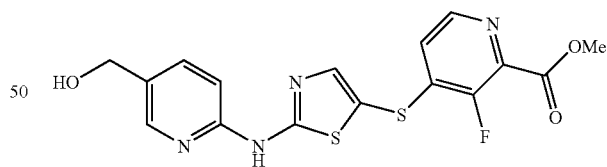

(6-(5-Thiocyanatothiazol-2-ylamino)pyridin-3-yl)methanol (1.0 g, 3.78 mmol) was dissolved in methanol (30 mL) and treated with dithiothreitol (0.582 g, 3.78 mmol). The reaction was stirred at 23° C. for 1 hour. DMF (30 mL) was then added, followed by K$_3$PO$_4$ (0.321 g, 1.51 mmol) and methyl 4-chloro-3-fluoropicolinate (0.788 g, 4.16 mmol). The reaction was stirred at 23° C. for 1 hour, then methanol was evaporated. The title material was precipitated by adding water (~150 mL), collected by filtration and dried under high vacuum to give the title material (1.287 g, 87%) as a solid. $^1$H NMR (400 MHz, DMSO-$d_6$) δ ppm: 3.34 (2H, s), 4.46 (2H, d, J=5.05 Hz) 5.22 (1H, t, J=5.56 Hz), 7.10 (1H, d, J=8.34 Hz), 7.15 (1H, t, J=5.31 Hz), 7.74 (1H, dd, J=8.59, 2.27 Hz), 7.84

(1H, s), 8.24 (1H, d, J=1.52 Hz), 8.33 (1H, d, J=5.05 Hz), 11.89 (1H, s). LC/MS (M+H)+: 393. HPLC ret. time (Condition N): 4.319 min.

B. Synthesis of 3-fluoro-4-(2-(5-(hydroxymethyl) pyridin-2-ylamino)thiazol-5-ylthio)picolinic acid

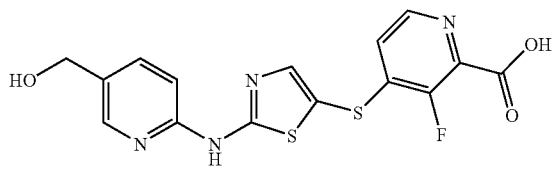

Methyl 3-fluoro-4-(2-(5-(hydroxymethyl)pyridin-2-ylamino)thiazol-5-ylthio)picolinate (0.750 g, 1.91 mmol) was dissolved in THF (20 mL) and treated with NaOH (5N, 2.5 mL, 12.5 mmol) at 23° C. The reaction was stirred for 2 hours, then water was added. The reaction was acidified with conc. HCl to pH ~2. The solvent was evaporated and the residue was diluted with water. This was extracted with ethyl acetate/THF (3×) and the combined organic layers were then dried over anhydrous magnesium sulfate, filtered and concentrated to give the title material (0.630 g, 87%) as a solid. $^1$H NMR (400 MHz, DMSO-$d_6$) δ ppm: 4.46 (2H, s), 5.22 (1H, s), 7.04-7.12 (2H, m), 7.74 (1H, dd, J=8.34, 2.27 Hz), 7.84 (1H, br s) 8.24 (1H, d, J=1.52 Hz), 8.31 (1H, d, J=5.05 Hz), 11.89 (1H, s), 13.75 (1H, s). LC/MS (M+H)+: 379. HPLC ret. time (Condition N): 2.463 min.

C. Synthesis of 3-fluoro-N-(2-hydroxy-2,2-diphenylethyl)-4-(2-(5-(hydroxymethyl)pyridin-2-ylamino) thiazol-5-ylthio)picolinamide

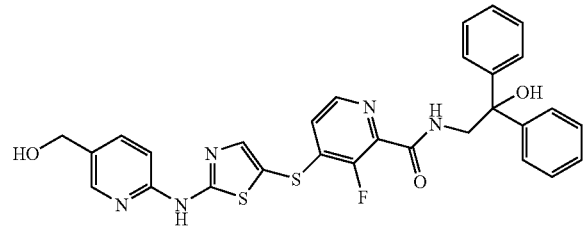

3-fluoro-4-(2-(5-(hydroxymethyl)pyridin-2-ylamino) thiazol-5-ylthio)picolinic acid (0.060 g, 0.159 mmol) was dissolved in NMP (3 mL) and treated with 2-amino-1,1-diphenylethanol (0.044 g, 0.206 mmol), HOBT (0.028 g, 0.206 mmol), EDAC (0.061 g, 0.318 mmol) and diisopropylethylamine (0.139 mL, 0.795 mmol). The reaction was stirred at 23° C. overnight, and then purified by preparative HPLC (TFA/acetonitrile/water). The residue was dissolved in THF and stirred with MP-Carbonate resin (~3 eq). The solvent was evaporated to give the title material (0.023 g, 25%). The solid was dissolved in methanol and treated with HCl (0.1N in methanol, 0.393 mL, 1 eq). The solvent was evaporated and the compound was lyophilized to give the HCl salt of the title material (0.024 g) as a solid. $^1$H NMR (400 MHz, DMSO-$d_6$) δ ppm: 4.12 (2H, d, J=5.56 Hz), 4.45 (2H, s), 7.05 (1H, t, J=5.31 Hz), 7.09 (1H, d, J=8.59 Hz), 7.20 (2H, t, J=7.33 Hz), 7.31 (4H, t, J=7.58 Hz), 7.48 (4H, d, J=7.07 Hz), 7.74 (1H, dd, J=8.46, 2.15 Hz), 7.81 (1H, s), 8.19-8.24 (2H, m), 8.31 (1H, t, J=5.56 Hz), 11.87 (1H, s). LC/MS (M+H)+: 574. HPLC ret. time (Condition C): 5.356 min. HRMS calcd: 574.1383, found: 574.1405.

The following examples were prepared according to the procedure described in Example 72.

Example 73

3-Fluoro-N-(2-hydroxy-2-phenylpentyl)-4-(2-(5-(hydroxymethyl)pyridin-2-ylamino)thiazol-5-ylthio) picolinamide

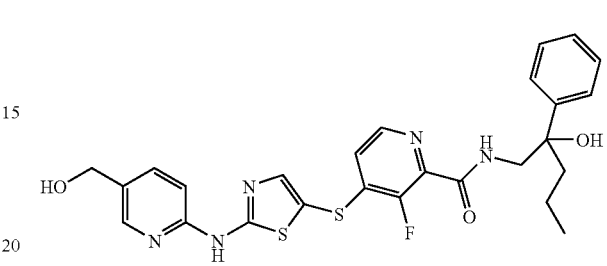

The title material was prepared as described in Example 72 in using 1-amino-2-phenylpentan-2-ol (described in the synthesis of amines, Example E). LC/MS (M+H)+: 540. HPLC ret. time (Condition B): 1.739 min. HRMS calcd: 540.1539, found: 540.1531.

Example 74

N-(2,2-diphenylpropyl)-3-fluoro-4-(2-(5-(hydroxymethyl)pyridin-2-ylamino)thiazol-5-ylthio)picolinamide

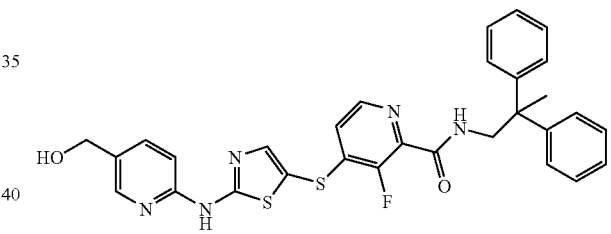

The title material was prepared as described in Example 72 in using 2,2-diphenylpropan-1-amine (commercially available). LC/MS (M+H)+: 572. HPLC ret. time (Condition C): 6.315 min. HRMS calcd: 572.1590, found: 572.1589.

Example 75

N-(2,2-diphenylethyl)-3-fluoro-4-(2-(5-(hydroxymethyl)pyridin-2-ylamino)thiazol-5-ylthio)picolinamide

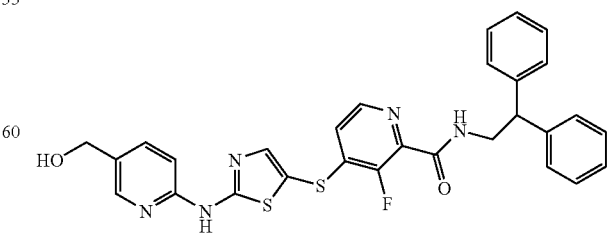

The title material was prepared as described in Example 72 in using 2,2-diphenylethanamine (commercially available).

LC/MS (M+H)+: 558. HPLC ret. time (Condition C): 5.886 min. HRMS calcd: 558.1434, found: 558.1441.

Example 76

4-(2-(5-(Aminomethyl)pyridin-2-ylamino)thiazol-5-ylthio)-3-fluoro-N-(2-hydroxy-2-phenylpentyl)picolinamide

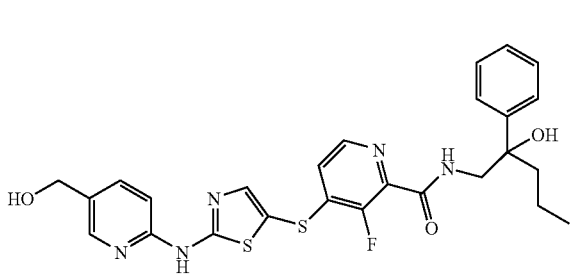

A. Synthesis of methyl 4-(2-(5-((tert-butoxycarbonylamino)methyl)pyridin-2-ylamino)thiazol-5-ylthio)-3-fluoropicolinate

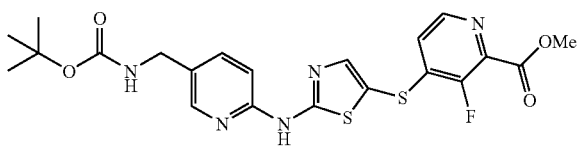

Tert-butyl (6-(5-thiocyanatothiazol-2-ylamino)pyridin-3-yl)methylcarbamate (1.5 g, 4.13 mmol) was dissolved in methanol (30 mL) and treated with dithiothreitol (0.637 g, 4.13 mmol). The reaction was stirred at 23° C. for 1 hour. DMF (30 mL) was then added, followed by K₃PO₄ (0.351 g, 1.65 mmol) and methyl 4-chloro-3-fluoropicolinate (0.861 g, 4.53 mmol). The reaction was stirred at 23° C. for 1 hour, then methanol was evaporated. The title material was precipitated by adding water (~200 mL), collected by filtration and dried under high vacuum to give the title material (1.875 g, 92%) as a solid. The compound was purified by silica gel chromatography (Biotage, dichloromethane/methanol) to give the title material as a solid. $^1$H NMR (400 MHz, DMSO-$d_6$) δ ppm: 1.38 (9H, s) 3.91 (3H, s), 4.08 (2H, d, J=5.81 Hz), 7.09 (1H, d, J=8.34 Hz), 7.14 (1H, t, J=5.31 Hz), 7.41 (1H, t, J=5.94 Hz), 7.66 (1H, dd, J=8.46, 2.15 Hz), 7.82-7.85 (1H, m), 8.17 (1H, d, J=1.77 Hz), 8.33 (1H, d, J=5.05 Hz), 11.89 (1H, s). HPLC ret. time: 5.868 min. (Condition B).

B. Synthesis of 4-(2-(5-((tert-butoxycarbonylamino)methyl)pyridin-2-ylamino)thiazol-5-ylthio)-3-fluoropicolinic acid

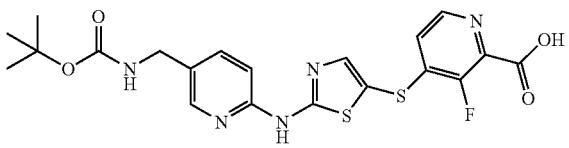

A solution of methyl 4-(2-(5-((tert-butoxycarbonylamino)methyl)pyridin-2-ylamino)thiazol-5-ylthio)-3-fluoropicolinate (1.28 g, 2.60 mmol) in tetrahydrofuran (40 mL) was treated with sodium hydroxide (5N, 3.12 mL, 15.6 mmol) at 23° C. The reaction was stirred for 2 hours, then acidified with conc. HCl to pH ~2.0. Water was then added and the aqueous phase was extracted with ethyl acetate/THF. The combined organic layers were dried over anhydrous magnesium sulfate, filtered and concentrated to give the title material (1.08 g, 87%) as a solid which was used as such in the next reaction.

C. Synthesis of tert-butyl (6-(5-(3-fluoro-2-(2-hydroxy-2-phenylpentylcarbamoyl)pyridin-4-ylthio)thiazol-2-ylamino)pyridin-3-yl)methylcarbamate

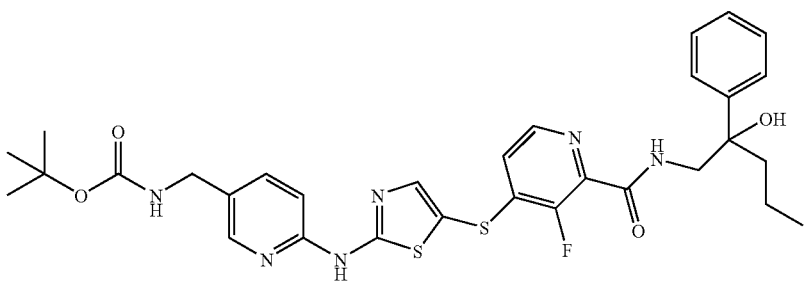

4-(2-(5-((tert-butoxycarbonylamino)methyl)pyridin-2-ylamino)thiazol-5-ylthio)-3-fluoropicolinic acid (0.470 g, 0.984 mmol) was dissolved in NMP (10 mL) and treated with 1-amino-2-phenylpentan-2-ol (0.229 g, 1.28 mmol), HOBT (0.173 g, 1.28 mmol), EDAC (0.378 g, 1.97 mmol) and diisopropylethylamine (0.858 mL, 4.92 mmol). The reaction was stirred at 23° C. overnight, then water (150 mL) was added and the precipitate was collected to give the title material (0.550 g, 88%) as a solid. Part of this compound (~0.152 g) was purified by preparative HPLC (TFA/acetonitrile/water). The title material obtained after evaporation of the solvents was dissolved in THF and stirred with MP-Carbonate resin (~3 eq). The solvent was evaporated and the residual solid was dissolved in methanol and treated with HCl (0.1N in methanol). The solvent was evaporated and the compound was lyophilized to give the HCl salt of the title material (0.034 g) as a solid. $^1$H NMR (400 MHz, DMSO-$d_6$) δ ppm: 0.75

(3H, t, J=7.28 Hz), 0.90 (1H, m), 1.22 (1H, m), 1.37 (9H, s), 1.68-1.77 (2H, m), 3.61 (2H, d, J=5.93 Hz), 4.06 (2H, d, J=5.93 Hz), 7.03 (1H, t, J=5.18 Hz), 7.07 (1H, d, J=8.15 Hz), 7.18 (1H, t, J=7.28 Hz), 7.29 (2H, t, J=7.78 Hz), 7.36 (1H, m), 7.43 (2H, d, J=7.16 Hz), 7.64 (1H, dd, J=8.52 and 2.1 Hz), 7.79 (1H, s), 8.15 (1H, d, J=1.73 Hz), 8.19-8.23 (2H, m), 11.83 (1H, s). LC/MS (M+H)+: 639. HPLC ret. time (Condition C): 6.623 min.

D. Synthesis of 4-(2-(5-(aminomethyl)pyridin-2-ylamino)thiazol-5-ylthio)-3-fluoro-N-(2-hydroxy-2-phenylpentyl)picolinamide

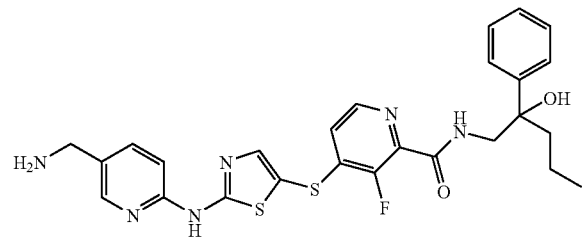

To a cold (0° C.) solution of tent-butyl (6-(5-(3-fluoro-2-(2-hydroxy-2-phenylpentylcarbamoyl)pyridin-4-ylthio)thiazol-2-ylamino)pyridin-3-yl)methylcarbamate (0.030 g, 0.047 mmol) in dichloromethane (3 mL) was added trifluoroacetic acid (20% in dichloromethane, 3 mL). The reaction was allowed to reach room temperature and was stirred for 30 minutes. The reaction was then quenched with sodium carbonate and diluted with water. This was extracted with ethyl acetate/THF and the combined extracts were dried over anhydrous magnesium sulfate, filtered and concentrated to give the crude title material.

The same reaction was then repeated with the same quantities and both crudes were combined and purified on preparative HPLC (trifluoroacetic acid/water/acetonitrile). The residue obtained, after evaporation of the solvents, was dissolved in THF and stirred with MP carbonate resin (~3 eq) for about 30 minutes. The resin was filtered and the filtrate was evaporated to give the title material (0.026 g, 52%). This was dissolved in methanol and treated with HCl (0.1N in MeOH, 0.048 mmol, 0.48 mL). The solvent was then evaporated and the compound was lyophilized to give the HCl salt of the title material (0.028 g) as a solid. 1H NMR (500 MHz, DMSO-d6) δ ppm: 0.75 (3H, t, J=7.28 Hz), 0.84-0.94 (1H, m) 1.19-1.28 (1H, m), 1.68-1.76 (2H, m), 3.61 (2H, d, J=5.68 Hz) 3.97-4.04 (2H, m), 7.04 (1H, t, J=5.19 Hz), 7.14 (1H, d, J=8.64 Hz), 7.18 (1H, t, J=7.41 Hz), 7.30 (2H, t, J=7.65 Hz) 7.43 (2H, d, J=7.16 Hz), 7.83 (1H, s) 7.86 (1H, dd, J=8.64, 2.22 Hz), 8.15 (2H, s), 8.19-8.23 (2H, m), 8.37 (1H, d, J=1.98 Hz), 12.00 (1H, s).). LC/MS (M+H)+: 539. HPLC ret. time (Condition C): 4.416 min. HRMS calcd: 539.1699, found: 539.1718.

Example 77

4-(2-(5-((2-(Dimethylamino)acetamido)methyl)pyridin-2-ylamino)thiazol-5-ylthio)-3-fluoro-N-(2-hydroxy-2-phenylpentyl)picolinamide

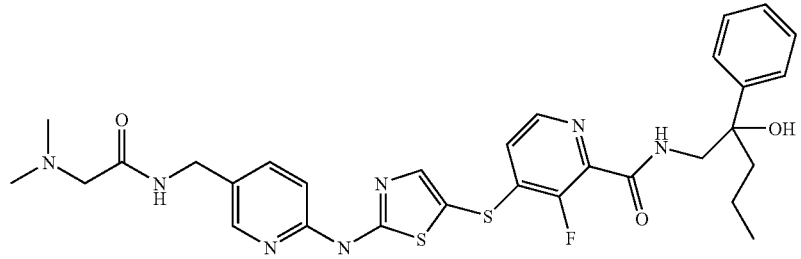

A solution of 4-(2-(5-(aminomethyl)pyridin-2-ylamino)thiazol-5-ylthio)-3-fluoro-N-(2-hydroxy-2-phenylpentyl)picolinamide (0.100 g, 0.186 mmol crude, prepared in Example 76) was treated with HOBT (0.033 g, 0.241 mmol), EDAC (0.071 g, 0.372 mmol), N,N-dimethylglycine (0.025 g, 0.241 mmol) and diisopropylethylamine (0.162 mL, 0.93 mmol) at 23° C. The reaction was stirred overnight and then purified by preparative HPLC (TFA/water/acetonitrile). After evaporation of the solvents, the residue was dissolved in THF and stirred with MP-carbonate resin (~3 eq.) for about 30 minutes. The resin was filtered and the filtrate was evaporated to give the title material (0.026 g, 23%). This was dissolved in methanol and treated with HCl (0.1N, 0.042 mmol, 0.420 mL). The solvent was then evaporated and the residue was lyophilized to give the HCl salt of the title material (0.028 g). 1H NMR (400 MHz, DMSO-d6) δ ppm 0.76 (3H, t, J=7.33 Hz), 0.85-0.94 (1H, m), 1.20-1.29 (1H, m), 1.74 2H, (td, J=10.67, 4.42 Hz), 2.80 (6H, d, J=4.55 Hz), 3.59 (3H, s), 3.95 (2H, d, J=5.05 Hz), 4.33 (2H, d, J=5.81 Hz) 7.05 (1H, t, J=5.18 Hz), 7.11 (1H, d, J=8.59 Hz), 7.20 (1H, t, J=7.33 Hz), 7.31 (2H, t, J=7.58 Hz), 7.44 (2H, d, J=7.33 Hz), 7.71 (1H, dd, J=8.46, 2.15 Hz), 7.83 (1H, s), 8.22-8.26 (3H, m) 9.04 (1H, t, J=5.56 Hz), 11.94 (1H, s). LC/MS (M+H)+: 624. HPLC ret. time (Condition C): 4.523 min. HRMS calcd: 624.227, found: 624.2238.

Example 78

3-Fluoro-N-(2-hydroxy-2-phenylpentyl)-4-(2-(5-(methoxymethyl)pyridin-2-ylamino)thiazol-5-ylthio)picolinamide

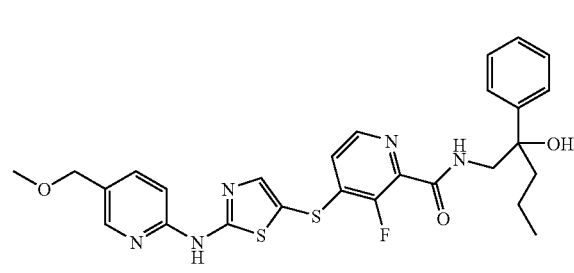

A. Synthesis of N-(5-(methoxymethyl)pyridin-2-yl)-5-thiocyanatothiazol-2-amine

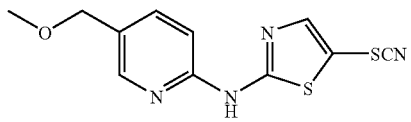

(6-(5-Thiocyanatothiazol-2-ylamino)pyridin-3-yl)methanol (0.094 g, 0.356 mmol) was dissolved in POCl₃ (3 mL) and the reaction was heated at 85° C. for 3 hours. POCl₃ was then evaporated and the resulting oil was washed with water to give a gummy solid. Methanol (10 mL) was added to the solid and the resulting suspension was stirred at 23° C. for over a month. Methanol was evaporated to almost dryness and water was added to precipitate the oil. The resulting solid was filtered and dried under vacuum to give the crude title material (0.109 g, quant.) which was used as such in the next reaction. HPLC ret. time (Condition A): 1.603 min. LC/MS (M+H)$^+$: 279.

B. Synthesis of methyl 3-fluoro-4-(2-(5-(methoxymethyl)pyridin-2-ylamino)thiazol-5-ylthio)picolinate

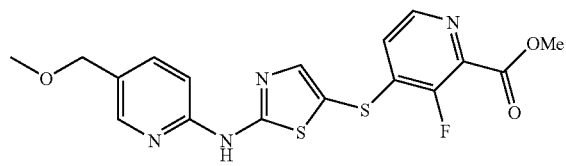

A suspension of N-(5-(methoxymethyl)pyridin-2-yl)-5-thiocyanatothiazol-2-amine (0.109 g, 0.392 mmol) in methanol (15 mL) was bubbled with argon for 10 minutes and then treated with dithiothreitol (0.079 g, 0.510 mmol). The reaction was stirred at 23° C. for 10 minutes, then methyl 4-chloro-3-fluoropicolinate (0.0743 g, 0.392 mmol) was added, followed by aq. NaOH (1N, 0.43 mL, 0.431 mmol). The resulting brown solution was stirred for 45 minutes, then concentrated to about one quarter of the volume, diluted in water (15 mL) and neutralized with aq. sat. ammonium chloride. The precipitate was filtered to give the crude title material (0.062 g, 39%) as a solid which was used as such in the next reaction. HPLC ret. time (Condition A): 1.625 min. LC/MS (M+H)$^+$: 407.

C. Synthesis of 3-fluoro-4-(2-(5-(methoxymethyl)pyridin-2-ylamino)thiazol-5-ylthio)picolinic acid

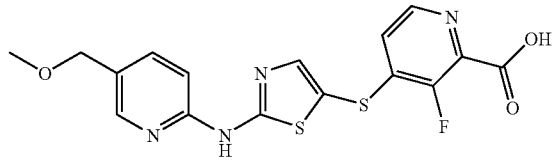

Methyl 3-fluoro-4-(2-(5-(methoxymethyl)pyridin-2-ylamino)thiazol-5-ylthio)picolinate (0.061 g, 0.150 mmol) was dissolved in THF (5 mL) and treated aq. NaOH (5N, 0.195 mL, 0.975 mmol). The reaction was stirred at 23° C. for 30 minutes, then water (1 mL) was added and the reaction was stirred for 30 more minutes. The reaction was then acidified with conc. HCl to pH ~2 and water was added again. This was extracted with ethyl acetate/THF and the combined organic extracts were dried over anhydrous magnesium sulfate, filtered and concentrated to give the title material (0.035 g, 59%) as a solid which was used as such for the next reaction. HPLC ret. time (Condition B): 1.120 min. LC/MS (M+H)$^+$: 393.

D. Synthesis of 3-fluoro-N-(2-hydroxy-2-phenylpentyl)-4-(2-(5-(methoxymethyl)pyridin-2-ylamino)thiazol-5-ylthio)picolinamide

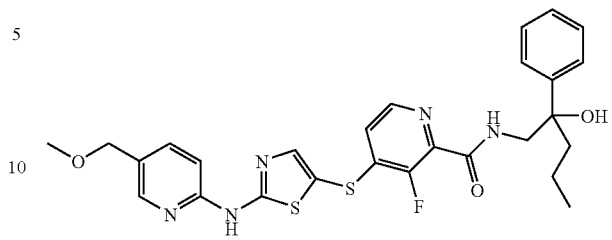

3-Fluoro-4-(2-(5-(methoxymethyl)pyridin-2-ylamino)thiazol-5-ylthio)picolinic acid (0.035 g, 0.0893 mmol) was dissolved in NMP (4 mL) and treated with 1-amino-2-phenylpentan-2-ol (0.021 g, 0.116 mmol), HOBT (0.016 g, 0.116 mmol), EDAC (0.034 g, 0.179 mmol) and diisopropylethylamine (0.078 mL, 0.447 mmol). The reaction was stirred at 23° C. overnight, then purified by preparative HPLC (TFA/acetonitrile/water). The title material obtained after evaporation of the solvents was dissolved in THF and stirred with MP-Carbonate resin (~3 eq). The solvent was evaporated and the residual solid (0.008 g, 17%) was dissolved in methanol and treated with HCl (0.1N in methanol, 0.0152 mmol, 0.152 mL). The solvent was evaporated and the compound was lyophilized to give the HCl salt of the title material (0.009 g) as a solid. $^1$H NMR (400 MHz, DMSO-d$_6$) δ ppm: 0.76 (3H, t, J=7.33 Hz), 0.83-0.94 (1H, m), 1.20-1.30 (2H, m), 1.68-1.79 (2H, m), 3.26 (3H, s), 3.62 (2H, d, J=5.81 Hz), 4.37 (2H, s) 7.05 (1H, t, J=5.31 Hz) 7.12 (1H, d, J=8.34 Hz), 7.20 (1H, t, J=7.33 Hz), 7.31 (2H, t, J=7.58 Hz), 7.44 (2H, d, J=7.33 Hz), 7.75 (1H, dd, J=8.59, 2.02 Hz), 7.83 (1H, s), 8.21-8.28 (3H, m), 11.95 (1H, s).). LC/MS (M+H)$^+$: 554. HPLC ret. time (Condition C): 6.273 min. HRMS calcd: 554.1696, found: 554.1671.

Example 79

4-(2-(5-(1-(2-(Dimethylamino)acetyl)piperidin-4-ylamino)pyridin-2-ylamino)thiazol-5-ylthio)-N-(3-hydroxy-2,2-diphenylpropyl)picolinamide

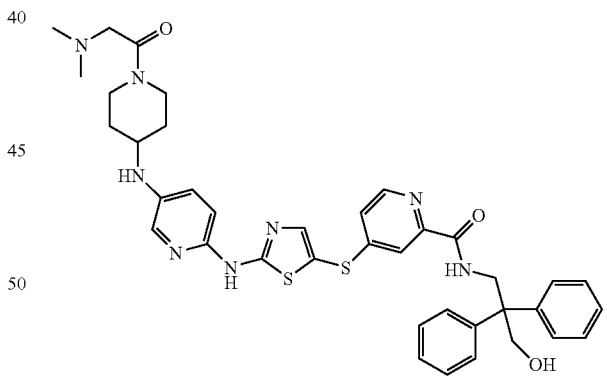

A. Synthesis of methyl 4-(2-(5-nitropyridin-2-ylamino)thiazol-4-ylthio)picolinate

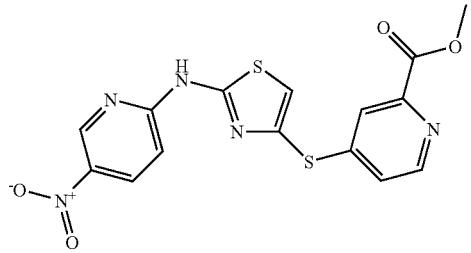

Methanol (115 mL) was added to N-(5-nitropyridin-2-yl)-4-thiocyanatothiazol-2-amine (3.24 g, 11.6 mmol) and dithiothreitol (3.6 g, 23.3 mmol) at 23° C. Methyl 4-chloropicolinate (2.18 g, 12.8 mmol) was then added followed by potassium phosphate (3.27 g, 15.4 mmol) and DMF (115 mL). The reaction was stirred overnight, then poured into ice/water (1.5 L). The resulting precipitate was filtered on paper and dried under vacuum to give the title material (4.05 g, 90%). LC/MS (M+H)$^+$: 390, (M−H)$^-$: 388. HPLC ret. time (Condition E): 1.683 min.

B. Synthesis of methyl 4-(2-(5-nitropyridin-2-ylamino)thiazol-4-ylthio)picolinate

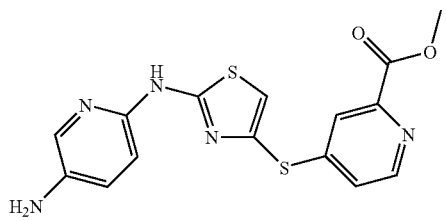

Methyl 4-(2-(5-nitropyridin-2-ylamino)thiazol-4-ylthio)picolinate (1 g, 2.78 mmol) in acetic acid (20 mL), ethanol (40 mL) and ethyl acetate (40 mL) are placed in a pressure vial. The vial is degassed with vacuum and argon three times. Platinum on carbon is then added under argon. The mixture is then hydrogenated on a Parr shaker under 60 psi of hydrogen over 16 hours. The reaction is then filtered on celite. The filter cake is washed with acetic acid and the filtrate evaporated to give the acetate salt of the compound as a solid. (500 mg, 43%). $^1$H NMR (400 MHz, DMSO-d$_6$) δ (ppm): 1.90 (s, 1H), 3.82 (s, 4H), 6.88 (d, J=8.59 Hz, 1H), 7.06 (dd, J=8.84, 2.78 Hz, 1H), 7.37 (dd, J=5.31, 2.02 Hz, 1H), 7.68 (dd, J=12.63, 1.76 Hz, 1H), 7.68 (s, 1H), 8.50 (d, J=5.05 Hz, 1H). LCMS (M+H)$^+$: 360. HPLC ret. time (Condition E): 1.370 min.

C. Synthesis of methyl 4-(2-(5-(1-(tert-butoxycarbonyl)piperidin-4-ylamino)pyridin-2-ylamino)thiazol-4-ylthio)picolinate

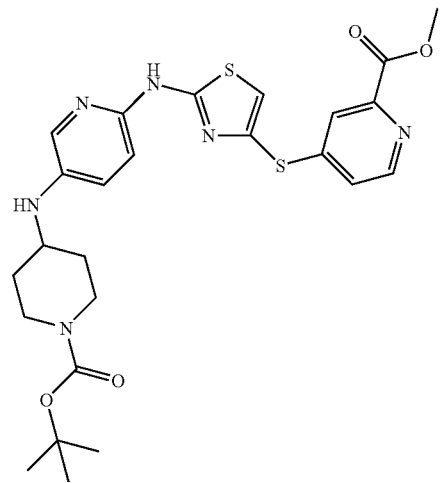

To a solution of methyl 4-(2-(5-aminopyridin-2-ylamino)thiazol-4-ylthio)picolinate (250 mg, 0.7 mmol) in methanol (10 mL) is added three drops of hydrochloric acid 2N at room temperature. Then solid tert-butyl 4-oxopiperidine-1-carboxylate (278 mg, 1.4 mmol) followed by sodium cyanoborohydride (88 mg, 1.4 mmol) are added in one portion.

The reaction is completed after 90 minutes. Hydrochloric acid (1N, 10 ml) is added and stirred for 10 min. The reaction is partitioned between saturated sodium bicarbonate and chloroform. The organic phase once separated is dried with sodium sulfate and evaporated under reduced pressure. The residue is then purified by silica gel chromatography (20% acetone/hexanes to 100% acetone) to give the compound as a tan powder (1 g, 77.3%). $^1$H NMR (400 MHz, DMSO-d$_6$) δ (ppm): 1.13-1.23 (m, 2H), 1.38 (s, 9H), 1.85 (d, J=10.61 Hz, 2H), 3.37 (s, 1H), 3.82 (s, 4H), 3.86 (s, 1H), 5.43 (d, J=8.34 Hz, 1H), 6.93 (d, J=8.84 Hz, 1H), 7.13 (dd, J=8.72, 2.65 Hz, 1H), 7.38 (d, J=5.31 Hz, 1H), 7.69 (s, 3H), 8.50 (d, J=5.30 Hz, 1H), 11.41 (s, 1H). LCMS (M+H)$^+$: 543. HPLC ret. time (Condition D): 1.560 min.

D. Synthesis of 4-(2-(5-(1-(tert-butoxycarbonyl)piperidin-4-ylamino)pyridin-2-ylamino)thiazol-4-ylthio)picolinic acid

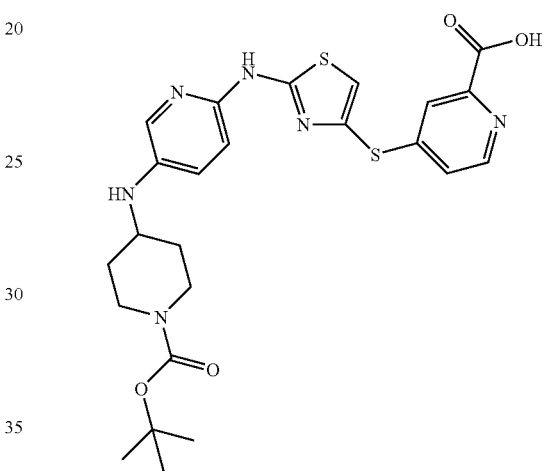

Methyl 4-(2-(5-(1-(tert-butoxycarbonyl)piperidin-4-ylamino)pyridin-2-ylamino)thiazol-4-ylthio)picolinate (0.33 g, 0.608 mmol) in THF (5 mL) was treated with sodium hydroxide (1M, 2.4 mL, 2.4 mmol) at room temperature. The mixture was stirred for 30 minutes, then saturated ammonium chloride (20 mL) was added and the THF was evaporated. The solid was filtered to give the title material as a solid (0.32 g, 97%) which was used as is. LCMS (M+H)$^+$: 529. HPLC ret. time (Condition A): 1.327 min.

E. Synthesis of tert-butyl 4-(6-(5-(2-(3-hydroxy-2,2-diphenylpropylcarbamoyl)pyridin-4-ylthio)thiazol-2-ylamino)pyridin-3-ylamino)piperidine-1-carboxylate

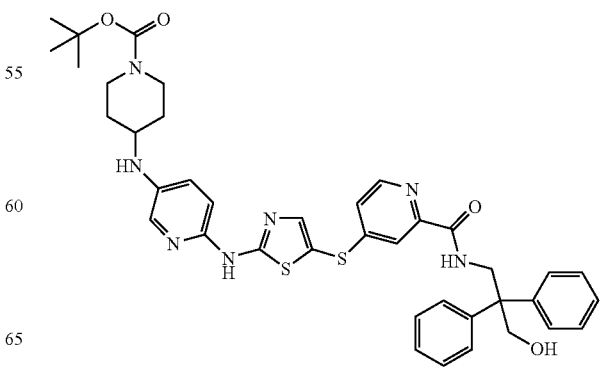

4-(2-(5-(1-(tert-butoxycarbonyl)piperidin-4-ylamino)pyridin-2-ylamino)thiazol-4-ylthio)picolinic acid (0.100 g, 0.189 mmol) was dissolved in DMF (10 mL) and treated with 3-amino-2,2-diphenylpropan-1-ol (0.086 g, 0.378 mmol), HOBT (0.026 g, 0.189 mmol), EDAC (0.073 g, 0.378 mmol) and diisopropylethylamine (0.330 mL, 1.892 mmol). The reaction was stirred at 23° C. for 3 days, then water (30 mL) was added and the precipitate was collected to give the title material (0.146 g) contaminated with EDAC. The compound was used as such in the next reaction. LC/MS (M+H)$^+$: 738. HPLC ret. time (Condition E): 2.332 min.

F. Synthesis of N-(3-hydroxy-2,2-diphenylpropyl)-4-(2-(5-(piperidin-4-ylamino)pyridin-2-ylamino)thiazol-5-ylthio)picolinamide

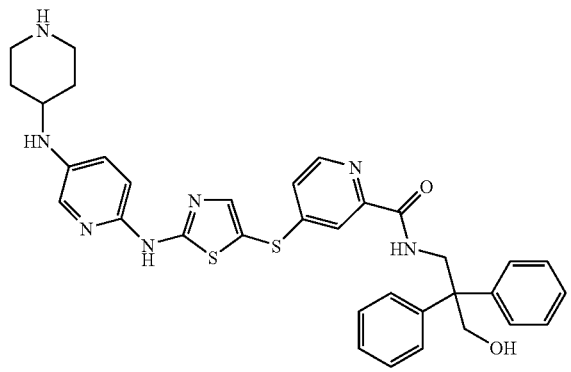

A solution of tent-butyl 4-(6-(5-(2-(3-hydroxy-2,2-diphenylpropylcarbamoyl)pyridin-4-ylthio)thiazol-2-ylamino)pyridin-3-ylamino)piperidine-1-carboxylate (0.050 g, 0.068 mmol) in dichloromethane (5 mL) was treated with trifluoroacetic acid (20% in dichloromethane, 5 mL) at 23° C. and stirred for 40 minutes. The reaction was evaporated and dried under high vacuum to give the crude title material as the bis-TFA salt (0.058 g, 98%). LC/MS (M+H)$^+$: 638. HPLC ret. time (Condition E): 1.848 min.

G. Synthesis of 4-(2-(5-(1-(2-(dimethylamino)acetyl)piperidin-4-ylamino)pyridin-2-ylamino)thiazol-5-ylthio)-N-(3-hydroxy-2,2-diphenylpropyl)picolinamide

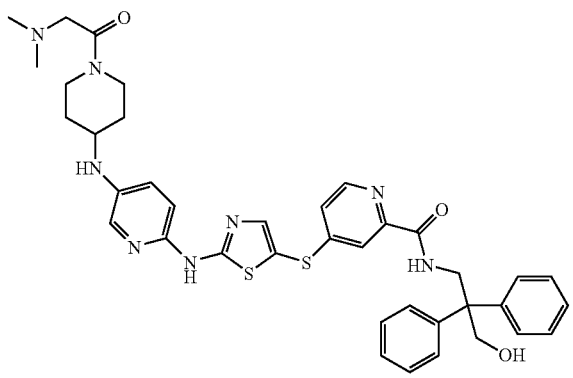

N-(3-hydroxy-2,2-diphenylpropyl)-4-(2-(5-(piperidin-4-ylamino)pyridin-2-ylamino)thiazol-5-ylthio)picolinamide (0.042 g, 0.077 mmol) was dissolved in DMF (2 mL) and treated with N,N-dimethylglycine (0.032 g, 0.307 mmol), HOBT (0.021 g, 0.154 mmol), EDAC (0.029 g, 0.154 mmol) and diisopropylethylamine (0.134 mL, 0.768 mmol). The reaction was stirred at 23° C. for ~4 hours, then with 90% acetonitrile/10% water/0.1% TFA and purified on preparative HPLC (acetonitrile/water/ammonium acetate). After evaporation of the solvents, the title material was obtained (0.024 g, 49%) and was diluted in methanol and water and treated with HCl (0.5N in water, 0.076 mL, 0.038 mmol). This mixture was lyophilized and gave the HCl salt of the title material (0.024 g) as a solid. $^1$H NMR (400 MHz, DMSO-d$_6$) δ ppm: 1.22-1.38 (2H, m), 1.91-2.01 (2H, m), 2.81 (6H, s) 2.96 (1H, t, J=10.74 Hz), 3.13-3.21 (1H, m), 3.51 (1H, s), 3.59 (1H, d, J=14.40 Hz), 4.13-4.37 (7H, m), 5.43 (1H, s), 5.56 (1H, s), 6.97 (1H, d, J=8.84 Hz), 7.15-7.21 (7H, m), 7.24-7.28 (4H, m), 7.33 (1H, dd, J=5.31, 2.02 Hz), 7.63 (1H, d, J=2.02 Hz), 7.69 (1H, s), 7.73-7.76 (1H, m), 8.33 (1H, d, J=5.31 Hz), 8.61 (1H, t, J=5.81 Hz), 9.53 (1H, s), 11.46 (1H, s). LC/MS (M+H)$^+$: 723. HPLC ret. time (Condition O): 4.433 min.

Example 80

4-(2-(5-(1-(2-(dimethylamino)acetyl)piperidin-4-ylamino)pyridin-2-ylamino)thiazol-4-ylthio)-N-(2-hydroxy-2-phenylpentyl)picolinamide

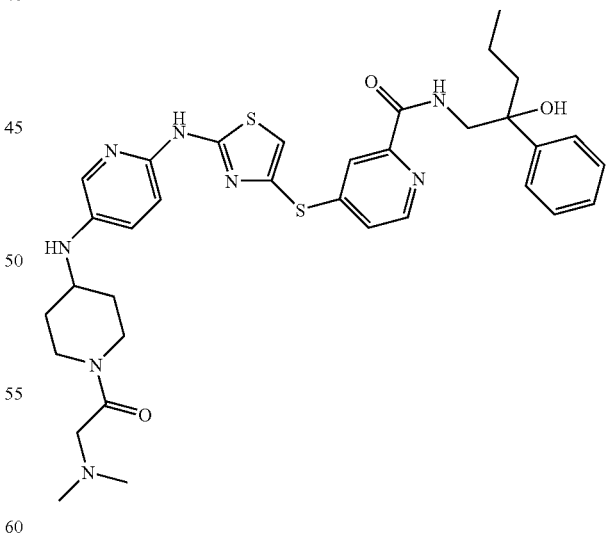

The title material was prepared as described in Example 79 in using 1-amino-2-phenylpentan-2-ol (described in the synthesis of amines, Example E). LC/MS (M+H)$^+$: 675. HPLC ret. time (Condition E): 1.732 min.

Example 81

4-(2-(5-(1-(2-(dimethylamino)acetyl)piperidin-4-ylamino)pyridin-2-ylamino)thiazol-5-ylthio)-3-fluoro-N-(2-hydroxy-2-phenylpentyl)picolinamide

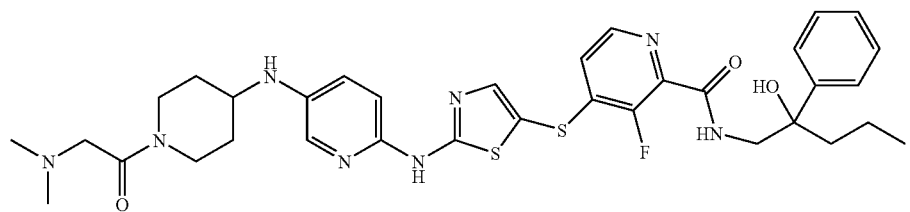

A. Synthesis of methyl 3-fluoro-4-(2-(5-nitropyridin-2-ylamino)thiazol-5-ylthio)picolinate

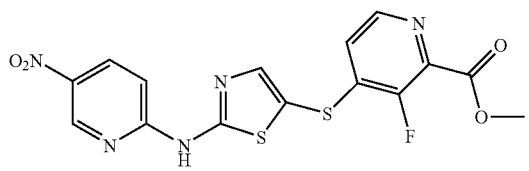

To a stirring suspension of N-(5-nitropyridin-2-yl)-5-thiocyanatothiazol-2-amine (2.00 g, 7.16 mmol) in MeOH (72 mL) was added dithiothreitol (2.22 g, 14.39 mmol). After 5 minutes, methyl 4-chloro-3-fluoropicolinate (1.51 g, 7.97 mmol), K$_3$PO$_4$ (1.98 g, 9.33 mmol) and DMF (72 mL) were sequentially added. After 2 hours, the reaction was poured into an ice/water (~1.4 L) mixture with stirring for 90 minutes, diluted to ~3.5 L with water, allowed to sit overnight. The solid was collected by filtration, washed with water and allowed to air dry overnight. The product was obtained (2.384 g, 82%) as a solid: $^1$H NMR (400 MHz, DMSO-d$_6$) δ ppm: 12.68 (1H, s), 9.19 (1H, d, J=2.78 Hz), 8.53 (1H, dd, J=9.35, 2.78 Hz), 8.32 (1H, d, J=5.05 Hz), 7.96 (1H, s), 7.23 (1H, d, J=9.35 Hz), 7.15 (1H, t, J=5.43 Hz), 3.89 (3H, s); LC/MS (M+H)$^+$: 408. HPLC ret. time (Condition B): 1.78 min.

B. Synthesis of methyl 4-(2-(5-aminopyridin-2-ylamino)thiazol-5-ylthio)-3-fluoropicolinate

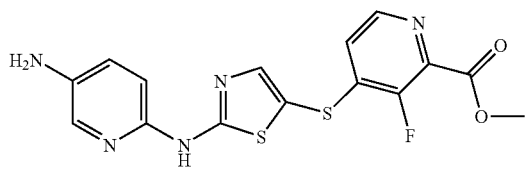

A stirring solution of methyl 3-fluoro-4-(2-(5-nitropyridin-2-ylamino)thiazol-5-ylthio)picolinate (1.77 g, 4.34 mmol), 10% Pt/C (366 mg) in acetic acid (5 mL) and THF (20 mL) was purged 4x with H$_2$, then pressurized to 140 psi in a steel bomb reactor and stirred overnight. The reaction was depressurized, and LCMS showed intermediate nitroso as predominant product. Pt/C (270 mg) was added and the reaction repressurized to 140 psi and stirred overnight. The reaction was depressurized, LCMS showed complete reaction.

The reaction was filtered through Celite, washed with THF and DCM, the filtrate was concentrated. The residue was recrystallized from EtOAc and hexane, the solid was collected by filtration and washed with hexane. The product was obtained (828 mg, 51%) as a solid: $^1$H NMR (400 MHz, DMSO-d$_6$) δ ppm: 11.43 (1H, s), 8.31 (1H, d, J=5.05 Hz), 7.72 (1H, s), 7.66 (1H, d, J=2.27 Hz), 7.11 (1H, t, J=5.31 Hz), 7.06 (1H, dd, J=8.59, 2.78 Hz), 6.87 (1H, d, J=8.59 Hz), 4.99 (2H, s), 3.89 (3H, s); LC/MS (M+H)$^+$: 378. HPLC ret. time (Condition E): 1.45 min.

C. Synthesis of methyl 4-(2-(5-(1-(tert-butoxycarbonyl)piperidin-4-ylamino)pyridin-2-ylamino)thiazol-5-ylthio)-3-fluoropicolinate

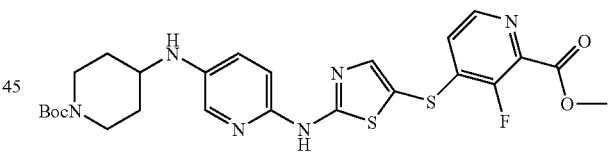

To a stirring suspension under Ar of methyl 4-(2-(5-aminopyridin-2-ylamino)thiazol-5-ylthio)-3-fluoropicolinate (0.817 g, 2.16 mmol), tert-butyl 4-oxopiperidine-1-carboxylate (0.864 g, 4.34 mmol) in MeOH (40 mL) was added HCl (conc., 0.1 mL) followed by NaBH$_3$CN (0.274 g, 4.36 mmol) with concomitant evolution of gas and the reaction becoming homogeneous. After 2.5 h, to the reaction was added HCl (10%, 10 mL) and stirred for 15 minutes. The reaction was diluted with CHCl$_3$, washed with sat. NaHCO$_3$. The organic phase was separated, and the aqueous was extracted with CHCl$_3$. The combined organic layers were dried (MgSO$_4$) and filtered. SiO$_2$ (9 g) was added then the mixture was concentrated. The residue was purified on Biotage Horizon (20-100% Acetone/hexane, SiO$_2$, 40+M). The fractions containing the product were combined and concentrated to afford the product (709 mg, 58%) as a solid: $^1$H NMR (400 MHz, DMSO-$d_6$) δ ppm: 11.46 (1H, s), 8.31 (1H, s), 7.73 (1H, s), 7.69 (1H, d, J=2.53 Hz), 7.10-7.15 (2H, m), 6.93 (1H, d, J=8.84 Hz), 5.44 (1H, d, J=8.59 Hz), 3.89 (3H, s), 3.84 (2H, d, J=12.13 Hz), 3.38 (1H, d, J=7.33 Hz), 2.88 (2H, s), 1.81-1.89 (2H, m), 1.38 (9H, s), 1.13-1.23 (2H, m); LC/MS (M+H)$^+$: 561. HPLC ret. time (Condition E): 1.99 min.

D. Synthesis of 4-(2-(5-(1-(tert-butoxycarbonyl)piperidin-4-ylamino)pyridin-2-ylamino)thiazol-5-ylthio)-3-fluoropicolinic acid

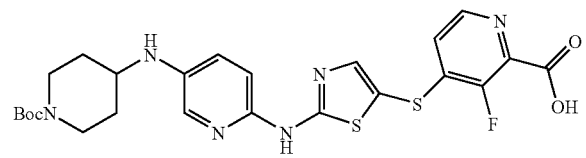

To a stirring suspension of ester methyl 4-(2-(5-(1-(tert-butoxycarbonyl)piperidin-4-ylamino)pyridin-2-ylamino)thiazol-5-ylthio)-3-fluoropicolinate (700 mg, 1.25 mmol) in THF (12 mL) was added NaOH (1M, 5 mL). After 20 minutes, the reaction was poured into 40 mL of sat. NH$_4$Cl, then partially concentrated on RotoVap. The solid was collected by filtration, washed with water, then dried under vacuum overnight. The product was obtained (700 mg, 100%) as a solid: LC/MS (M+H)$^+$: 547. HPLC ret. time (Condition B): 1.50 min.

E. Synthesis of tert-butyl 4-(6-(5-(3-fluoro-2-(2-hydroxy-2-phenylpentylcarbamoyl)pyridin-4-ylthio)thiazol-2-ylamino)pyridin-3-ylamino)piperidine-1-carboxylate

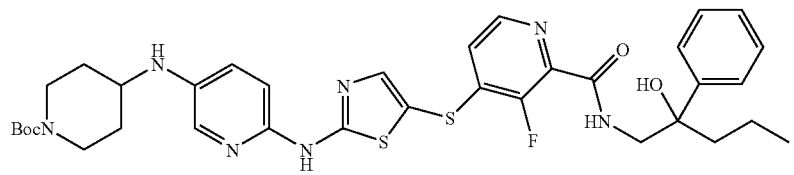

To a stirring solution of 4-(2-(5-(1-(tert-butoxycarbonyl)piperidin-4-ylamino)pyridin-2-ylamino)thiazol-5-ylthio)-3-fluoropicolinic acid (586 mg, 1.072 mmol), 1-amino-2-phenylpentan-2-ol (479 mg, 2.672 mmol), EDAC (621 mg, 3.239 mmol), HOBt (235 mg, 1.739 mmol) in NMP (7 mL) was added i-Pr$_2$NEt (0.93 mL, 5.339 mmol) and stirred overnight. LCMS showed complete reaction, which was poured into ~50 mL water and a solid precipitated. The solid was collected by filtration, washed with water and was allowed to air dry. The product was obtained (838 mg, 100%) as a solid: LC/MS (M+H)$^+$: 708. HPLC ret. time (Condition M): 1.95 min.

F. Synthesis of 3-fluoro-N-(2-hydroxy-2-phenylpentyl)-4-(2-(5-(piperidin-4-ylamino)pyridin-2-ylamino)thiazol-5-ylthio)picolinamide

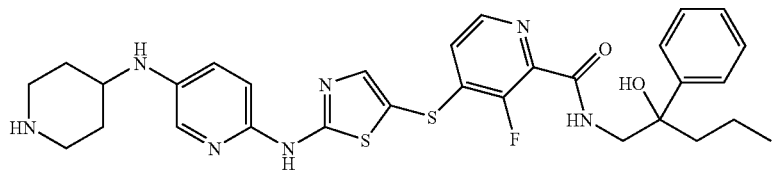

To a cool (0° C.), stirred solution of tent-butyl 4-(6-(5-(3-fluoro-2-(2-hydroxy-2-phenylpentylcarbamoyl)pyridin-4-ylthio)thiazol-2-ylamino)pyridin-3-ylamino)piperidine-1-carboxylate (838 mg, 1.072 mmol) in DCM (25 mL) was added dropwise via addition funnel a solution of 20% TFA in DCM (25 mL) over 5 minutes. The reaction was allowed to warm to rt. After 2 h, the reaction was neutralized with NaHCO$_3$ (aq. saturated) at which time a residue formed along the side of the flask. The liquid phase was decanted, the residue was dissolved in MeOH, transferred to another flask and concentrated to afford the product (737 mg, 95%) as a mixture of the desired product (89%) and the dehydrated impurity (11%), as an oil. For desired product: LC/MS (M+H)$^+$: 608. HPLC ret. time (Condition L): 1.63 min. For dehydrated product: LC/MS (M+H)$^+$: 590. HPLC ret. time (Condition A): 1.83 min.

G. Synthesis of 4-(2-(5-(1-(2-(dimethylamino)acetyl)piperidin-4-ylamino)pyridin-2-ylamino)thiazol-5-ylthio)-3-fluoro-N-(2-hydroxy-2-phenylpentyl)picolinamide

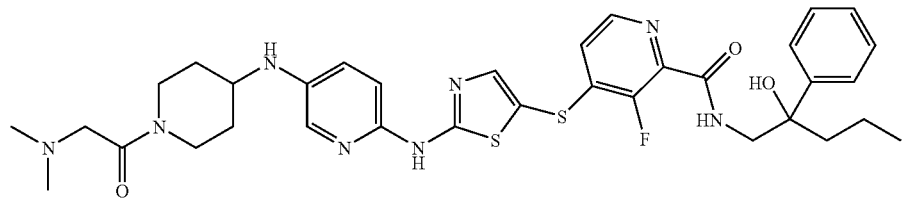

To a stirring suspension of 3-fluoro-N-(2-hydroxy-2-phenylpentyl)-4-(2-(5-(piperidin-4-ylamino)pyridin-2-ylamino)thiazol-5-ylthio)picolinamide (737 mg, 1.021 mmol), dimethylglycine (636 mg, 6.167 mmol), EDAC (590 mg, 3.078 mmol), HOBt (275 mg, 2.035 mmol) in NMP (10 mL) was added i-Pr$_2$Net (1.8 ml, 10.3 mmol). After 2 h, the reaction was diluted with PrepLC solvent B (TFA):TFA (8 mL:2 mL), filtered into 14 prepLC vials, purified on PrepLC (YMC-Pack C18 30×100 mm, NH$_4$Oac). The fractions containing the product were concentrated in SpeedVac overnight. The fractions were pooled together using MeOH and concentrated. The product was obtained (417 mg, 59%) as a solid, then converted to the HCl salt: $^1$H NMR (400 MHz, DMSO-d$_6$) δ ppm: 11.52 (1H, s), 9.53 (1H, s), 8.23 (2H, t, J=5.81 Hz), 7.78 (1H, s), 7.72 (1H, s), 7.42 (2H, d, J=7.33 Hz), 7.29 (2H, t, J=7.58 Hz), 7.18 (2H, t, J=7.33 Hz), 7.03 (1H, t, J=5.31 Hz), 6.96 (1H, d, J=8.84 Hz), 4.29 (2H, m), 3.61 (3H, d, J=5.81 Hz), 3.15 (1H, m), 2.93 (1H, t, J=11.62 Hz), 2.75-2.82 (6H, m), 1.95 (3H, t, J=9.98 Hz), 1.65-1.78 (2H, m), 1.33 (2H, s), 1.17-1.26 (2H, m), 0.88 (1H, m), 0.74 (3H, t, J=7.20 Hz); LC/MS (M+H)$^+$: 693. HPLC ret. time (Condition M): 1.40 min.

Example 82

3-Fluoro-N-(2-hydroxy-2-phenylpentyl)-4-(2-(5-((methylamino)methyl)pyridin-2-ylamino)thiazol-5-ylthio)picolinamide

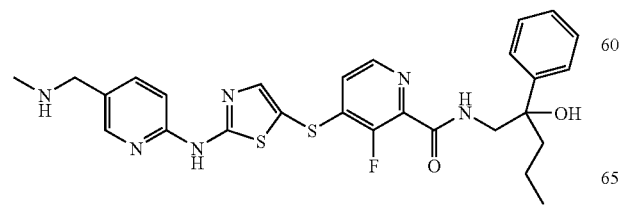

A. Synthesis of methyl 4-(2-(5-((tert-butoxycarbonyl(methyl)amino)methyl)pyridin-2-ylamino)thiazol-5-ylthio)-3-fluoropicolinate

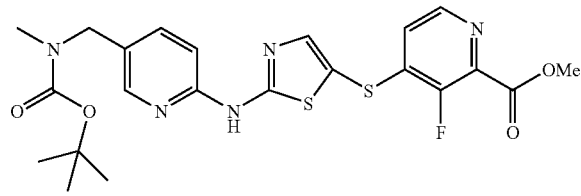

A solution of tent-butyl methyl ((6-(5-thiocyanatothiazol-2-ylamino)pyridine-3-yl)methyl)carbamate (100 mg, 0.265 mmol, described in the synthesis of thiocyanates Example C, Table 2) in methanol (10 mL) was bubbled with Ar for 15 minutes. Dithiothreitol (1.3 eq, 0.344 mmol, 53 mg) was then added and the solution was stirred at 23° C. for 15 minutes. This was treated with methyl 4-chloro-3-fluoropicolinate (0.265 mmol, 50 mg) and a solution of 0.1 mmol/mL of potassium phosphate in water (0.106 mmol, 0.4 eq, 1.06 mL). The reaction was stirred at 23° C. for 2 hours, then concentrated to one quarter of the volume by rotavap. The reaction was diluted in water (40 mL) and neutralized with a saturated solution of ammonium chloride. The solid was collected by filtration to give the title material (94 mg, 70%) as a solid. $^1$H NMR (400 MHz, DMSO-d$_6$) δ ppm: 1.41 (9H, s), 2.76 (3H, s), 3.91 (3H, s), 4.33 (2H, s), 7.06-7.21 (2H, m), 7.67 (1H, d, J=8.84 Hz) 7.84 (1H, s) 8.20 (1H, d, J=1.77 Hz) 8.33 (1H, d, J=5.05 Hz) 11.92 (1H, s). LC/MS (M+H)$^+$: 506. Ret. time: 1.98 min. (Condition A).

B. Synthesis of 4-(2-(5-((tert-butoxycarbonyl(methyl)amino)methyl)pyridin-2-ylamino)thiazol-5-ylthio)-3-fluoropicolinic acid

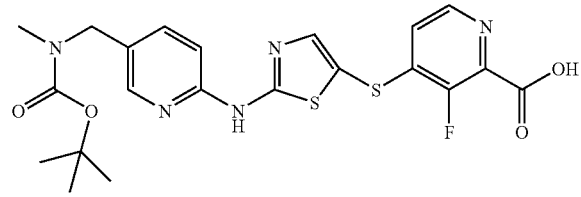

A solution of methyl 4-(2-(5-((tert-butoxycarbonyl(methyl)amino)methyl)pyridine-2-ylamino)thiazol-5-ylthio)-3-fluoropicolinate (2.56 g, 5.06 mmol) in THF (100 mL) was treated with NaOH 5N (6 eq, 30.4 mmol, 6 mL) and stirred at 23° C. for 10 min. Water (10 mL) was added to the mixture which was them stirred at 23° C. for 2 hours. The mixture was then acidified with HCl conc. to pH 4. Water was added and the aqueous phase was extracted with EtOAc (3×). The combined organic extracts were washed with brine, dried over MgSO$_4$, filtered and evaporated to give the crude title material (2.59 g) as a brown solid. $^1$H NMR (400 MHz, DMSO-d$_6$) δ ppm: 1.41 (9H, s), 2.75 (3H, s), 4.33 (2H, s), 7.04-7.18 (2H, m) 7.66 (1H, d, J=7.33 Hz) 7.84 (1H, s) 8.20 (1H, d, J=1.52 Hz) 8.30 (1H, d, J=4.80 Hz) 11.92 (1H, s). LC/MS (M+H)$^+$: 492. Ret. time: 1.308 min. (Condition B).

C. Synthesis of tert-butyl (6-(5-(3-fluoro-2-(2-hydroxy-2-phenylpentylcarbamoyl)pyridin-4-ylthio)thiazol-2-ylamino)pyridin-3-yl)methyl(methyl)carbamate

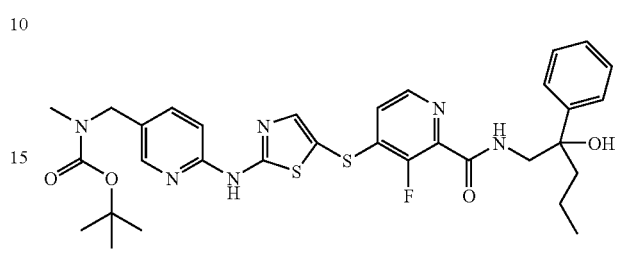

To a solution of 4-(2-(5-((tert-butoxycarbonyl(methyl)amino)methyl)pyridin-2-ylamino)thiazol-5-ylthio)-3-fluoropicolinic acid (120 mg, 0.244 mmol) and 1-amino-2-phenylpentan-2-ol (1.3 eq, 0.317 mmol, 57 mg) in NMP (4 mL) was added HOBT (1.3 eq, 0.317 mmol, 43 mg), EDAC (2 eq, 0.488 mmol, 94 mg) and diisopropylethylamine (5 eq, 1.22 mmol, 157 mg, 213 uL). The reaction was stirred at 23° C. overnight. The product was precipitated by addition of water to the reaction mixture. The solid was isolated by filtration to give the crude title material (97 mg, 61%) as a solid which was used as such in the next reaction. $^1$H NMR (400 MHz, DMSO-d6) δ ppm: 0.76 (3H, t, J=7.33 Hz), 0.90 (1H, m), 1.18-1.32 (1H, m), 1.41 (9H, s), 1.65-1.84 (2H, m), 2.75 (3H, s), 3.62 (2H, d, J=5.81 Hz), 4.32 (2H, s) 7.04 (1H, t, J=5.18 Hz), 7.11 (1H, d, J=8.59 Hz), 7.20 (1H, t, J=7.33 Hz), 7.31 (2H, t, J=7.71 Hz), 7.44 (2H, d, J=7.33 Hz), 7.66 (1H, s), 7.82 (1H, s), 8.13-8.32 (3H, m), 11.93 (1H, s). LC/MS (M+H)$^+$: 653. Ret. time: 2.257 (Condition A).

D. Synthesis of 3-fluoro-N-(2-hydroxy-2-phenylpentyl)-4-(2-(5-((methylamino)methyl)-pyridin-2-ylamino)thiazol-5-ylthio)picolinamide

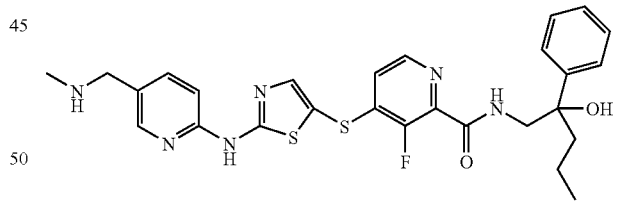

A solution of tent-butyl (6-(5-(3-fluoro-2-(2-hydroxy-2-phenylpentylcarbamoyl)pyridin-4-ylthio)thiazol-2-ylamino)pyridin-3-yl)methyl(methyl)carbamate (97 mg, 0.149 mmol) in dichloromethane (4 mL) was treated with a solution of 20% trifluoroacetic acid in dichloromethane (4 mL) and stirred at 23° C. for 90 minutes. The reaction was then quenched with saturated aqueous sodium carbonate (pH 7), diluted with water and the aqueous phase was extracted with EtOAc/THF. The combined extracts were dried over MgSO$_4$, filtered and concentrated. LC-MS of the residue showed a small amount of the dehydration compound. The title material was obtained (58 mg., 71%). The residue was dissolved in MeOH and HCl (0.1N in MeOH, 1 eq, 0.105 mmol, 1.05 mL) was added. The solvent was evaporated and the residue was lyophilized to give the HCl salt of the title material (62 mg) as a solid. $^1$H NMR (400 MHz, DMSO-d$_6$) δ ppm: 0.76 (3H, t, J=7.07 Hz), 0.81-0.97 (1H, m), 1.21-1.28 (1H, m), 1.65-1.82 (2H, m) 2.53 (3H, s), 3.63 (2H, d, J=5.81 Hz), 4.09 (2H, s) 7.05 (1H, t, J=5.18 Hz), 7.14-7.24 (2H, m), 7.31 (2H, t, J=7.58 Hz), 7.38-7.49 (2H, m), 7.86 (1H, s), 7.92 (1H, dd, J=2.27 and 8.58 Hz), 8.24 (1H, d, J=5.05 Hz), 8.41 (1H, d, J=2.02 Hz). LC/MS (M+H)$^+$: 553. Ret. time: 4.500 min. (Condition C). HRMS calcd: 553.1856, found: 553.1859.

Example 83

(S)-3-fluoro-N-(2-hydroxy-2-phenylpentyl)-4-(2-(thieno[3,2-c]pyridin-4-ylamino)thiazol-5-ylthio)picolinamide

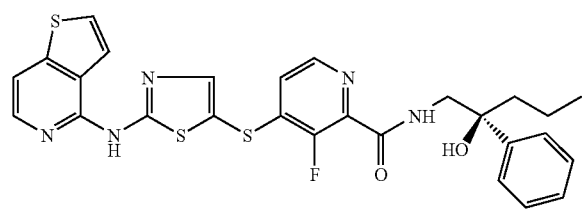

A. Synthesis of methyl 3-fluoro-4-(2-(thieno[3,2-c]pyridin-4-ylamino)thiazol-5-ylthio)picolinate

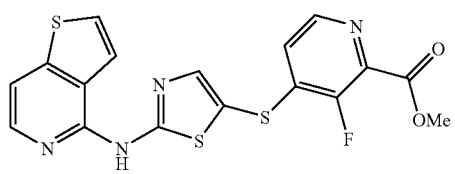

Argon was bubbled into a stirring suspension of N-(5-thiocyanatothiazol-2-yl)thieno[3,2-c]pyridin-4-amine (2.20 g, 7.58 mmol, described in the Synthesis of thiocyanates, Example C, Table 2) in methanol (300 mL) for 30 minutes. Dithiothreitol (1.52 g, 9.85 mmol) was then added to the stirring and Ar bubbling suspension. After 3 hours, dithiothreitol (2.98 g) was added again since LCMS did not show reduction to thiol and the reaction was stirred for 2 more hours. Methyl 4-chloro-3-fluoropicolinate (1.44 g, 7.60 mmol) was added followed by K$_3$PO$_4$ and the stirring was continued for 7 days. Chloropyridine (1.04 g) was added since LCMS showed incomplete reaction and the reaction was stirred overnight at room temperature and then 5 hours at reflux. The reaction was then cooled to room temperature, partially concentrated, poured into water and neutralized with saturated aqueous ammonium chloride. The resulting solid along with a viscous mass were collected by filtration and redissolved in acetone. The solid was precipitated by the addition of some water and allowing it to sit at room temperature over weekend. The resulting solid was collected by filtration, washed with water and air dried to give the title material (3.13 g, 99%) as a solid. $^1$H NMR (400 MHz, DMSO-d$_6$) δ ppm: 12.27 (1H, s), 8.32 (1H, d, J=5.05 Hz), 8.23 (1H, d, J=5.56 Hz), 8.15 (1H, d, J=5.56 Hz), 7.93 (1H, s), 7.88 (1H, d, J=5.56 Hz), 7.70 (1H, d, J=5.81 Hz), 7.16 (1H, t, J=5.31 Hz), 3.90 (3H, s); LC/MS (M+H)$^+$: 419. HPLC ret. time (Condition I): 2.00 min.

B. Synthesis of 3-fluoro-4-(2-(thieno[3,2-c]pyridin-4-ylamino)thiazol-5-ylthio)picolinic acid

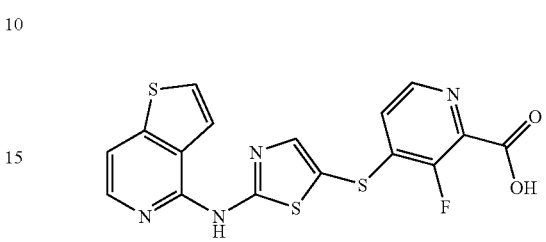

A solution of methyl 3-fluoro-4-(2-(thieno[3,2-c]pyridin-4-ylamino)thiazol-5-ylthio)picolinate (3.13 g, 7.48 mmol) was treated with aqueous sodium hydroxide (1N, 12 mL, 12.0 mmol) and was stirred at room temperature for 2 hours. The reaction was then acidified to pH ~6 with 10% aqueous HCl and then poured into water (300 mL) and allowed to sit overnight for complete precipitation. The solid was collected by filtration, washed with water and air dried to give the title material (1.86 g, 62%). $^1$H NMR (400 MHz, DMSO-d$_6$) δ ppm: 12.24 (1H, s), 8.22 (1H, d, J=5.56 Hz), 8.18 (1H, d, J=5.05 Hz), 8.15 (1H, d, J=5.81 Hz), 7.90 (1H, s), 7.87 (1H, d, J=5.56 Hz), 7.69 (1H, d, J=5.56 Hz), 6.94 (1H, t, J=5.31 Hz). LC/MS (M+H)$^+$: 405. HPLC ret. time (Condition I): 1.28 min.

C. Synthesis of (S)-3-fluoro-N-(2-hydroxy-2-phenylpentyl)-4-(2-(thieno[3,2-c]pyridin-4-ylamino)thiazol-5-ylthio)picolinamide

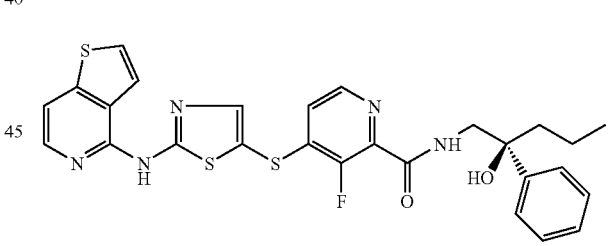

To a solution of 3-fluoro-4-(2-(thieno[3,2-c]pyridin-4-ylamino)thiazol-5-ylthio)picolinic acid (310 mg, 0.767 mmol) and (S)-1-amino-2-phenylpentan-2-ol (0.205 g, 1.14 mmol, described in Synthesis of amines, Example I) in NMP (4 mL) was added HOBT (0.162 g, 1.20 mmol), EDAC (0.446 g, 2.33 mmol) and diisopropylethylamine (0.67 mL, 3.85 mmol). The reaction was stirred at 23° C. overnight. The product was precipitated by addition of water (35 mL) to the reaction mixture. The solid was isolated by filtration and air dried to give the crude title material (412 mg) as a solid. This was purified on Biotage silica gel chromatography (10% to 75% acetone in hexane) to give the title material (0.112 g, 26%) as an oil/film that solidified. The solid was treated with HCl (0.1M in methanol, 2.0 mL), sonicated until all was dissolved, diluted with water and lyophilized to give the HCl salt of the title material (0.092 g) as a solid. $^1$H NMR (400 MHz, DMSO-d$_6$) δ ppm: 12.28 (1H, s), 8.19-8.26 (3H, m, J=5.30 Hz), 8.14 (1H, d, J=5.56 Hz), 7.91 (1H, s), 7.88 (1H, d, J=5.81 Hz), 7.70 (1H, d, J=5.56 Hz), 7.43 (2H, d, J=7.33 Hz), 7.30 (2H, t, J=7.71 Hz), 7.18 (1H, t, J=7.20 Hz), 7.07 (1H, t, J=5.18 Hz), 3.61 (2H, d, J=6.06 Hz), 1.66-1.78 (2H, m), 1.17-1.29 (1H, m), 0.82-0.94 (1H, m), 0.74 (3H, t, J=7.33 Hz). LC/MS (M+H)$^+$: 566. HPLC ret. time (Condition I): 2.28 min.

Example 84

3-Fluoro-N-(2-(2-(hydroxymethyl)phenyl)-2-phenylethyl)-4-(2-(thieno[3,2-c]pyridin-4-ylamino)thiazol-5-ylthio)picolinamide

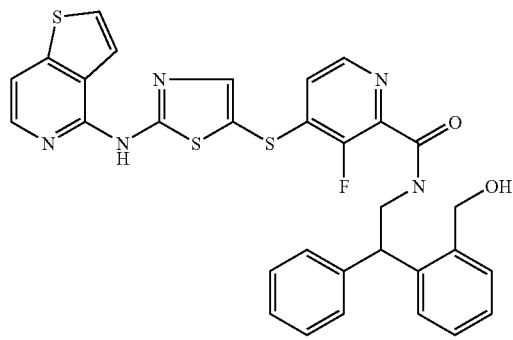

A. Synthesis of 3-fluoro-N-(2-(2-((methoxymethoxy)methyl)phenyl)-2-phenylethyl)-4-(2-(thieno[3,2-c]pyridin-4-ylamino)thiazol-5-ylthio)picolinamide

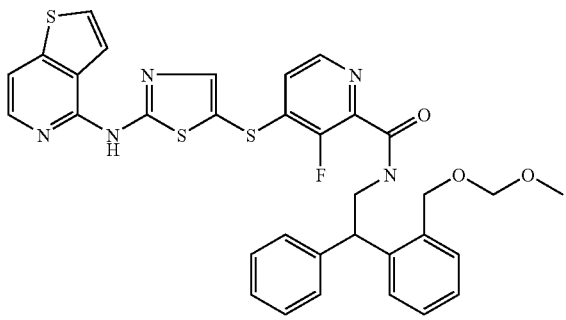

The title material was prepared as described in Example 83 in using 2-(2-((methoxymethoxy)methyl)phenyl)-2-phenylethanamine (described in Synthesis of amines, Example V). LC/MS (M+H)$^+$: 658. HPLC ret. time (Condition I): 2.410 min.

B. Synthesis of 3-fluoro-N-(2-(2-(hydroxymethyl)phenyl)-2-phenylethyl)-4-(2-(thieno[3,2-c]pyridin-4-ylamino)thiazol-5-ylthio)picolinamide

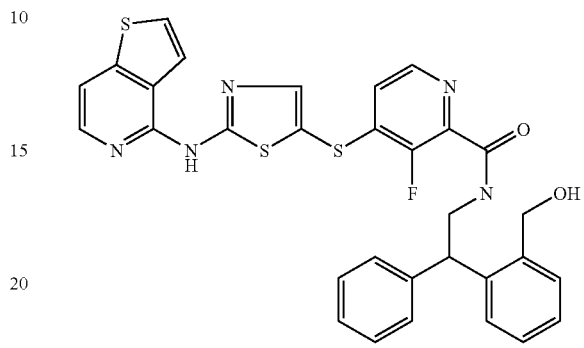

Trifluoroacetic acid (5 mL) was added to a stirring turbid solution of 3-fluoro-N-(2-(2-((methoxymethoxy)methyl)phenyl)-2-phenylethyl)-4-(2-(thieno[3,2-c]pyridin-4-ylamino)thiazol-5-ylthio)picolinamide (0.573 g, 0.871 mmol) in dichloromethane (20 mL) at room temperature. The reaction immediately cleared and became darker and was stirred overnight. The reaction was then concentrated to an oil which was then diluted in THF (20 mL) and treated with aqueous NaOH (1M, 5 mL) to hydrolyze the TFA ester. The reaction was stirred for 4 hours at room temperature, then partitioned between water and dichloromethane and the organic phase was separated. The aqueous phase was extracted with dichloromethane (3×) and the combined extracts were washed with brine, dried over anhydrous magnesium sulfate, filtered and concentrated to afford the title material (0.257 g, 48%) as a solid. This solid was suspended in methanol, then HCl (4.2 mL, 0.1M in MeOH) was added. The resulting solution was diluted with water and lyophilized overnight to give the HCl salt of the title material (0.244 g) as a solid. $^1$H NMR (400 MHz, DMSO-d$_6$) δ ppm: 3.82-3.94 (2H, m), 4.49 (1H, d, J=13.64 Hz), 4.65-4.74 (2H, m), 7.06 (1H, t, J=5.31 Hz), 7.18-7.35 (7H, m), 7.40 (1H, d, J=7.33 Hz), 7.71 (1H, d, J=5.56 Hz), 7.87-7.94 (2H, m), 8.16 (1H, d, J=5.81 Hz), 8.18-8.26 (2H, m), 8.70 (1H, t, J=5.81 Hz), 12.28 (1H, s).). LC/MS (M+H)$^+$: 614. HPLC ret. time (Condition I): 2.175 min.

Example 85

N-(2-hydroxy-2,2-diphenylethyl)-4-(2-(6-(4-(2-hydroxyethyl)piperazin-1-yl)-2-methylpyrimidin-4-ylamino)thiazol-5-ylthio)picolinamide

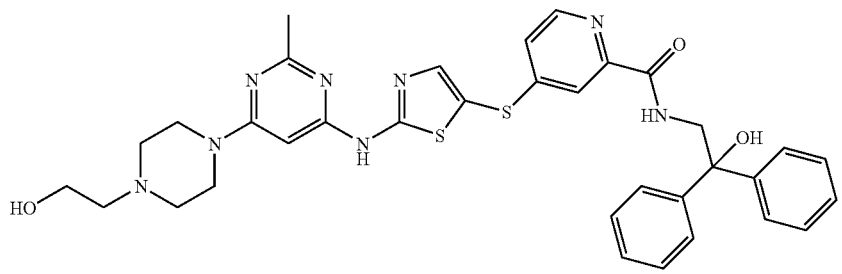

A. Synthesis of methyl 4-(2-(6-chloro-2-methylpyrimidin-4-ylamino)thiazol-5-ylthio)picolinate

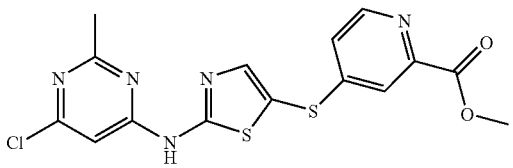

A solution of N-(6-chloro-2-methylpyrimidin-4-yl)-5-thiocyanatothiazol-2-amine (~0.725 g, ~2.56 mmol, crude, described in Synthesis of thiocyanates, Example C, Table 2) and dithiothreitol (373 mg, 2.418 mmol) in MeOH (12 mL) was stirred for 2 hours, then DMF (20 mL), methyl 4-chloro-2-picolinamide (202 mg, 1.177 mmol) and $K_3PO_4$ (127 mg, 0.597 mmol) were added. The reaction was stirred for 1.5 hours, then poured into water (~125 mL) and allowed to sit overnight for complete precipitation. The solid was collected by filtration, washed with water and vacuum dried to afford the title material (299 mg, 64% over 2 steps) as a solid. $^1$H NMR (400 MHz, DMSO-$d_6$) δ ppm: 12.39 (1H, s), 8.52 (1H, d, J=5.31 Hz), 7.91 (1H, s), 7.71 (1H, d, J=1.52 Hz), 7.37 (1H, dd, J=5.31, 2.02 Hz), 6.92 (1H, s), 3.82 (3H, s), 2.52 (3H, s). LC/MS (M+H)$^+$: 394, 396. HPLC ret. time (Condition I): 1.652 min.

B. Synthesis of 4-(2-(6-chloro-2-methylpyrimidin-4-ylamino)thiazol-5-ylthio)picolinic acid

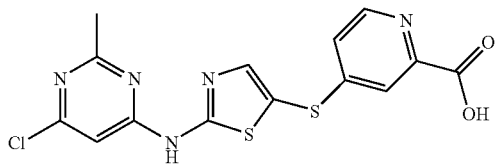

To a stirring solution of methyl 4-(2-(6-chloro-2-methylpyrimidin-4-ylamino)thiazol-5-ylthio)picolinate (292 mg, 0.741 mmol) in THF (8 mL) was added NaOH (8 mL, 1M in water). After 6 h, the reaction was acidified with 10% HCl to pH ~6 at which time a solid precipitated. The solid was collected by filtration, washed with water and allowed to dry overnight to give the title material (239 mg, 85%) as a solid. $^1$H NMR (400 MHz, DMSO-$d_6$) δ ppm: 12.55 (1H, s), 8.33 (1H, d, J=5.31 Hz), 7.84 (1H, s), 7.57 (1H, d, J=1.77 Hz), 7.16 (1H, dd, J=5.31, 2.02 Hz), 6.90 (1H, s), 2.51 (3H, s). LC/MS (M+H)$^+$: 380, 382. HPLC ret. time (Condition I): 1.175 min.

C. Synthesis of 4-(2-(6-(4-(2-hydroxyethyl)piperazin-1-yl)-2-methylpyrimidin-4-ylamino)thiazol-5-ylthio)picolinic acid

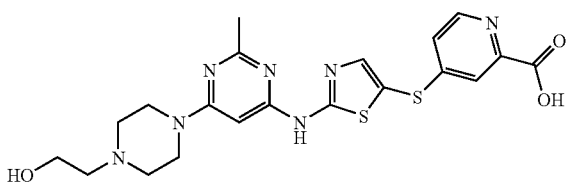

To a stirring solution of 4-(2-(6-chloro-2-methylpyrimidin-4-ylamino)thiazol-5-ylthio)picolinic acid (104 mg, 0.274 mmol) and 2-(piperazin-1-yl)ethanol (195 mg, 1.50 mmol) in n-BuOH (2 mL) was added i-Pr$_2$NEt (0.20 mL, 1.15 mmol). The reaction was then heated to 115° C. in a sealed reaction vessel overnight. The reaction was cooled to room temperature and the solid collected by filtration, the filter cake was washed with n-BuOH then air dried to give the title material (89.5 mg, 69%) as a solid. $^1$H NMR (400 MHz, DMSO-$d_6$) δ ppm: 11.59 (1H, s), 8.27 (1H, d, J=5.05 Hz), 7.71 (1H, s), 7.53 (1H, d, J=2.02 Hz), 7.07 (1H, dd, J=5.05, 2.02 Hz), 6.03 (1H, s), 4.45 (1H, t, J=4.67 Hz), 3.49 (6H, s), 2.41 (2H, t, J=6.32 Hz), 2.33 (3H, s). LC/MS (M+H)$^+$: 474. HPLC ret. time (Condition I): 1.097 min.

D. Synthesis of N-(2-hydroxy-2,2-diphenylethyl)-4-(2-(6-(4-(2-hydroxyethyl)piperazin-1-yl)-2-methylpyrimidin-4-ylamino)thiazol-5-ylthio)picolinamide

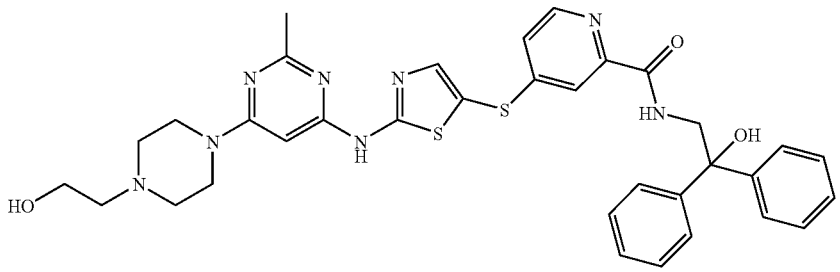

To a solution of 4-(2-(6-(4-(2-hydroxyethyl)piperazin-1-yl)-2-methylpyrimidin-4-ylamino)thiazol-5-ylthio)picolinic acid (43.2 mg, 0.0912 mmol) and 2-amino-1,1-diphenylethanol (30.8 mg, 0.144 mmol, described in Synthesis of amines, Example D) in NMP (3 mL) was added HOBT (12.3 mg, 0.0910 mmol), EDAC (27.4 mg, 0.143 mmol) and diisopropylethylamine (0.05 mL, 0.281 mmol). The reaction was stiffed at 23° C. overnight and was purified on Prep HPLC (water/acetonitrile/ammonium acetate) to give the title material (26.7 mgs, 44%) as a solid. $^1$H NMR (400 MHz, DMSO-$d_6$) δ ppm: 10.51 (1H, s), 8.35-8.42 (2H, m), 7.75 (s, 1H), 7.62 (1H, d, J=1.26 Hz), 7.43 (5H, d, J=7.07 Hz), 7.34 (1H, dd, J=5.31, 2.02 Hz), 7.27 (5H, t, J=7.71 Hz), 7.16 2H, t, J=7.33 Hz), 6.30 (1H, s), 6.03 (1H, s), 4.45 (1H, t, J=5.18 Hz), 4.09 (2H, d, J=5.56 Hz), 3.50 (7H, s), 2.41 (3H, t, J=6.32 Hz), 2.33 (3H, s). LC/MS (M+H)$^+$: 669. HPLC ret. time (Condition E): 1.84 min. HRMS calcd: 669.2430; found: 669.2434.

The invention claimed is:

1. The compound according to formula II

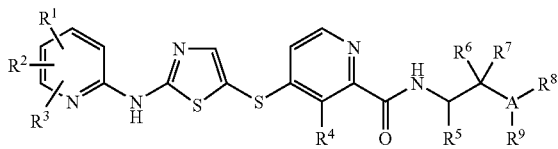

(II)

wherein

A is an aryl or a heteroaryl group;

$R^1$, $R^2$ and $R^3$ are independently hydrogen, alkyl, substituted alkyl, aryl, substituted aryl, cycloalkyl, substituted cycloalkyl, hydroxy, hydroxyalkyl, alkoxy, substituted alkoxy, halogen, haloalkyl, haloalkoxy, alkanoyl, substituted alkanoyl, amino, substituted amino, aminoalkyl, substituted aminoalkyl, alkylamino, substituted alkylamino, amide, substituted amide, carbamate, ureido, cyano, sulfonamido, substituted sulfonamido, alkylsulfone, nitro, thio, thioalkyl, alkylthio, disubstituted amino, alkylsulfonyl, alkylsulfinyl, carboxy, alkoxycarbonyl, alkylcarbonyloxy, carbamoyl, substituted carbamoyl, alkenyl, substituted alkenyl, alkynyl, substituted alkynyl or alkylcarbonyl;

$R^4$ is hydrogen, alkyl, substituted alkyl, hydroxy, cyano or halogen;

$R^5$, $R^6$ and $R^7$ are independently hydrogen, alkyl, substituted alkyl, aryl, substituted aryl, hydroxy, hydroxyalkyl, alkoxy, substituted alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkynyl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino or alkylaminocarbonyl;

$R^8$ and $R^9$ are independently hydrogen, alkyl, substituted alkyl, aryl, substituted aryl, alkylidene, substituted alkylidene, hydroxy, hydroxyalkyl, alkoxy, substituted alkoxy, alkoxyalkoxyalkyl halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, alkenyl, substituted alkenyl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylthio, arylalkylthio, arylsulfonyl, arylalkylsulfonyl, alkylsulfonyl, arylcarbonylamino or alkylaminocarbonyl, or $R^8$ and $R^9$ are taken together with the atoms to which they are attached to form an optionally substituted carbobicyclic or heterobicyclic ring;

or a pharmaceutically acceptable salt or a stereoisomer thereof.

2. A compound of formula IV

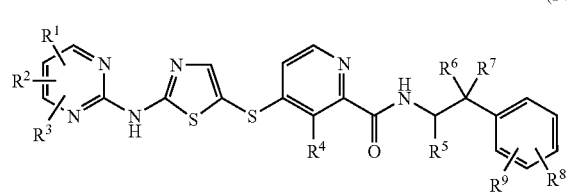

(IV)

wherein $R^1$, $R^2$ and $R^3$ are independently hydrogen, alkyl, substituted alkyl, aryl, substituted aryl, cycloalkyl, substituted cycloalkyl, hydroxy, hydroxyalkyl, alkoxy, substituted alkoxy, halogen, haloalkyl, haloalkoxy, alkanoyl, substituted alkanoyl, amino, substituted amino, aminoalkyl, substituted aminoalkyl, alkylamino, substituted alkylamino, amide, substituted amide, carbamate, ureido, cyano, nitro, carboxy, alkoxycarbonyl, alkylcarbonyloxy, carbamoyl, substituted carbamoyl, alkenyl, substituted alkenyl, alkynyl, substituted alkynyl or alkylcarbonyl;

$R^4$ is hydrogen, alkyl, substituted alkyl, hydroxy, cyano or halogen;

$R^5$, $R^6$ and $R^7$ are independently hydrogen, alkyl, substituted alkyl, aryl, substituted aryl, hydroxy, hydroxyalkyl, alkoxy, substituted alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, disubstituted amino, amide, substituted amide, carbamate, substituted carbamate, ureido, cyano, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, carboxy, alkoxycarbonyl, alkylcarbonyloxy, carbamoyl, alkenyl, substituted alkynyl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylcarbonylamino or alkylaminocarbonyl;

$R^8$ and $R^9$ are independently hydrogen, alkyl, substituted alkyl, aryl, substituted aryl, hydroxy, hydroxyalkyl, alkoxy, substituted alkoxy, alkoxyalkoxyalkyl halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, carboxy, alkoxycarbonyl, alkylcarbonyloxy, carbamoyl, alkenyl, substituted alkenyl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylcarbonylamino or alkylaminocarbonyl, or $R^8$ and $R^9$ are taken together with the atoms to which they are attached to form an optionally substituted carbobicyclic or heterobicyclic ring;

or a pharmaceutically acceptable salt or a stereoisomer thereof.

3. A compound of formula V

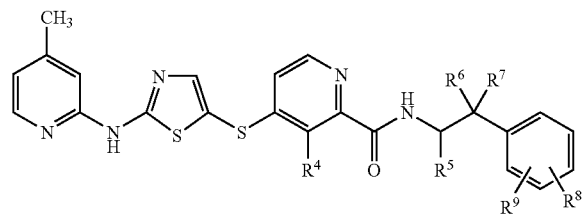

(V)

wherein:
$R^4$ is hydrogen, alkyl, substituted alkyl, hydroxy, cyano or halogen;
$R^5$, $R^6$ and $R^7$ are independently hydrogen, alkyl, substituted alkyl, aryl, substituted aryl, hydroxy, hydroxyalkyl, alkoxy, substituted alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, disubstituted amino, amide, substituted amide, carbamate, substituted carbamate, ureido, cyano, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, carboxy, alkoxycarbonyl, alkylcarbonyloxy, carbamoyl, alkenyl, substituted alkynyl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylcarbonylamino or alkylaminocarbonyl;

$R^8$ and $R^9$ are independently hydrogen, alkyl, substituted alkyl, aryl, substituted aryl, hydroxy, hydroxyalkyl, alkoxy, substituted alkoxy, alkoxyalkoxyalkyl halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, carboxy, alkoxycarbonyl, alkylcarbonyloxy, carbamoyl, alkenyl, substituted alkenyl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocyclyl, substituted heterocyclyl, alkylcarbonyl, substituted heteroalkyl, heteroalkenyl, substituted heteroalkenyl, heteroalkynyl, substituted heteroalkynyl, arylamino, arylalkylamino, alkanoylamino, aroylamino, arylalkanoylamino, arylcarbonylamino or alkylaminocarbonyl, or $R^8$ and $R^9$ are taken together with the atoms to which they are attached to form an optionally substituted carbobicyclic or heterobicyclic ring;

or a pharmaceutically acceptable salt or a stereoisomer thereof.

4. A pharmaceutical composition comprising one or more compounds of claim 1 and a pharmaceutically acceptable carrier.

5. A pharmaceutical composition comprising one or more compounds of claim 2 and a pharmaceutically acceptable carrier.

* * * * *